(12) United States Patent
Haigh et al.

(10) Patent No.: US 7,304,087 B2
(45) Date of Patent: Dec. 4, 2007

(54) 1-ACYL-PYRROLIDINE DERIVATIVES FOR THE TREATMENT OF VIRAL INFECTIONS

(75) Inventors: David Haigh, Stevenage (GB); Charles David Hartley, Stevenage (GB); Peter David Howes, Stevenage (GB); Deborah Lynette Jackson, Clifton (GB); Pritom Shah, Stevenage (GB); Martin John Slater, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/531,884

(22) PCT Filed: Oct. 22, 2003

(86) PCT No.: PCT/EP03/11813

§ 371 (c)(1),
(2), (4) Date: Apr. 11, 2006

(87) PCT Pub. No.: WO2004/037818

PCT Pub. Date: May 6, 2004

(65) Prior Publication Data

US 2006/0258720 A1 Nov. 16, 2006

(30) Foreign Application Priority Data

Oct. 24, 2002 (GB) .................................. 0224774.0
Dec. 18, 2002 (GB) .................................. 0229470.0
Jul. 22, 2003 (GB) .................................. 0317141.0

(51) Int. Cl.
*A61K 31/4025* (2006.01)
*C07D 405/04* (2006.01)
*C07D 207/08* (2006.01)

(52) U.S. Cl. ...................... 514/422; 548/517; 548/518

(58) Field of Classification Search ................ 548/517, 548/202, 235, 518; 544/410; 546/279.1; 514/422

See application file for complete search history.

(56) References Cited

FOREIGN PATENT DOCUMENTS

| WO | 96/33170 A1 | 10/1996 |
| WO | 9929705 A2 | 6/1999 |
| WO | 99/37204 A1 | 7/1999 |
| WO | WO 99/54299 | 10/1999 |
| WO | WO 00/09543 | 2/2000 |
| WO | WO 01/85720 | 11/2001 |
| WO | 02/44168 A2 | 6/2002 |
| WO | 03037893 | 5/2003 |
| WO | 03037896 A1 | 5/2003 |
| WO | 2004037618 A1 | 6/2004 |

OTHER PUBLICATIONS

Ojima et al, 1991, Journal of Organometallic Chemistry, vol. 417(1-2), pp. 253-276.*
Chronic Hepatitis C: Current Disease Management, retrieved from Internet on Apr. 9, 2007, <http://digestive.niddk.nih.gov/ddiseases/pubs/chronichepc/index.htm>.*
Liang et al, Feb. 15, 2000, Annals of Internal Medicine, vol. 132(4), pp. 296-305.*
Syed, R.H., et al. "2,5-Disubstituted Pyrrolidines: Versatile Regioselective and Diastereoselective Synthesis by Enamine Reduction and Subsequent Alkylation." Organic & Biomolecular Chemistry, vol. 1, No. 11, May 28, 2003, pp. 1838-1841.
Sato et al.; Heterocycles: 1994: 37/1; 245-248.
P. De Caprariis G De Martino, E. Abignente, P Avara, L. Mayo: Pyrrolo[1,4]benzodiazepines. IV Synthesis of E. and Z-5.11-Dioxo-11a-ethoxycarbonyl-2-ethylidine-1,2,3,10.11, 11a-hexahydro-5Hyrrolo[2.1-o][1,4] benzodiezepine: J. Heterocyclic Chem.: Jan. 89; 26: 1023-1027.
Gardiner, James et al.; Synthesis and solid state conformation of phenylalanine mimetics constrained in a proline-like conformation; Organic & Biomolecular Chemistry; Jul. 27, 2004; 2(16); 2365-2370.
Ikeda M., et al.; Synthesis of tricyclic nitrogen-containing heterocycles by palladium-catalyzed cyclization of 2-alkenyl-n-(o-iodobenzoyl)- and 2-alkenyl-n-(o-iodophenylacetyl)-pyrroidines: Heterocycles: 1998; 42; pp. 155-158.
Confalone P.N., et al.; Design and synthesis of potential DNA cross-linking reagents based on the anthramycin class of minors groove binding compounds; J. Org. Chem.; 1988; 63: pp. 482-487.
Alig I., et al., Low molecular weight, non-peptide fibrinogen receptor antagonists: J. Med. Chem.; 1992; 35; pp. 4393-4407.
Padwa A., et al.; Transmutations of 1,3-dipoles: The conversion of a-diazo ketones into azomethine ylides via carbonyl ylides; J. Am. Chem. Soc.; 1992; 114; pp. 593-601.

(Continued)

*Primary Examiner*—Rebecca Anderson
*Assistant Examiner*—Karen Cheng
(74) *Attorney, Agent, or Firm*—Karen L. Prus

(57) ABSTRACT

Anti-viral agents of Formula (I)

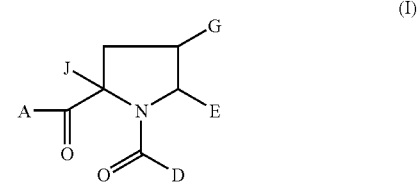

wherein:
A represents hydroxy; D represents aryl or heteroaryl; E represents hydrogen, $C_{1-6}$alkyl, aryl, heteroaryl or heterocyclyl; G represents hydrogen or optionally substituted $C_{1-6}$alkyl; J represents $C_{1-6}$alkyl, heterocyclylalkyl, arylalkyl or heteroarylalkyl; and salts, solvates and esters thereof; provided that when A is esterified to form —OR where R is selected from straight or branched chain alkyl, aralkyl, aryloxyalkyl, or aryl, then R is other than tert-butyl; processes for their preparation, pharmaceutical compositions comprising them, and methods of using them in HCV treatment are provided.

18 Claims, No Drawings

OTHER PUBLICATIONS

Culbertson T.P., et al.; Quinoione antibacterial agents substituted at the 7-position with aplinoamines. Synthesis and structure-activity relationships; J. Med. Chem.; 1990; 33, pp. 2270-2275.

Crooks, P.A., et al.; Synthesis of 5-hydroxy- and 5,6-dihydroxy-derivatives of spiro[indano-2-2'-pyrroiidine]. rigid analogues of tyramine and dopamine respectivity; Journal of the Chemical Society, Perkins Transactions 1; 1979; 11; pp. 2719-2726.

De Martino G., et al.; La Reazione Tra 2-Nitrobenzolaminomalonato Ed Aideide Acritica Per LA Sintesi Di Composti A Strutlura Parrolo[2,1-c][1,4]Benzodiazepinica (english summary only); Farmaco Ed Sc.; 1976; 31(11); pp. 786-790.

Ikeda et al.; Journal of the Chemical Society, Perkin Transactions 1: Organic and Bio-Organic Chemistry; 1997: 22; 3339-3344.

Sato et al., Journal of the Chemical Society, Perkin Transactions 1, 1995; 14; 1801-1809.

* cited by examiner

1-ACYL-PYRROLIDINE DERIVATIVES FOR THE TREATMENT OF VIRAL INFECTIONS

This application is filed pursuant to 35 U.S.C. §371 as a United States National Phase Application of International Application No. PCT/EP2003/011813 filed Oct. 22, 2003 which claims priority from GB 0224774.0 filed Oct. 24, 2002, GB 0229470.0 filed Dec. 18, 2002, and GB 0317141.0 filed Jul. 22, 2003

FIELD OF THE INVENTION

The present invention relates to novel acyl pyrrolidine derivatives useful as anti-viral agents. Specifically, the present invention involves novel HCV inhibitors.

BACKGROUND OF THE INVENTION

Ikeda et al, (1997) Journal of the Chemical Society, Perkin Transactions 1: Organic and Bio-Organic Chemistry 22: 3339-3344 and Sato et al, (1995) Journal of the Chemical Society, Perkin Transactions 1, 14:1801-1809 and Sato et al, (1994) Heterocycles 37(1): 245-248 disclose 4',5'-unsubstituted acyl pyrrolidine compounds useful as reagents in the regioselective synthesis of bridged azabicyclic compounds; no medical use was disclosed for the acyl pyrrolidine compounds.

Ikeda et al, (1996) Heterocycles 42(1): 155-158 and Confalone et al, (1988) Journal of Organic Chemistry 53(3): 482487 and De Martino et al, (1976) Farmaco, Ed. Sci. 31(11): 785-790 disclose 4',5'-unsubstituted acyl pyrrolidine compounds useful as reagents in the synthesis of tricyclic nitrogen-containing heterocycles; no medical use was disclosed for the acyl pyrrolidine compounds. Alig et al, (1992) Journal of Medicinal Chemistry 35(23): 4393-4407 discloses a 4',5'-unsubstituted acyl pyrrolidine compound useful as a reagent in the synthesis of non-peptide fibrinogen receptor antagonists; no medical use was disclosed for the acyl pyrrolidine compound.

Padwa et al, (1992) Journal of the American Chemical society 114(2): 593-601 discloses a 4',5'-unsubstituted acyl pyrrolidine compound useful as a reagent in the synthesis of azomethine ylides; no medical use was disclosed for the acyl pyrrolidine compound. Culbertson et al, (1990) Journal of Medicinal Chemistry 33(8): 2270-2275 and Crooks et al, (1979) Journal of the Chemical Society, Perkins Transactions 1, 11: 2719-2726 disclose 4',5'-unsubstituted acyl pyrrolidine compounds useful as reagents in the synthesis of 7-spiroamine quinolone and spiro[indan-2,2'-pyrrolidine] compounds respectively; no medical use was disclosed for the acyl pyrrolidine compounds.

WO2002/44168, WO96/33170 and EP505868A2 disclose 4',5'-unsubstituted acyl pyrrolidine compounds useful as intermediates in the synthesis of indolecarboxamide, N-aroylamino acid amide and N-acyl-α-amino acid derivatives respectively; no medical use was disclosed for the acyl pyrrolidine compounds.

De Caprariis et al, (1989) Journal of Heterocyclic Chemistry 26(4): 1023-1027 discloses 3 pyrrolidinedicarboxylic acid derivatives useful as intermediates in the synthesis of pyrrolo[1,4]benzodiazepine compounds; no medical use was disclosed for the pyrrolidinedicarboxylic acid derivatives.

WO99/37304 discloses oxoazaheterocyclyl derivatives, especially piperazinone compounds, having Factor Xa inhibitory activity. These derivatives may include certain acyl pyrrolidine derivatives. There is no mention of HCV polymerase inhibitory activity for the disclosed compounds.

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of those treated, 50-70% relapse within 6 months of cessation of treatment. Recently, with the introduction of pegylated interferon, both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), hepatitis C virus (HCV) is now widely accepted as the most common causative agent of post-transfusion non A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 14) and pestiviruses (e.g. bovine viral diarrhea virus, border disease virus, and classic swine fever virus) (Choo, Q-L et al (1989) Science 244:359-3; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA-A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215:744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

The NS5B protein (591 amino acids, 65 kDa) of HCV (Behrens, S. E. et al (1996) EMBO J. 15:12-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4), p. 2046-2051). Thus, inhibition of NS5B RdRp activity (inhibition of RNA replication) is predicted to cure HCV infection.

Based on the foregoing, there exists a significant need to identify synthetic or biological compounds for their ability to inhibit HCV.

SUMMARY OF THE INVENTION

The present invention involves acyl pyrrolidine compounds represented hereinbelow, pharmaceutical compositions comprising such compounds and use of the compounds in treating viral infection, especially HCV infection.

DETAILED DESCRIPTION OF THE INVENTION

The present invention provides compounds of Formula (I):

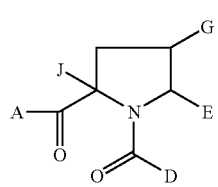
(I)

wherein:

A represents hydroxy;

D represents aryl or heteroaryl;

E represents hydrogen, $C_{1-6}$alkyl, aryl, heteroaryl or heterocyclyl;

G represents hydrogen or $C_{1-6}$alkyl optionally substituted by one or more substituents selected from halo, $OR^1$, $SR^1$, $C(O)NR^2R^3$, $CO_2H$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano, aryl, heteroaryl and heterocyclyl;

$R^1$ represents hydrogen, $C_{1-6}$alkyl, arylalkyl, or heteroarylalkyl;

$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;

$R^4$ is selected from the group consisting of $C_{1-6}$alkyl, aryl, heteroaryl, arylalkyl, and heteroarylalkyl;

$R^5$ and $R^6$ are independently selected from the group consisting of hydrogen, $C_{1-6}$alkyl, aryl, heteroaryl, arylalkyl, and heteroarylalkyl; or $R^5$ and $R^6$ together with the nitrogen atom to which they are attached form a 5 or 6 membered saturated cyclic group; and J represents $C_{1-6}$alkyl, heterocyclylalkyl, arylalkyl or heteroarylalkyl;

and salts, solvates and esters thereof; provided that when A is esterified to form —OR where R is selected from straight or branched chain alkyl, aralkyl, aryloxyalkyl, or aryl, then R is other than tert-butyl; for use in medical therapy.

There is provided as a further aspect of the present invention a compound of Formula (I) or a physiologically acceptable salt, solvate or ester thereof for use in human or veterinary medical therapy, particularly in the treatment or prophylaxis of viral infection, particularly HCV infection.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

According to another aspect of the invention, there is provided the use of a compound of Formula (I) or a physiologically acceptable salt, solvate or ester thereof in the manufacture of a medicament for the treatment and/or prophylaxis of viral infection, particularly HCV infection.

In a further or alternative aspect there is provided a method for the treatment of a human or animal subject with viral infection, particularly HCV infection, which method comprises administering to said human or animal subject an effective amount of a compound of Formula (I) or a physiologically acceptable salt, solvate or ester thereof.

In one aspect of the present invention, compounds of Formula (I) are represented by Formual (I'):

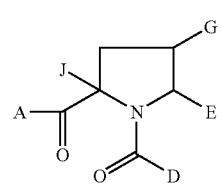
(I')

wherein:

A represents hydroxy;

D represents aryl or heteroaryl;

E represents hydrogen, $C_{1-6}$alkyl, aryl, heteroaryl or heterocyclyl;

G represents hydrogen or $C_{1-6}$alkyl optionally substituted by one or more substituents selected from halo, $OR^1$, $SR^1$, $C(O)NR^2R^3$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano and heterocyclyl;

$R^1$ represents hydrogen, $C_{1-6}$alkyl, arylalkyl, or heteroarylalkyl;

$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;

$R^4$ is selected from the group consisting of $C_{1-6}$alkyl, aryl, heteroaryl, arylalkyl, and heteroarylalkyl;

$R^5$ and $R^6$ are independently selected from the group consisting of hydrogen, $C_{1-6}$alkyl, aryl, heteroaryl, arylalkyl, and heteroarylalkyl; or $R^5$ and $R^6$ together with the nitrogen atom to which they are attached form a 5 or 6 membered saturated cyclic group; and J represents $C_{1-6}$alkyl, heterocyclylalkyl, arylalkyl or heteroarylalkyl;

and salts, solvates and esters thereof; provided that when A is esterified to form —OR where R is selected from straight or branched chain alkyl, aralkyl, aryloxyalkyl, or aryl, then R is other than tert-butyl.

The present invention further provides novel compounds of Formula (I), represented by Formula (Ia):

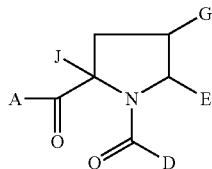

(Ia)

wherein:

A represents hydroxy;

D represents aryl or heteroaryl;

E represents hydrogen, $C_{1-6}$alkyl, aryl, heteroaryl or heterocyclyl;

G represents hydrogen or $C_{1-6}$alkyl optionally substituted by one or more substituents selected from halo, $OR^1$, $SR^1$, $C(O)NR^2R^3$, $CO_2H$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano, aryl, heteroaryl and heterocyclyl;

$R^1$ represents hydrogen, $C_{1-6}$alkyl, arylalkyl, or heteroarylalkyl;

$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;

$R^4$ is selected from the group consisting of $C_{1-6}$alkyl, aryl, heteroaryl, arylalkyl, and heteroarylalkyl;

$R^5$ and $R^6$ are independently selected from the group consisting of hydrogen, $C_{1-6}$alkyl, aryl, heteroaryl, arylalkyl, and heteroarylalkyl; or $R^5$ and $R^3$ together with the nitrogen atom to which they are attached form a 5 or 6 membered saturated cyclic group; and J represents $C_{1-6}$alkyl, heterocyclylalkyl, arylalkyl or heteroarylalkyl;

provided that i) E and G are not both hydrogen; and ii) the compound is other than 4-ethenyl-1-(2-nitrobenzoyl)-2,2-pyrrolidinedicarboxylic acid, diethyl ester;

1-(2-aminobenzoyl)-4-(1-hydroxyethyl)-2,2-pyrrolidinedicarboxylic acid, diethyl ester;

4-(1-hydroxyethyl)-1-(2-nitrobenzoyl)-2,2-pyrrolidinedicarboxylic acid, diethyl ester, and salts, solvates and esters thereof; provided that when A is esterified to form —OR where R is selected from straight or branched chain alkyl, aralkyl, aryloxyalkyl, or aryl, then R is other than tert-butyl.

In one aspect of the present invention, compounds of Formula (Ia) are represented by Formula (Ia'):

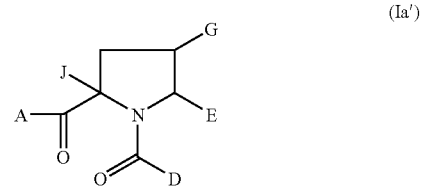

(Ia')

wherein:

A represents hydroxy;

D represents aryl or heteroaryl;

E represents hydrogen, $C_{1-6}$alkyl, aryl, heteroaryl or heterocyclyl;

G represents hydrogen or $C_{1-6}$alkyl optionally substituted by one or more substituents selected from halo, $OR^1$, $SR^1$, $C(O)NR^2R^3$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano and heterocyclyl;

$R^1$ represents hydrogen, $C_{1-6}$alkyl, arylalkyl, or heteroarylalkyl;

$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;

$R^4$ is selected from the group consisting of $C_{1-6}$alkyl, aryl, heteroaryl, arylalkyl, and heteroarylalkyl;

$R^5$ and $R^6$ are independently selected from the group consisting of hydrogen, $C_{1-6}$alkyl, aryl, heteroaryl, arylalkyl, and heteroarylalkyl; or $R^5$ and $R^6$ together with the nitrogen atom to which they are attached form a 5 or 6 membered saturated cyclic group; and J represents $C_{1-6}$alkyl, heterocyclylalkyl, arylalkyl or heteroarylalkyl;

provided that i) E and G are not both hydrogen; and ii) the compound is other than 4-ethenyl-1-(2-nitrobenzoyl)-2,2-pyrrolidinedicarboxylic acid, diethyl ester;

1-(2-aminobenzoyl)-4-(1-hydroxyethyl)-2,2-pyrrolidinedicarboxylic acid, diethyl ester;

4-(1-hydroxyethyl)-1-(2-nitrobenzoyl)-2,2-pyrrolidinedicarboxylic acid, diethyl ester;

and salts, solvates and esters thereof; provided that when A is esterified to form —OR where R is selected from straight or branched chain alkyl, aralkyl, aryloxyalkyl, or aryl, then R is other than tert-butyl.

It will be appreciated that the compounds of the present invention may contain one or more asymmetric carbon atoms and may exist in racemic, diastereoisomeric, and optically active forms. All of these racemic compounds, enantiomers and diastereoisomers are contemplated to be within the scope of the present invention.

In a preferred aspect, the relative stereochemistry of racemic compounds of Formula (I), and/or Formula (Ia) is represented by Formulae (Ip) or (Iq):

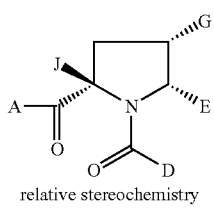
relative stereochemistry (Ip)

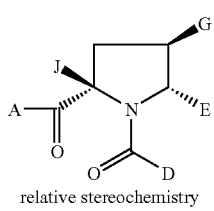
relative stereochemistry (Iq)

wherein A, D, E, G and J are as defined above for Formula (I) or (Ia).

In a more preferred aspect, the absolute stereochemistry of chiral compounds of Formula (I) and/or Formula (Ia) is represented by Formulae (Ipp) or (Iqq):

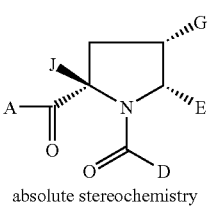
absolute stereochemistry (Ipp)

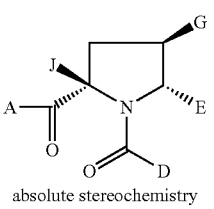
absolute stereochemistry (Iqq)

wherein A, D, E, G and J are as defined above for Formula (I) or (Ia).

The following substituent groups are preferred, where applicable, in respect of each of Formulae I, I', Ia, Ia' Ip, Ipp Iq and Iqq: Preferably, D represents optionally substituted phenyl; more preferably tert-butylphenyl optionally further substituted; especially preferred is para-tert-butylphenyl optionally further substituted, preferably meta-substituted, by halo, $C_{1-3}$alkyl or $C_{1-3}$alkoxy, especially bromo, chloro, methyl or methoxy; most preferably D is meta-methoxy-para-tert-butylphenyl (3-methoxy-4-tert-butylphenyl).

Preferably, E is selected from the group consisting of $C_{1-6}$alkyl, aryl and heteroaryl; more preferably E represents optionally substituted heteroaryl, preferably thiazolyl, pyridinyl, pyrazinyl, isoxazolyl and thienyl; especially preferred are pyridin-2-yl, 5-methylpyridin-2-yl, pyrazin-2-yl, 1,3-thiazol-2-yl, 5-methyl-1,3-thiazol-2-yl, 5-methoxymethyl-1,3-thiazol-2-yl, 2-chloro-1,3-thiazol-5-yl, 2-methoxy-1,3-thiazol-5-yl, 1,3-thiazol-4-yl, 5-methylisoxazol-3-yl, or thien-2-yl; most preferred is 1,3-thiazol-2-yl.

In another preferred aspect, E is selected from the group consisting of $C_{1-6}$alkyl, aryl and heteroaryl; more preferably E represents heteroaryl, preferably thiazolyl, pyridinyl and pyrazinyl; especially preferred are pyridin-2-yl, pyrazin-2-yl, 1,3-thiazol-2-yl, 5-methyl-1,3-thiazol-2-yl, 2-chloro-1,3-thiazol-5-yl, 2-methoxy-1,3-thiazol-5-yl or 1,3-thiazol-4-yl; most preferred is 1,3-thiazol-2-yl.

Preferably, G represents $C_{1-6}$-alkyl optionally substituted by halo, $OR^1$, $SR^1$, $SO_2R^4$ and cyano; more preferably G represents $C_{1-6}$alkyl optionally substituted by $OR^1$; especially preferably, G represents methyl optionally substituted by $OR^1$.

Preferably, $R^1$ represents hydrogen or $C_{1-6}$alkyl; more preferably, $R^1$ represents hydrogen, methyl, ethyl, propyl or prop-2-enyl, especially methyl or ethyl.

Preferably, $R^4$ represents $C_{1-6}$alkyl; more preferably, $R^4$ represents methyl, ethyl, or propyl, especially methyl or ethyl.

Preferably, J represents $C_{1-6}$alkyl, arylalkyl or heteroarylalkyl; more preferably isobutyl, prop-2-enyl, benzyl or pyridylmethyl, especially isobutyl.

In one aspect of the present invention, when D is phenyl substituted by at least two substituents independently selected from hydroxy, alkoxy, —$CO_2H$, —$CO_2R^4$, or fluoro; G is hydrogen or $C_{1-6}$alkyl; and J is $C_{1-6}$alkyl; then E is aryl, heteroaryl or heterocyclyl.

It is to be understood that the present invention covers all combinations of suitable, convenient and preferred groups described herein.

As used herein unless otherwise specified, "alkyl" refers to an optionally substituted hydrocarbon group. The alkyl hydrocarbon group may be linear, branched or cyclic, saturated or unsaturated. Where the alkyl hydrocarbon group is cyclic, it will be understood that there will be a minimum of 3 carbon atoms in the group. Where the alkyl hydrocarbon group is unsaturated, it will be understood that there will be a minimum of 2 carbon atoms in the group and that the group may be, for example, an alkenyl or alkynyl group. Preferably, the group is saturated. Preferred alkyl moieties are $C_{1-6}$-alkyl, more preferably $C_{1-4}$alkyl. Unless otherwise stated, optional substituents include $C_{1-6}$alkyl, halo, $OR^1$, $SR^1$, $C(O)NR^2R^3$, $C(O)R^4$, $CO_2H$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano, oxo, and heterocyclyl.

As used herein, "alkoxy" (when used as a group or as part of a group) refers to an alkyl ether radical, wherein the term "alkyl" is defined above. Examples of alkoxy as used herein include, but are not limited to; methoxy, ethoxy, n-propoxy, i-propoxy and the like.

As used herein, "aryl" refers to an optionally substituted aromatic group with at least one ring having a conjugated pi-electron system, containing up to two conjugated or fused ring systems. "Aryl" includes carbocyclic aryl and biaryl groups, all of which may be optionally substituted, for example phenyl, naphthyl or bi-phenyl. Preferred "aryl" moieties are unsubstituted, monosubstituted, disubstituted or trisubstituted phenyl. Preferred "aryl" substituents are selected from the group consisting of $C_{1-6}$alkyl, halo, $OR^1$, $C(O)NR^2R^3$, $C(O)R^4$, $CO_2H$, $CO_2R^4$, $NR^2R^3$, $NHC(O)R^4$, NHCO$_2$R$^4$, NHC(O)NR$^5$R$^6$, SO$_2$NR$^5$R$^6$, SO$_2$R$^4$, nitro, cyano, oxo, heterocyclyl, CF$_3$, and NO$_2$.

As used herein, "heteroaryl" refers to an optionally substituted, 5 or 6 membered, aromatic group comprising one to four heteroatoms selected from N, O and S, with at least one ring having a conjugated pi-electron system, containing up to two conjugated or fused ring systems. Preferred "heteroaryl" moieties are unsubstituted, monosubstituted, disubstituted or trisubstituted pyridyl and thiazolyl. Preferred "heteroaryl" substituents are selected from the group consisting of C$_{1-6}$alkyl, halo, OR$^1$, C(O)NR$^2$R$^3$, C(O)R$^4$, CO$_2$H, CO$_2$R$^4$, NR$^2$R$^3$, NHC(O)R$^4$, NHCO$_2$R$^4$, NHC(O)NR$^5$R$^6$, SO$_2$NR$^5$R$^6$, SO$_2$R$^4$, nitro, cyano, oxo, heterocyclyl, CF$_3$, and NO$_2$.

As used herein, "heterocyclic" and "heterocyclyl" refer to an optionally substituted, 5 or 6 membered, saturated cyclic hydrocarbon group containing 1 or 2 heteroatoms selected from N, optionally substituted by hydrogen, C$_{1-6}$alkyl, C(O) R$^4$, SO$_2$R$^4$, aryl or heteroaryl; O; and S, optionally substituted by one or two oxygen atoms.

Preferred compounds of Formula (I) useful in the present invention are selected from the group consisting of:

rel-(2S,4R,5R)-2-Isobutyl-1-(3-methoxy-4-tert-butylbenzoyl)-4-ethoxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methoxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-fluoromethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methyl-5-(1,3-thiazol-2-yl)pyrrolidine-2-carboxylic acid;

2-Allyl-1-(3-bromo-4-tert-butylbenzoyl)-pyrrolidine-2-carboxylic acid;

2-Benzyl-1-(3-bromo-4-tert-butylbenzoyl)-pyrrolidine-2-carboxylic acid;

rel-(2S,4R,5R)-2-Isobutyl-1-(3-methoxy-4-tert-butylbenzoyl)-4-hydroxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-allyloxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-propyloxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-ethoxymethyl-5(1,3thiazol-2-yl)pyrrolidine-2-carboxylic acid;

rel-(2S,4S,5R)-2-Isobutyl-1-(3-methoxy-4-tert-butylbenzoyl)-4-isopropenyl-5-(1,3-thiazol-2-yl)pyrrolidine-2-carboxylic acid;

rel-(2S,4S,5R)-2-Isobutyl-1-(3-methoxy-4-tert-butylbenzoyl)-4-isopropyl-5-(1,3-thiazol-2-yl)pyrrolidine-2-carboxylic acid;

(2S,4S,5R)-2-Isobutyl-1-(3-methyl-4-tert-butylbenzoyl)-4-methoxymethyl-5-(1,3-thiazol-2-yl)pyrrolidine-2-carboxylic acid;

(2S,4S,5R)-2-Isobutyl-1-(3-methyl-4-tert-butylbenzoyl)-4-ethoxymethyl-5-(1,3-thiazol-2-yl)pyrrolidine-2-carboxylic acid;

rel-(2R,4R,5R)-2-Benzyl-1-(3-methoxy-4-tert-butylbenzoyl)-4-ethoxymethyl-5-(1,3-thiazol-2-yl)-pyrrolidine-2-carboxylic acid;

(2S,4S,5R,)-2-Isobutyl-1-(3-chloro-4-tert-butylbenzoyl)-4-ethoxymethyl-5-(1,3-thiazol-2-yl)-pyrrolidine-2-carboxylic acid;

(2S,4S,5R,)-2-Isobutyl-1-(3-methyl-4-tert-butylbenzoyl)-4-ethoxymethyl-5-(1,3-thiazol-2-yl)-pyrrolidine-2-carboxylic acid;

rel-(2R,4R,5R)-2-Benzyl-1-(3-methoxy-4-tert-butylbenzoyl)-4-ethoxymethyl-5-(1,3-thiazol-2-yl)-pyrrolidine-2-carboxylic acid;

rel-(2S,4S,5R)-2-isobutyl-1-(3-methoxy-4-tert-butylbenzoyl)-4-methoxymethyl-5-(pyrazin-2-yl)pyrrolidine-2-carboxylic acid;

rel-(2S,4R,5R)-2-Isobutyl-1-(3-methoxy-4-tert-butylbenzoyl)-4-methoxymethyl-5-(pyrazin-2-yl)pyrrolidine-2-carboxylic acid;

rel-(2S,4S,5R)-2-Isobutyl-1-(3-methoxy-4-tert-butylbenzoyl)-4-methoxymethyl-5-(5methyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(2-chloro-1,3-thiazol-5-yl)pyrrolidine-2-carboxylic acid;

rel-(2S,4S,5R)-2-Isobutyl-1-(3-methoxy-4-tert-butylbenzoyl)-4-methoxymethyl-5-(2-methoxy-1,3-thiazol-5-yl)pyrrolidine-2-carboxylic acid;

rel-(2S,4R,5R)-2-isobutyl-1-(3-methoxy-4-tert-butylbenzoyl)-4-((methylthio)methyl)-5-5-(1,3-thiazol-2-yl)pyrrolidine-2-carboxylic acid;

rel-(2S,4R,5R)-2-Isobutyl-1-(3-methoxy-4-tert-butylbenzoyl)-4-((methanesulfonyl)methyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-(1,1-difluoroethyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

rel-(2R,4S,5R)-2-Benzyl-1-(3-methoxy-4-tert-butylbenzoyl)-4-methoxymethyl-5-(1,3-thiazol-2-yl)-pyrrolidine-2-carboxylic acid;

rel-(2R,4S,5R)-2-Benzyl-1-(3-methoxy-4-tert-butylbenzoyl)-4-ethoxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(pyridin-2-yl)pyrrolidine-2-carboxylic acid;

(2S,4R,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

(2S,4R,5R)-2-Isobutyl-1-(3-methoxy-4-tert-butylbenzoyl)-4-(1-hydroxyethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-ethoxymethyl-5-(1,3-thiazol-4-yl)pyrrolidine-2-carboxylic acid;

rel-(2S,4S,5R)-2-Isobutyl-1-(3-methoxy-4-tert-butylbenzoyl)-allyloxymethyl-5-(1,3-thiazol-2-yl)pyrrolidine-2-carboxylic acid;

rel-(2S,4S,5R>2-Isobutyl-1-(3-methoxy-4-tert-butylbenzoyl)-4-propyloxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-cyanomethyl-5-(1,3-thiazol-2-yl)pyrrolidine-2-carboxylic acid;

(2S,4S,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-ethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methoxymethyl-5-(pyridin-2-yl)pyrrolidine-2-carboxylic acid;

rel-(2S,4R,5R)-2-Isobutyl-1-(3-methoxy-4-tert-butylbenzoyl)-4-(1-methoxyethyl)-5-(pyridin-2-thiazol-2-yl)pyrrolidine-2-carboxylic acid;

(2S,4S,5R)-2-Isobutyl-1-(3-methoxy-4-tert-butylbenzoyl)-4-methoxy-methyl-5-(pyridin-2-yl)pyrrolidine-2-carboxylic acid;

rel-(2S,4S,5R)-2-Isobutyl-1-(3-methoxy-4-tert-butylbenzoyl)-4-ethoxymethyl-5-(5-methylisoxazol-3-yl)pyrrolidine-2-carboxylic acid;

rel-(2S,4S,5R)-2-Isobutyl-1-(3-methoxy-4-tert-butylbenzoyl)-4-methoxymethyl-5-(5-methoxymethyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(5-methylpyridin-2-yl)pyrrolidine-2-carboxylic acid;

rel-(2S,4S,5R)-2-Isobutyl-1-(3-methoxy-4-tert-butylbenzoyl)-4-methoxymethyl-5-(thien-2-yl)pyrrolidine-2-carboxylic acid;

and salts, solvates and esters, and individual enantiomers thereof where appropriate.

Preferred compounds of Formula (Ia) are selected from the group consisting of:

rel-(2S,4R,5R)-2-Isobutyl-1-(3-methoxy-4-tert-butylbenzoyl)-4-ethoxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methoxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-fluoromethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methyl-5-(1,3-thiazol-2-yl)pyrrolidine-2-carboxylic acid;

rel-(2S,4R,5R)-2-Isobutyl-1-(3-methoxy-4-tert-butylbenzoyl)-4-hydroxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-allyloxymethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-propyloxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-isopropenyl-5-(1,3thiazol-2-yl)pyrrolidine-2-carboxylic acid;

rel-(2S,4S,5R)-2-Isobutyl-1-(3-methoxy-4-tert-butylbenzoyl)-4-isopropyl-5-(1,3-thiazol-2-yl)pyrrolidine-2-carboxylic acid;

(2S,4S,5R)-2-Isobutyl-1-(3-methoxy-4-tert-butylbenzoyl)-4-methoxymethyl-5-(1,3-thiazol-2-yl)pyrrolidine-2-carboxylic acid;

(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid;

(2S,4S,5R)-2-Isobutyl-1-(3-bromo-4-tert-butylbenzoyl)-4-ethoxymethyl-5-(1,3-thiazol-2-yl)-pyrrolidine-2-carboxylic acid;

(2S,4S,5R)-2-Isobutyl-1-(3-chloro-4-tert-butylbenzoyl)-4-ethoxymethyl-5-(1,3-thiazol-2-yl)-pyrrolidone-2-carboxylic acid;

(2S,4S,5R)-2-Isobutyl-1-(3-methyl-4-tert-butylbenzoyl)-4-ethoxymethyl-5-(1,3-thiazol-2-yl)pyrrolidine-2-carboxylic acid;

rel-(2R,4R,5R)-2-Benzyl-1-(3-methoxy-4-tert-butylbenzoyl)-4-methoxymethyl-5-(1,3-thiazol-2-yl)pyrrolidine-2-carboxylic acid;

rel-(2R,4R,5R)-2-Benzyl-1-(3-methoxy-4-tert-butylbenzoyl)-4-ethoxymethyl-5-(1,3-thiazol-2-yl)-pyrrolidine-2-carboxylic acid;

rel-(2S,4S,5R)-2-Isobutyl-1-(3-methoxy-4-tert-butylbenzoyl)-4-methoxymethyl-5-(pyrazin-2-yl)pyrrolidine-2-carboxylic acid;

rel-(2S,4R,5R)-2-Isobutyl-1-(3-methoxy-4-tert-butylbenzoyl)-4-methoxymethyl-5-(pyrazin-2-yl)pyrrolidine-2-carboxylic acid;

rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(2-chloro-1,3-thiazol-5-yl)pyrrolidine-2-carboxylic acid;

rel-(2S,4S,5R)-2-Isobutyl-1-(3-methoxy-4-tert-butylbenzoyl)-4-methoxymethyl-5-(2-methoxy-1,3-thiazol-5-yl)pyrrolidine-2-carboxylic acid;

rel-(2S,4R,5R)-2-Isobutyl-1-(3-methoxy-4-tert-butylbenzoyl)-4-((methylthio)methyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-((methanesulfonyl)methyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-(1,1-difluoroethyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

rel-(2R,4S,5R)-2-Benzyl-1-(3-methoxy-4-tert-butylbenzoyl)-4-methoxymethyl-5-(1,3-thiazol-2-yl)-pyrrolidine-2-carboxylic acid;

rel-(2R,4S,5R)-2-Benzyl-1-(3-methoxy-4-tert-butylbenzoyl)-4-ethoxymethyl-5-(1,3thiazol-2-yl)-pyrrolidine-2-carboxylic acid;

rel-(2S,4S,5R)-2-isobutyl-1-(3-methoxy-4-tert-butylbenzoyl)-4-methoxymethyl-5-(pyridin-2-yl)pyrrolidine-2-carboxylic acid;
(2S,4R,5R)-2-Isobutyl-1-(3-methoxy-4-tert-butylbenzoyl)-4(1-hydroxy-1-methylethyl)-5-(1,3-thiazol-2-yl)pyrrolidine-2-carboxylic acid;
(2S,4R,5R)-2-Isobutyl-1-(3-methoxy-4-tert-butylbenzoyl)-4(1-hydroxyethyl)-5-(1,3-thiazol-2-yl)pyrrolidine-2-carboxylic acid;
rel-(2S,4S,5R)-2-Isobutyl-1-(3-methoxy-4-tert-butylbenzoyl)-4-ethoxymethyl-5-(1,3thiazol-4-yl)pyrrolidine-2-carboxylic acid;
re-(2S,4S,5R)-2-Isobutyl-1-(3-methoxy-4-tert-butylbenzoyl)-4-allyloxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-propyloxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-cyanomethyl-5-(1,3-thiazol-2-yl)pyrrolidine-2-carboxylic acid;
(2S,4S,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;
rel-(2S,4R,5R)-2-Isobutyl-1-(3-methoxy-4-tert-butylbenzoyl)-4-ethyl-5-(1,3-thiazol-2-yl)pyrrolidine-2-carboxylic acid;
rel-(2S,4R,5R)-2-Isobutyl-1-(3-methoxy tert-butylbenzoyl)-4-methoxymethyl-5-(pyridin-2-yl))-pyrrolidine-2-carboxylic acid;
rel(2S,4R,5R)-2-Isobutyl-1-(3-methoxy-4-tert-butylbenzoyl)-4-(1-methoxyethyl)-5-(1,3-thiazol-2-yl)pyrrolidine-2-carboxylic acid;
(2S,4S,5R)-2-Isobutyl-1-(3-methoxy-4-tert-butylbenzoyl)-4-methoxymethyl-5-(pyridin-2-yl)pyrrolidine-2-carboxylic acid;
rel-(2S,4S,5R)-2-Isobutyl-1-(3-methoxy-4-tert-butylbenzoyl)-4-ethoxymethyl-5-(5-methylisoxazol-3-yl)pyrrolidine-2-carboxylic acid;
rel-(2S,4S,5R)-2-Isobutyl-1-(3-methoxy-4-tert-butylbenzoyl)-4-methoxymethyl-5-(5-methoxymethyl-1,3-thiazol-2-yl)pyrrolidine-2-carboxylic acid;
rel-(2S,4S,5R)-2-Isobutyl-1-(3-methoxy-4-tert-butylbenzoyl)-4-methoxymethyl-5-(5-methylpyridin-2-yl)pyrrolidine-2-carboxylic acid;
rel-(2S,4S,5R)-2-Isobutyl-1-(3-methoxy-4-tert-butylbenzoyl)-4-methoxymethyl-5-(thien-2-yl)pyrrolidine-2-carboxylic acid;

and salts, solvates and esters, and individual enantiomers thereof where appropriate.

In a preferred aspect, the present invention provides compounds of Formula (I) and/or (Ia) selected from the group consisting of Examples 1 to 45 hereinafter defined, and salts, solvates and esters, and where appropriate, individual enantiomers thereof. In a further preferred aspect, the present invention provides compounds of Formula (I) selected from the group consisting of Examples 1 to 16 hereinafter defined, and salts, solvates and esters, and where appropriate, individual enantiomers thereof. In a further preferred aspect, the present invention provides compounds of Formula (I) selected from the group consisting of Examples 1 to 14 hereinafter defined, and salts, solvates and esters, and where appropriate, individual enantiomers thereof.

Also included in the present invention are pharmaceutically acceptable salt complexes. The present invention also covers the physiologically acceptable salts of the compounds of formula (I). Suitable physiologically acceptable salts of the compounds of formula (I) include acid salts, for example sodium, potassium, calcium, magnesium and tetraalkylammonium and the like, or mono- or di-basic salts with the appropriate acid for example organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids and the like.

The present invention also relates to solvates of the compounds of Formula (I), for example hydrates.

The present invention also relates to pharmaceutically acceptable esters of the compounds of Formula (I) and (Ia), for example carboxylic acid esters —COOR, in which R is selected from straight or branched chain alkyl, for example n-propyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$alkyl or $C_{1-4}$alkoxy or amino). Unless otherwise specified, any alkyl moiety present in such esters preferably contains 1 to 18 carbon atoms, particularly 1 to 4 carbon atoms. Any aryl moiety present in such esters preferably comprises a phenyl group.

Preferably, the present invention relates to compounds of Formula (I) and (Ia) and salts and solvates thereof.

It will further be appreciated that certain compounds of the present invention may exist in different tautomeric forms. All tautomers are contemplated to be within the scope of the present invention.

Compounds of Formula (I) and (Ia) in which A is hydroxy may be prepared from a compound of Formula (II)

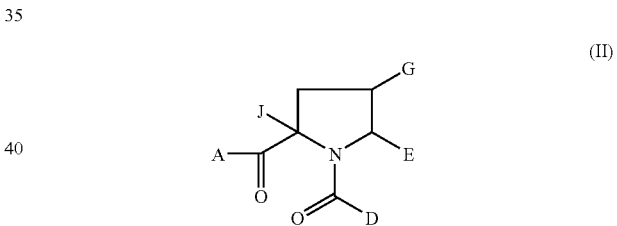

in which A is a protected hydroxy group, for example an alkoxy, benzyloxy or silyloxy, for example tri-($C_{1-4}$alkyl)-silyloxy group, and D, E, G and J are as defined above for Formula (I) or (Ia), by deprotection. Suitable protecting groups can be found, but are not restricted to, those found in T W Greene and P G M Wuts 'Protective Groups in Organic Synthesis', $3^{rd}$ Ed (1999), J Wiley and Sons.

For example when A is tert-butoxy, and D, E, G and J are as defined above for Formula (I), by treatment with an appropriate acid, for example trifluoroacetic acid. Suitably, the reaction is carried out in a solvent, for example dichloromethane. Preferably, the temperature is in the range 0 to 50° C., more preferably 20 to 30° C.

For example when A is benzyloxy, and D, E, G and J are as defined above for Formula (I), by hydrogenolysis in the presence of a suitable catalyst for example palladium-on-carbon. Suitably, the reaction is carried out in a solvent, for example ethanol. Preferably, the temperature is in the range 0 to 50° C.

For example when A is allyloxy, and D, E, G and J are as defined above for Formula (I), by treatment with a suitable catalyst for example tetrakis(triphenylphosphine)palladium (0) and a suitable proton source, for example phenylsilane. The reaction is carried out in a suitable solvent, for example dichloromethane.

For example when A is tri(methyl)silyloxy, and D, E, G and J are as defined above for Formula (I), by treatment with a suitable fluoride source for example tetrabutylammonium fluoride. The reaction is carried out in a suitable solvent, for example tetrahydrofuran.

Compounds of Formula (I) and (Ia) in which A is hydroxy or a protected form thereof may also be prepared by reaction of a compound of Formula (III)

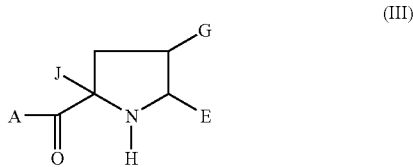

(III)

in which A, E, G, and J are as defined above for Formula (I); with a suitable acylating agent, for example D—C(O)-hal, wherein hal is a halo atom, preferably chloro or bromo, and D is as defined above for Formula (I). Preferably the reaction is carried out in a suitable solvent, for example dichloromethane, in the presence of a suitable base, for example triethylamine and thereafter removing any protecting group. Suitable protecting groups can be found, but are not restricted to, those found in T W Greene and P G M Wuts 'Protective Groups in Organic Synthesis', 3$^{rd}$ Ed (1999), J Wiley and Sons.

Compounds of Formula (I) or (II) in which G represents optionally substituted alkyl, may be prepared by appropriate manipulation of a compound of Formula (IIa)

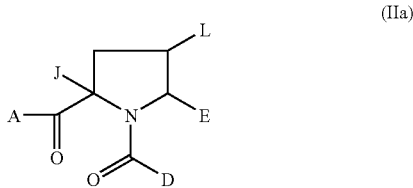

(IIa)

in which A is hydroxy or an alkoxy, benzyloxy or tri-($C_{1-4}$alkyl)-silyloxy group, D, E and J are as defined above for Formula (I), and L represents $CO_2Y$ or COY wherein Y represents hydrogen or alkyl.

For example, a compound of Formula (II) in which G represents hydroxyalkyl may be prepared by reduction of a compound of Formula (IIa) in which L represents $CO_2Y$ or COY and Y represents hydrogen or alkyl, using a suitable reducing agent, for example lithium borohydride, sodium borohydride, sodium triacetoxyborohydride, borane/dimethyl sulfide complex or lithium aluminium hydride, or suitable combinations thereof, in a suitable solvent or mixture thereof for example tetrahydrofuran or methanol.

For example, a compound of formula (II) in which G represents hydroxyalkyl may also be prepared by reaction of a compound of formula (IIa) in which L represents $CO_2Y$ or COY and Y represents hydrogen or alkyl, with a suitable organometallic reagent, for example methylmagnesium bromide or methyl lithium, in a suitable solvent, for example tetrahydrofuran.

For example, a compound of formula (II) in which G represents difluoroalkyl may be prepared by reaction of a compound of formula (IIa) in which L represents COY and Y represents alkyl, with a suitable fluorinating agent, for example diethylaminosulfur trifluoride, in a suitable solvent, for example dichloromethane.

For example, a compound of Formula (II) in which G represents alkenyl may be prepared by treatment of a compound of formula (IIa) in which L represents COY and Y represents hydrogen or alkyl, with a phosphonium salt, for example phosphonium halide salts such as methyltriphenylphosphonium bromide, methyltriphenylphosphonium chloride, methoxymethyltriphenylphosphonium bromide or methoxymethyltriphenylphosphonium chloride, in the presence of a base, for example lithium bis(trimethylsilyl)amide, and in a suitable solvent, for example tetrahydrofuran.

In a further aspect, a compound of Formula (II) may be prepared by appropriate manipulation of another compound of Formula (II). For example, a compound of Formula (II) in which G represents hydroxyalkyl may be converted into a compound of Formula (II) in which G represents optionally substituted alkyl, for example alkyl, haloalkyl or alkoxyalkyl.

For example, a compound of Formula (II) in which G represents alkoxyalkyl may be prepared by alkylation of a compound of formula (II) in which G represents hydroxyalkyl using a suitable base for example sodium hydride and a suitable alkylating agent such as an alkyl iodide, for example methylating using methyl iodide or ethylating using ethyl iodide. Preferably the reaction is carried out in a suitable solvent, for example dimethylformamide.

For example, a compound of Formula (II) in which G represents haloalkyl may be prepared by halogenation of a compound of Formula (II) in which G represents hydroxyalkyl using a suitable halogenating agent, for example hydroxymethyl may be converted into fluoromethyl using a suitable fluorinating agent, for example diethylaminosulfur trifluoride, in a suitable solvent, for example dichloromethane.

For example, a compound of Formula (II) in which G represents cyanomethyl may be prepared by reacting a compound of Formula (II) in which G represents hydroxymethyl with, for example trifluoromethanesulfonic anhydride, and subsequently treating the product with a nucleophile, for example a cyanide salt such as tetrabutylammonium cyanide. A compound of Formula (II) in which G represents $C_{1-4}$alkylthiomethyl can similarly be prepared using $C_{1-4}$alkylthiolate as the nucleophile.

For example, a compound of Formula (II) in which G represents $C_{1-4}$alkylsulfonylmethyl may be prepared by oxidising a compound of Formula (II) in which G represents $C_{1-4}$alkylthiomethyl, using for example 3-chloroperbenzoic acid, in a suitable solvent, for example dichloromethane.

For example, a compound of Formula (II) in which G represents alkyl may be prepared by deoxygenation of a compound of formula (II) in which G represents hydroxyalkyl. The deoxygenation is suitably carried out in a two step process in which:

Step (i) A compound of formula (II) in which G represents hydroxyalkyl is converted into a thionocarbonate by treatment with a suitable chloroformate for example 4-fluorophenyl thionochloroformate. Preferably the reaction is carried out in a suitable solvent, for example dichloromethane, in the presence of a suitable base catalyst, for example 4-(N, N-dimethylamino)pyridine. Step (ii) The thionocarbonate from step (i) is treated with a suitable radical initiator, for example AIBN, and a suitable proton source, such as tris (trimethylsilyl)silane, in a suitable solvent, for example dioxan. Preferably, the temperature is in the range 80 to 120° C.

For example, a compound of Formula (II) in which G represents an unsaturated alkyl group, for example 1-methylethenyl or 2-methoxyethenyl, may be converted into a compound of Formula (II) in which G represents a saturated alkyl group, for example isopropyl or 2-methoxyethyl, by hydrogenation in the presence of a suitable catalyst, for example palladium-on-carbon, and in a suitable solvent, for example ethanol.

For example, a compound of Formula (II) in which G represents alkenyloxyalkyl or substituted alkenyloxyalkyl may be converted into a compound of Formula (II) in which G represents alkyloxyalkyl or substituted alkyloxyalkyl by hydrogenation in the presence of a suitable catalyst, for example palladium-on-carbon, and in a suitable solvent, for example ethanol. For example, allyloxyalkyl or substituted allyloxyalkyl may be converted into propyloxyalkyl or substituted propyloxyalkyl.

For example, a compound of Formula (II) in which E represents 2-chloro-1,3-thiazol-5-yl may be converted into a compound of Formula (II) in which E represents 2-alkoxy-1,3-thiazol-5-yl by heating with a suitable base, for example sodium hydroxide, and a suitable source of alkoxide, for example 2-methoxy-1,3-thiazol-5-yl may be prepared using sodium hydroxide and methanol.

A compound of Formula (IIa) in which L represents $CO_2Y$ wherein Y represents hydrogen may be prepared from a compound of Formula (IIa) in which L represents $CO_2Y$ wherein Y represents alkyl. For example, a compound of Formula (IIa) in which L represents $CO_2Me$ may be converted into a compound of Formula (IIa) in which L represents $CO_2H$ by hydrolysis, for example base catalysed hydrolysis using a suitable base such as sodium methoxide in a suitable solvent such as methanol.

A compound of Formula (IIa) in which L represents $CO_2Y$ or COY wherein Y represents hydrogen or alkyl may be prepared from a compound of Formula (IIIa)

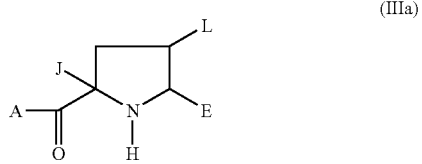

in which L represents $CO_2Y$ or COY wherein Y represents hydrogen or alkyl, and A, E, and J are as defined above for Formula (I); with a suitable acylating agent, for example D—C(O)-hal, wherein hal is a halo atom, preferably chloro or bromo, and D is as defined above for Formula (I). Preferably the reaction is carried out in a suitable solvent, for example dichloromethane, in the presence of a suitable base, for example triethylamine.

In a further aspect, a compound of Formula (IIa) in which L represents COY and Y represents hydrogen may be prepared in a two-stage process from a compound of Formula (IIa) in which L represents $CO_2Y$ and Y represents hydrogen or alkyl. In a first step, the compound of Formula (IIa) in which L represents $CO_2Y$ and Y represents hydrogen or alkyl is treated with a suitable reducing agent, for example lithium aluminium hydride or sodium borohydride. In a second step, the resultant hydroxy group is oxidised with a suitable oxidising agent which may be selected from conventional oxidising reagents known in the art, for example an appropriate mixture of oxalyl chloride, dimethyl sulphoxide and triethylamine.

A compound of Formula (IIa) in which A is hydroxy, may be converted to a compound of Formula (IIa) in which A is an alkoxy, benzyloxy or silyloxy group by standard hydroxy protecting techniques. Similarly, a compound of Formula (IIa) in which A is an alkoxy, benzyloxy or silyloxy group, may be converted to a compound of Formula (IIa) in which A is hydroxy by standard deprotecting techniques. Suitable protecting groups can be found, but are not restricted to, those found in T W Greene and P G M Wuts 'Protective Groups in Organic Synthesis', 3$^{rd}$ Ed (1999), J Wiley and Sons.

A compound of Formula (IIIa) may be prepared by reaction of a compound of Formula (IV)

in which E and J are as defined above for Formula (I) and A is as defined above for Formula (II) with a compound of Formula (V)

wherein L represents $CO_2Y$ or COY wherein Y represents hydrogen or alkyl. Preferably, the reaction is carried out in a suitable solvent, for example THF or acetonitrile, optionally in the presence of a Lewis acid catalyst, such as lithium bromide or silver acetate, and a base, such as triethylamine, 1,8-diazabicyclo[5,4,0]undec-7-ene (DBU) or tetramethyl guanidine. Alternatively, the reaction is carried out in a suitable solvent, for example THF or acetonitrile, in the presence of an acid, such as acetic acid, or the reaction may be carried out by heating compounds of Formula (IV) and Formula (V) in a suitable solvent, for example toluene, xylene or acetonitrile in the absence of a catalyst.

Compounds of Formula (III) in which G represents optionally substituted alkyl may be prepared by appropriate manipulation of a compound of Formula (IIIa) after first protecting the N-atom of the pyrrolidine ring with a suitable N-protecting group, for example benzyloxycarbonyl (CBZ) or t-butoxycarbonyl. For example, a compound of Formula (III) in which G represents hydroxyalkyl may be prepared by reduction of a compound of Formula (IIIa) in which L represents $CO_2Y$ and Y represents alkyl, using a suitable reducing agent, for example lithium borohydride or sodium borohydride, in a suitable solvent for example tetrahydrofuran. Deprotection of the N-atom by standard procedures results in the compound of Formula (III). For example, when the N-protecting group is CBZ, deprotection may be achieved by catalytic hydrogenolysis. For example, when the N-protecting group is t-butoxycarbonyl, deprotection may be achieved by treatment with a suitable acid, for example trifluoroacetic acid.

In a similar manner to that described above in relation to compounds of Formula (II), a compound of Formula (III), in which G represents hydroxyalkyl and the N-atom is protected, may be converted into a compound of Formula (III) in which G represents optionally substituted alkyl, for example alkyl, haloalkyl or alkoxyalkyl and the N-atom is protected. Deprotection of the N-atom by standard procedures results in the new compound of Formula (III).

Compounds of Formula (IV) May be prepared by reaction of a compound of Formula (VI)

(VI)

in which J is as defined above for Formula (I) and A is as defined above for Formula (II) with a compound of Formula E-CHO in the presence of a suitable base, for example triethylamine, in a suitable solvent, for example dichloromethane.

Compounds of Formula (VI) and E-CHO are known in the art or may be prepared by standard literature procedures.

Compounds of Formula (I) in which A is an ester may be prepared by esterification of a compound of Formula (I) in which A is hydroxy by standard literature procedures for esterification.

It will be appreciated that compounds of Formula (I), (Ia), (II), (IIa), (III) and/or (IIIa) which exist as diastereoisomers may optionally be separated by techniques well known in the art, for example by column chromatography.

It will also be appreciated that the present invention provides a method for the interconversion of C(4)-epimers of a compound of formula (IIa) or (IIIa) in which L represents $CO_2Y$ or COY wherein Y represents hydrogen or alkyl, and A, E, and J are as defined above for formula (I). For example the rel-(2S,4S,5R)-diastereoisomer of a compound of formula (IIa) and/or (IIIa) may be converted into the rel-(2S,4R,5R)-diastereoisomer and, similarly, the rel-(2R,4S,5R)-diastereoisomer of a compound of formula (IIa) and/or (IIIa) may be converted into the rel-(2R,4R,5R)-diastereoisomer where appropriate. Such epimerisation of these rel-(4S,5R)-diastereoisomers into the corresponding rel-(4R,5R)-diastereoisomers may be accomplished by treatment of a compound of formula (IIa) and/or (IIIa) with a suitable base, in the presence of a suitable solvent. For example the conversion of the rel-(4S,5R)-diastereoisomer of a compound of Formula (IIa) when L represents $CO_2Me$ into the rel-(4R,5R)-diastereoisomer is accomplished by treatment of the rel-(4S,5R)-diastereoisomer with a suitable base, such as sodium methoxide, in the presence of a suitable solvent, such as methanol.

It will be appreciated that racemic compounds of Formula (I), (Ia), (II), (IIa), (III) and/or (IIIa) may be optionally resolved into their individual enantiomers. Such resolutions may conveniently be accomplished by standard methods known in the art. For example, a racemic compound of Formula (I), (Ia), (II), (IIa), (III) and/or (IIIa) may be resolved by chiral preparative HPLC. Alternatively, racemic compounds of Formula (I), (Ia), (II), (IIa), (III) and/or (IIIa) which contain an appropriate acidic or basic group, such as a carboxylic acid group or amine group may be resolved by standard diastereoisomeric salt formation with a chiral base or acid reagent respectively as appropriate. Such techniques are well established in the art. For example, a racemic compound of Formula (IIIa) where L is $CO_2Me$ or C(O)Me may be resolved by treatment with a chiral acid such as (R)-(−)-1,1'-binaphthyl-2,2'-diyl-hydrogen phosphate, in a suitable solvent, for example isopropanol.

It will also be appreciated that individual enantiomeric compounds of Formula (I), (Ia), (II), (IIa), (III) and (IIa) may be prepared by general methods of asymmetric synthesis using, where appropriate, chiral auxiliaries or chiral catalytic reagents and additionally performing any suitable functional group interconversion step as hereinbefore described, including the addition or removal of any such chiral auxiliary. Such general methods of asymmetric synthesis are well known in the art and include, but are not restricted to, those described in "Asymmetric Synthesis," Academic Press, 1984 and/or "Chiral Auxiliaries and Ligands in Asymmetric Synthesis", Wiley, 1995. For example, suitable general chiral auxiliaries include chiral alcohols such as menthol or 1-phenylethanol; chiral oxazolidinones such as 4-benzyloxazolidin-2-one or 4-isopropyloxazolidin-2-one; or chiral amines such as 1-phenylethylamine or 2-amino-2-phenylethanol. Suitable general chiral catalytic reagents include chiral basic amines and chiral ligands such as N-methylephedrine, 1-phenyl-2-(1-pyrrolidinyl)-1-propanol, 3-(dimethylamino)-1,7,7-trimethylbicyclo[2.2.1]-heptan-2-ol, 3,4-bis(diphenylphosphanyl)-1-(phenylmethyl)pyrrolidine, chinchonine, chinchonidine, sparteine, hydroquinine or quinine, or chiral complexing agents such as chiral bis(oxazoline) (BOX) ligands and derivatives, optionally in the presence of a metal salt, for example $M_mX_x$ where M is silver, cobalt, zinc, titanium, magnesium, or manganese, and X is halide (for example chloride or bromide), acetate, trifluoroacetate, p-toluenesulfonate, trifluoromethylsulfonate, hexafluorophosphate or nitrate, and $_m$ and $_x$ are 1 or 2, and optionally in the presence of a base, for example triethylamine. All of these chiral auxiliaries or chiral catalytic reagents are well described in the art. Illustrative examples of the preparation of chiral pyrrolidines by asymmetric synthesis using chiral auxiliaries or chiral catalytic reagents include, but are not limited to, those described in *Angew. Chem. Int. Ed.*, (2002), 41: 4236; *Tetrahedron: Asymm.*, (2001), 12: 1977; *Tetrahedron: Asymm.*, (2002), 13: 2099; *J. Am. Chem. Soc.*, (2002), 124: 13400 and *Chem. Rev.*, (1998), 98: 863.

In a particular aspect, a chiral pyrrolidine compound of Formula (IIIb)

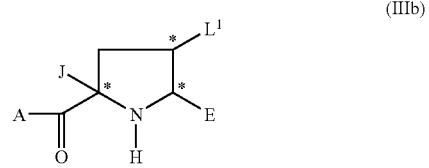

(IIIb)

in which L¹ represents CO₂Y or CO₂Y¹ wherein Y represents hydrogen or alkyl, Y¹ represents a chiral auxiliary, and A, E, and J are as defined above for Formula (I), and * denotes an enantioenriched chiral centre can be prepared by reaction of a compound of Formula (IV), as hereinbefore defined, with a compound of Formula (Va)

(Va)

in which L¹ represents a chiral ester group CO₂Y¹ wherein Y¹ represents a chiral auxiliary and thereafter optionally carrying out any conversion of CO₂Y¹ into CO₂Y by standard methods for removal of chiral auxiliaries. Such chiral ester CO₂Y¹ may be derived from a chiral alcohol Y¹OH, for example menthol, by standard esterification techniques. Preferably, the reaction of a compound of Formula (IV) with a compound of Formula (Va) is carried out in a suitable solvent, for example THF or acetonitrile, optionally in the presence of a Lewis acid catalyst, such as lithium bromide or silver acetate, and a base, such as triethylamine, 1,8-diazabicyclo[5,4,0]undec-7-ene (DBU) or tetramethyl guanidine. Alternatively, the reaction is carried out in a suitable solvent, for example THF or acetonitrile, in the presence of an add, such as acetic acid, or the reaction may be carried out by heating compounds of Formula (IV) and (Va) in a suitable solvent, for example toluene, xylene or acetonitrile in the absence of a catalyst. The preparation of compounds analogous to those of Formula (IIIb) and (Va) is described in Tetrahedron: Asymm., (1995), 6: 2475.

Optionally, the major chiral diastereoisomer of Formula (IIIb) arising from such an asymmetric reaction may be further enantioenriched by conventional purification techniques well known in the art, for example by chromatography, or by fractional crystallisation. A favourable crystallisation method is the fractional crystallisation of a salt of the major chiral diastereoisomer, for example the hydrochloride salt. The hydrochloride salt of a compound of Formula (IIIb) may be prepared by treating a compound of Formula (IIIb) with anhydrous hydrogen chloride in a suitable solvent, for example diethyl ether. Preferably the reaction is carried out at a temperature in the range −10 to 10° C.

Optional removal of a chiral auxiliary from a group in which L¹ represents CO₂Y¹ to afford a group in which L¹ represents CO₂Y is readily accomplished by standard methods, for example treatment with a hydrolytic reagent such as sodium hydroxide or an alkoxide such as sodium methoxide as appropriate, in a suitable solvent such as methanol Optionally, a chiral compound of Formula (IIIb) may be converted into a chiral compound of Formula (III) in which G represents hydroxyalkyl, and A. E, and J are as defined above for Formula (I) by treatment with suitable reagents for accomplishing the functional group interconversion of the group L¹ into group G. For example a compound of Formula (IIIb) in which L¹ represents CO₂Y¹ and Y¹ is as defined above may be treated with a suitable reducing agent, for example lithium aluminium hydride, in a suitable solvent, for example tetrahydrofuran.

Optionally, a chiral compound of Formula (IIIb) may be converted into a chiral compound of Formula (II) in which G represents hydroxyalkyl, by first acylating the pyrrolidine nitrogen atom as described above for the transformation of a compound of Formula (IIIa) into a compound of Formula (IIa) and then subsequently by treatment with suitable reagents for accomplishing the functional group interconversion of the group L¹ into group G. For example a compound of Formula (IIIb) in which L¹ represents CO₂Y¹ and Y₁, is as defined above may be treated with a suitable reducing agent, for example lithium aluminium hydride, in a suitable solvent, for example tetrahydrofuran.

It will be appreciated that, with suitable additional conversion steps as described above, chiral compounds of Formula (I) and/or (Ia) may be prepared from chiral compounds of Formula (II) or (III).

It will be appreciated that any unsaturated alkyl substituent may be converted into a saturated alkyl substituent by reduction, for example by hydrogenation over a suitable catalyst such as palladium-on-carbon, provided any other susceptable substituents are first protected and subsequently deprotected.

With appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts 'Protective Groups in Organic Synthesis', 3$^{rd}$ Ed (1999), J Wiley and Sons.

EXAMPLES

Intermediate 1

2-[N-(1,3-Thiazol-2-ylmethylene)amino]-4-methyl-pentanoic acid, tert-butyl ester

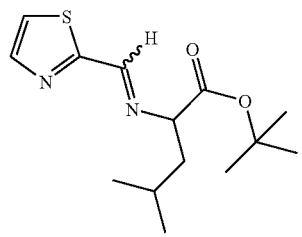

A stirred mixture of 2-amino-4-methyl-pentanoic acid tert-butyl ester, hydrochloride salt (5.00 g, 22.34 mmol), 1,3-thiazole-2-carboxaldehyde (2.53 g, 22.34 mmol) and triethylamine (3.10 mL, 22.3 mmol) in dichloromethane (60 mL) was heated under reflux under nitrogen for 19 hours. The reaction mixture was allowed to cool to room temperature, washed twice with water, dried over Na₂SO₄ and evaporated to give the title compound as an oil.

¹H NMR (CDCl₃): δ 8.46 (s, 1H), 7.94 (d, 1H), 7.44 (d, 1H), 4.07 (dd, 1H), 189-1.74 (m, 2H), 1.64-1.52 (m, 1H), 1.48 (s, 9H), 0.96 (d, 3H) and 0.90 (d, 3H).

Intermediate 2 rel-(2S,4S,5R)-2-Isobutyl-5-(1,3-thiazol-2-yl)pyrrolidine-2,4-dicarboxylic acid, 2-tert-ester, 4-methyl ester

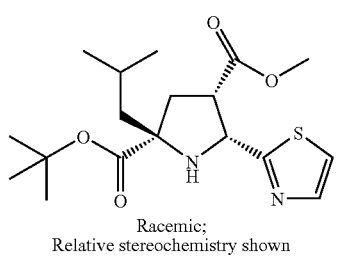

Racemic;
Relative stereochemistry shown

To a cooled (0° C.) stirred solution of Intermediate 1 (0.53 g, 1.88 mmol) in anhydrous THF (3 mL) under nitrogen, was added methyl acrylate (254 uL, 2.83 mmol) followed by lithium bromide (0.33 g, 3.80 mmol) and triethylamine (390 uL, 2.82 mmol). The reaction was stirred in a cooling bath for 5 min. and then at ambient temperature overnight. Aqueous ammonium chloride (15 mL) was added and the resulting mixture was extracted with ethyl acetate (20 mL). The extracts were combined and washed with water and brine then dried (MgSO$_4$). The solvent was evaporated in vacuo to give the title compound as a solid.

MS calcd for $(C_{18}H_{28}N_2O_4S+H)^+$: 369
MS found (electrospray): $(M+H)^+$=369.

Intermediate 3 rel-(2S,4S,5R)-2-Isobutyl-1-(3-methoxy-4-tert-butylbenzoyl)-5-(1,3-thiazol-2-yl)-pyrrolidine-2,4-dicarboxylic acid, 2-tert-butyl ester, 4-methyl ester

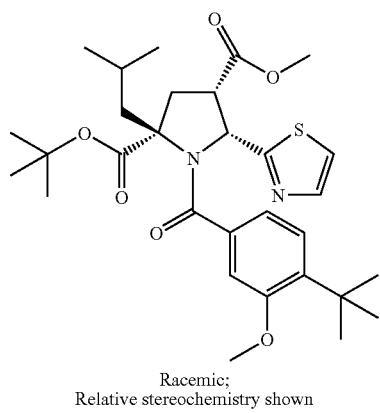

Racemic;
Relative stereochemistry shown

To a stirred solution of 3-methoxy-4-tert-butylbenzoyl chloride[1] (3.36 g, 37 mmol) in anhydrous dichloromethane (50 mL) was added Intermediate 2 (4 g, 24 mmol,) and triethylamine (2.27 mL, 37 mmol). This mixture was stirred for 6 hours under nitrogen and was then diluted with dichloromethane and washed with water. The organic phase was dried (MgSO$_4$) and evaporated in vacuo. The residue was purified by crystallisation from dichloromethane and washing with diethyl ether to provide the title compound as a solid.

MS calcd for $(C_{30}H_{42}N_2O_6S+H)^+$: 559
MS found (electrospray): $(M+H)^+$=559.

Ref. (1): Synthesised from 3-methoxy-4-tert-butylbenzoic acid (*J. Org. Chem.*, 26, 1961, 1732-1737).

Intermediate 4 and Intermediate 4a

Intermediate 4 rel-(2S,4R,5R)-2-Isobutyl-1-(3-methoxy-4-tert-butylbenzoyl)-4-hydroxymethyl-5-(1,3-thiazol-2-yl)pyrrolidine-2-carboxylic acid, tert-butyl ester

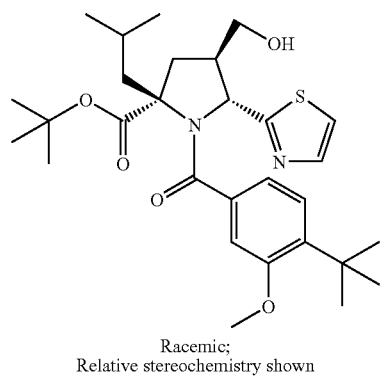

Racemic;
Relative stereochemistry shown

Intermediate 4a rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid, tert-butyl ester

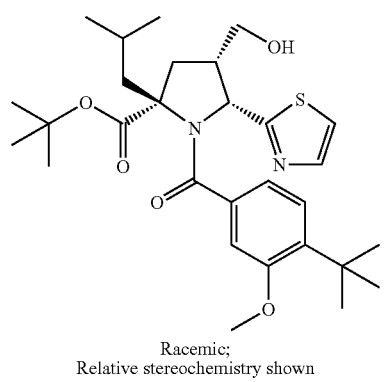

Racemic;
Relative stereochemistry shown

To a stirred solution of Intermediate 3 (2.3 g, 4.12 mmol) in anhydrous THF (23 mL) at room temperature under nitrogen, was added a 2M solution of lithium borohydride in THF (2.93 mL, 5.85 mmol). This solution was stirred at room temperature overnight and was then quenched with 1M K$_2$CO$_3$ solution (100 mL) and extracted with ethyl acetate (100 mL, then 50 mL). The combined organic phases were dried (MgSO$_4$) and evaporated in vacuo. The resulting gum was purified by chromatography on silica gel using cyclohexane-ethyl acetate (7:3 v/v) as eluent to give Intermediate 4a, rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid, tert butyl ester followed by Intermediate 4, rel-(2S,4R,5R)-2-Isobutyl-1-(3-methoxy-4-tert-butylbenzoyl)-4-hydroxymethyl-5-(1,3-thiazol-2-yl)pyrrolidine-2-carboxylic acid, tertbutyl ester.

Intermediate 4

MS calcd for (C$_{29}$H$_{42}$N$_2$O$_5$S+H)$^+$: 531
MS found (electrospray): (M+H)$^+$=531.

Intermediate 4a

MS calcd for (C$_{29}$H$_{42}$N$_2$O$_5$S+H)$^+$: 531
MS found (electrospray): (M+H)$^+$=531

Intermediate 5 rel-(2S,4R,5R)-2-Isobutyl-1-(3-methoxy-4-tert-butylbenzoyl)-4-ethoxymethyl-5-(1,3-thiazol-2-yl)pyrrolidine-2-carboxylic acid, tert-butyl ester

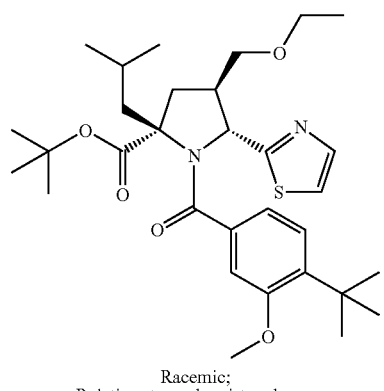

Racemic;
Relative stereochemistry shown

To a solution of Intermediate 4 (0.14 g) in anhydrous DMF (5 mL) was added sodium hydride (60% dispersion in mineral oil, 16 mg). When gas evolution had subsided iodoethane (0.084 mL) was added. The mixture was stirred at ambient temperature under an atmosphere of nitrogen for 18 h. Further quantities of sodium hydride dispersion (17 mg) and iodoethane (0.084 mL) were added and the mixture was stirred for a further 24 h. Methanol (10 mL) was added and the mixture was stirred for 10 min. Volatiles were removed and the residue was dissolved in ethyl acetate (15 mL), washed with water (15 mL) and then dried (MgSO$_4$). Removal of solvent gave the crude product which was purified by silica gel chromatography eluting with 5:1 (v/v) cyclohexane/ethyl acetate to give the title compound as an oil.

MS calcd for (C$_{31}$H$_{46}$N$_2$O$_5$S+H)$^+$: 559
MS found (electrospray): (M+H)$^+$=559

Intermediate 6 rel-(2S,4R,5R) 2-Isobutyl-1-(3-methoxy-4-tert-butylbenzoyl)-4-methoxymethyl-5-(1,3-thiazol-2-yl)pyrrolidine-2-carboxylic acid, tert-butyl ester

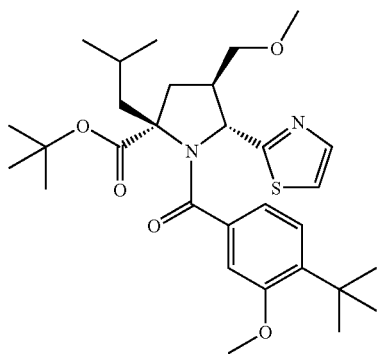

Racemic;
Relative stereochemistry shown

The title compound was prepared from Intermediate 4 in a similar manner to Intermediate 5.

MS calcd for (C$_{30}$H$_{44}$N$_2$O$_5$S+H)$^+$: 545
MS found (electrospray): (M+H)$^+$=545

Intermediate 7 rel-(2S,4R,5R)-2-Isobutyl-1-(3-methoxy-4-tert-butylbenzoyl)-4-fluoromethyl-5-(1,3-thiazol-2-yl)pyrrolidine-2-carboxylic acid, tert-butyl ester

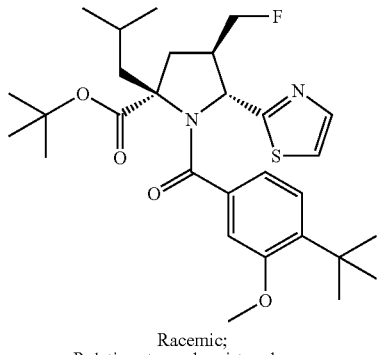

Racemic;
Relative stereochemistry shown

To a solution of Intermediate 4 (0.147 g) in anhydrous dichloromethane (3 mL) at 0° C. was added diethylamino sulfur trifluoride (0.073 mL). The cooling bath was removed and the mixture was stirred at ambient temperature for 3 h. The mixture was cooled to 0° C. and poured into pre-cooled saturated sodium hydrogen carbonate solution (10 mL) and then extracted with dichloromethane (2×20 mL). The extracts were combined, washed with brine and dried (MgSO$_4$). Solvent was removed and the residue was purified by silica gel chromatography eluting with 3:1 (v/v) cyclohexane/ethyl acetate to give the title compound as a gum.

MS calcd for (C$_{29}$H$_{41}$FN$_2$O$_4$S+H)$^+$: 533
MS found (electrospray): (M+H)$^+$=533

Intermediate 8 rel-(2S,4R,5R)-2-Isobutyl-1-(3-methoxy-4-tert-butylbenzoyl)-4-(4-fluorophenoxythio-carbonyloxymethy)-5-(1,3-thiazol-2-yl)pyrrolidine-2-carboxylic acid, 2-tert-butyl ester

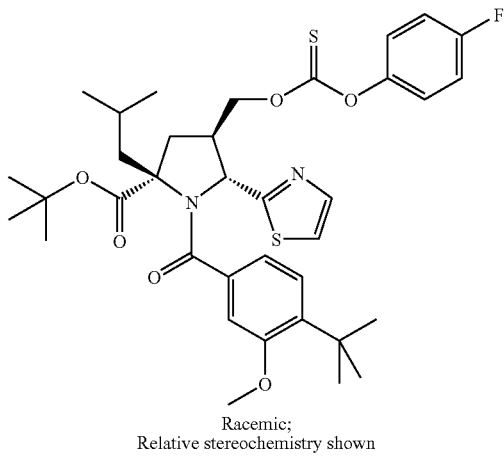

Racemic;
Relative stereochemistry shown

To a solution of Intermediate 4 (0.31 g) in anhydrous dichloromethane (5 mL) was added 4-fluorophenyl thionochloroformate (0.125 mL) followed by 4-dimethylaminopyridine (214 mg). The resulting solution was stored at ambient temperature for 2 days, diluted to 50 mL with dichloromethane and washed successively with 25 mL portions of 0.5 M hydrochloric acid, water and saturated brine, and then dried (MgSO$_4$). Solvent was removed and the residue was purified by silica gel chromatography eluting with 3:1 v/v cyclohexane/ethyl acetate to give the title compound as a foam.

MS calcd for $(C_{36}H_{45}N_2O_6S_2+H)^+$: 685
MS found (electrospray): $(M+H)^+$=685

Intermediate 9 rel-(2S,4R,5R)-2-Isobutyl-1-(3-methoxy-4-tert-butylbenzoyl)-4-methyl-5-(1,3-thiazol-2-yl)pyrrolidine-2-carboxylic acid, tert-butyl ester

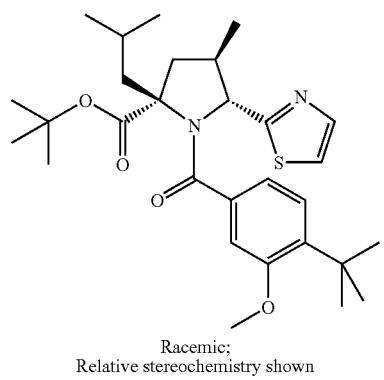

Racemic;
Relative stereochemistry shown

To a solution of Intermediate 8 (0.30 g) in dioxan (4 mL) was added 2,2'-azobis-isobutyronitrile (AIBN) (31 mg) followed by tris(trimethylsilyl)silane (0.183 mL). The mixture was heated under reflux for 30 min and set aside to cool to ambient temperature overnight. Volatiles were removed and the residue was purified by silica gel chromatography eluting with 6:1 (v/v) cyclohexane/ethyl acetate to give the title compound as a solid.

MS calcd for $(C_{29}H_{42}N_2O_4S+H)^+$: 515
MS found (electrospray): $(M+H)^+$=515

Intermediate 10 rel-(2S,4R,5R)-2-Isobutyl-4-acetyl-5-(1,3-thiazol-2-yl)pyrrolidine-2-carboxylic acid, tert-butyl ester

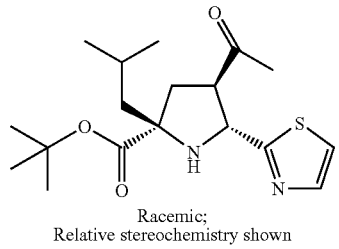

Racemic;
Relative stereochemistry shown

To a cooled (0° C.) stirred solution of Intermediate 1 (3.00 g, 10.6 mmol) in anhydrous THF (25 mL) under nitrogen, was added methyl vinyl ketone (1.0 mL, 11.7 mmol) followed by lithium bromide (1.75 g, 20.1 mmol) and triethylamine (2.2 mL, 15.9 mmol). The reaction was stirred in a cooling bath for 10 min. and then at ambient temperature overnight. The reaction mixture was diluted with ethyl acetate (80 mL) and saturated ammonium chloride solution (40 mL). The two phases were separated and the aqueous phase was re-extracted with ethyl acetate (80 mL). The extracts were combined and washed with brine then dried (MgSO$_4$). The solvent was evaporated in vacuo to give the crude product. This was purified by chromatography on silica gel using a cyclohexane-ethyl acetate gradient (95:5 v/v to 9:1 v/v) as eluent to provide the title compound as an oil.

MS calcd for $(C_{16}H_{28}N_2O_3S+H)^+$: 353.
MS found (electrospray): $(M+H)^+$=353.

Intermediate 11 rel-(2S,4R,5R)-2-Isobutyl-1-(3-methoxy-4-tert-butylbenzoyl)-4-acetyl-5-(1,3-thiazol-2--yl)pyrrolidine-2-carboxylic acid, tert-butyl ester

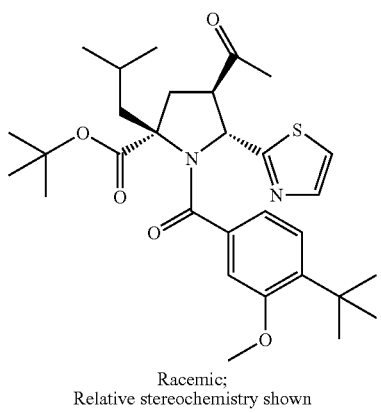

Racemic;
Relative stereochemistry shown

To a stirred solution of 3-methoxy-4-tert-butylbenzoyl chloride (0.32 g, 1.41 mmol) in anhydrous dichloromethane (5 mL) at 0° C. was added Intermediate 10 (0.45 g, 1.28 mmol) and triethylamine (196 μL, 1.41 mmol). This mixture was stirred for 16 hours and was then diluted with dichloromethane (40 mL) and washed with water (40 mL). The organic phase was dried (MgSO$_4$) and evaporated in vacuo. The residue was purified by chromatography on silica gel using a cyclohexane-ethyl acetate gradient (95:5 v/v to 85:15 v/v) as eluent to provide the title compound as a solid.

MS calcd for $(C_{30}H_{42}N_2O_5S+H)^+$: 543.
MS found (electrospray): $(M+H)^+$=543.

Intermediate 12 rel-(2S,4S,5R)-2-Isobutyl-1-(3-methoxy-4-tert-butyl-benzoyl)-4-isopropenyl-5-(1,3-thiazol-2-yl)pyrrolidine-2-carboxylic acid, tert-butyl ester

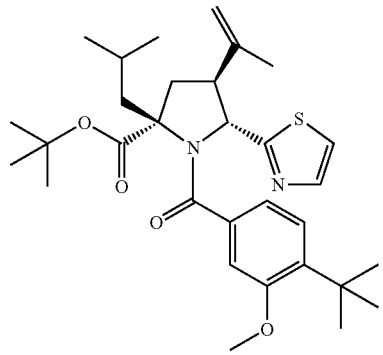

Racemic;
Relative stereochemistry shown

To a suspension of methyltriphenylphosphonium bromide (0.295 g, 0.83 mmol) in anhydrous THF (3 mL) at 0° C. under nitrogen, was added, slowly, a 1.0M solution of lithium bis(trimethylsilyl)amide in THF (0.83 mL, 0.83 mmol). The solution was stirred at 0° C. for 15 min. before addition of Intermediate 11 (0.32 g, 0.59 mmol) as a solution in anhydrous THF (4 mL). The reaction was stirred at 0° C. for 1 hour and was then left to warm to room temperature and stirred overnight. The reaction mixture was diluted with sat. ammonium chloride solution (40 mL) and ethyl acetate (40 mL). The organic phase was then washed with water (40 mL) and brine (40 mL), dried (MgSO$_4$) and the solvent evaporated in vacuo. The residue was purified by chromatography on silica gel using cyclohexane-ethyl acetate (95:5 v/v) as eluent to provide the title compound as a foam.

MS calcd for $(C_{31}H_{44}N_2O_4S+H)^+$: 541.
MS found (electrospray): $(M+H)^+$=541.

Intermediate 13 rel-(2S,4S,5R)-2-Isobutyl-1-(3-methoxy-4-tert-butyl-benzoyl)-4-isopropyl-5-(1,3-thiazol-2-yl)pyrrolidine-2-carboxylic acid, tert-butyl ester

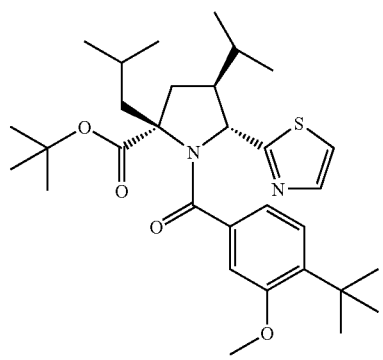

Racemic;
Relative stereochemistry shown

Intermediate 12 (0.164 g, 0.3 mmol) in ethanol (15 mL) was hydrogenated over 10% palladium on carbon (38 mg) for 6 hours. The catalyst was filtered off and the filtrate was evaporated in vacuo to give the title compound as a foam.

MS calcd for $(C_{31}H_{46}N_2O_4S+H)^+$: 543.
MS found (electrospray): $(M+H)^+$=543.

Intermediate 14 rel-(2S,4R,5R)-2-Isobutyl-1-(3-methoxy-4-tert-butylbenzoyl)-4-allyloxymethyl-5-(1,3-thiazol-2-yl)pyrrolidine-2-carboxylic acid, 2-tert-butyl ester

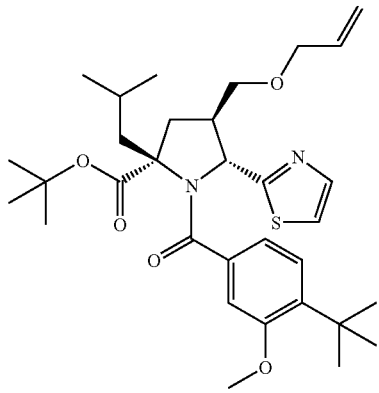

Racemic;
Relative stereochemistry shown

To a solution of Intermediate 4 (0.200 g) in anhydrous DMF (5 mL) was added sodium hydride (60% dispersion in mineral oil, 24 mg). When gas evolution had subsided allyl iodide (0.139 mL) was added. The mixture was stirred at ambient temperature under an atmosphere of nitrogen for 23 h. Methanol (10 mL) was added and the mixture was stirred for 10 min. Volatiles were removed and the residue was dissolved in ethyl acetate (15 mL), washed with water (15 mL), then brine (15 mL) and then dried (MgSO$_4$). Removal of solvent gave the crude product which was purified by silica gel chromatography eluting with 5:1 (v/v) cyclohexane/ethyl acetate to give the title compound as a gum.

MS calcd for $(C_{32}H_{46}N_2O_5S+H)^+$: 571.
MS found (electrospray): $(M+H)^+$=571.

Intermediate 15 rel-(2S,4R,5R)-2-Isobutyl-1-(3-methoxy-4-tert-butylbenzoyl)-4-propyloxymethyl-5-(1,3-thiazol-2-yl)pyrrolidine-2-carboxylic acid, 2-tert-butyl ester

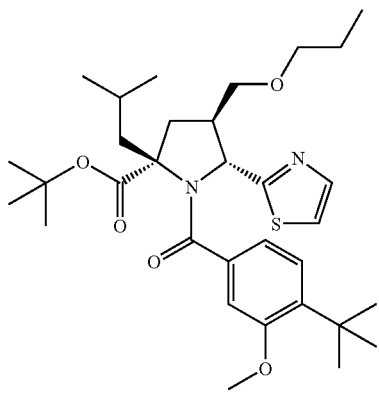

Racemic;
Relative stereochemistry shown

A solution of Intermediate 14 (0.03 g) in ethanol (5 mL) was added to 10% palladium on carbon (0.10 g) and the resulting mixture was stirred in an atmosphere of hydrogen for 4.5 h. A further quantity of 10% palladium on carbon (0.01 g) was added and the mixture was stirred in an atmosphere of hydrogen for a further 18 h. Catalyst was removed by filtration and washed with ethanol. The filtrate and washings were combined and evaporated to dryness to give the title compound as a gum.

MS calcd for ($C_{32}H_{48}N_2O_5S+H+$): 573.

MS found (electrospray): $(M+H)^+=573$.

Intermediate 16 rel-(2S,4S,5R)-2-Isobutyl-1-(3-methoxy-4-tert-butyl-benzoyl)-4-methoxymethyl-5-(1,3-thiazol-2-yl)pyrrolidine-2-carboxylic acid, tert-butyl ester

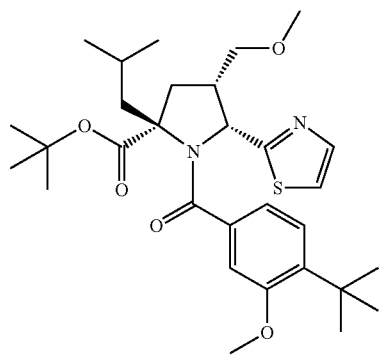

Racemic;
Relative stereochemistry shown

To a stirred solution of intermediate 4a (100 mg, 0.2 mmol) in anhydrous DMF (5 mL) was added sodium hydride (60% in mineral oil, 8 mg, 0.2 mmol) under nitrogen and at −15° C. The slurry is stirred at −15° C. over 30 min, then methyl iodide (0.25 mL, 0.4 mmol, 2 eq) was added and the reaction is stirrer at −15° C. to room temp over 18 hours.

Methanol (10 mL) was added and the reaction mixture stirred for 15 min. The solvent was evaporated and the residue partitioned between water and ethyl acetate. The organic layer was dried with $NaSO_4$ and evaporated to give a yellow oil. The oil was purified by chromatography on silica gel using cyclohexane-ethyl acetate (2:3 v/v) as eluent to provide the title compound as a solid.

MS calcd for ($C_{30}H_{44}N_2O_5S+H)^+$: 545.

MS found (electrospray): $(M+H)^+=545$.

Intermediate 17 rel-(2S,4S,5R)-2-Isobutyl-1-(3-methoxy-4-tert-butyl-benzoyl)-4-ethoxymethyl-5-(1,3-thiazol-2-yl)pyrrolidine-2-carboxylic acid, tert-butyl ester

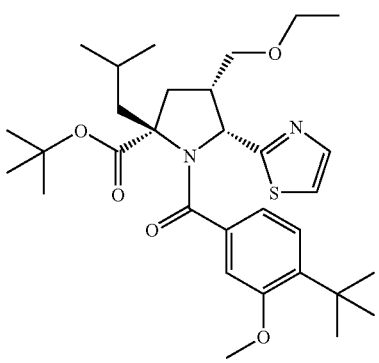

Racemic;
Relative stereochemistry shown

The title compound was prepared in a similar manner to Intermediate 16 from Intermediate 4a.

MS calcd for ($C_{31}H_{46}N_2O_5S+H)^+$: 559.

MS Found (electrospray): $(M+H)^+=559$.

Intermediate 18

(2S,4S,5R)-2-Isobutyl-5-(1,3-thiazol-2-yl)pyrrolidine-2,4-dicarboxylic acid, 2-tert-butyl ester, 4-methyl ester Enantiomer A derived from rel-(2S,4S,5R)-2-Isobutyl-5-(1,3-thiazol-2-yl)pyrrolidine-2,4-dicarboxylic acid, 2-tert-butyl ester, 4-methyl ester

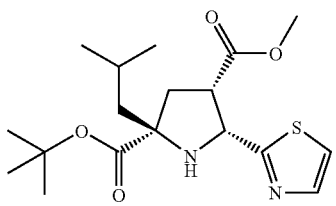

Chiral, Enantiomer A
Absolute stereochemistry shown
Stereochemistry determined by reference to Intermediate 19

Stage A: To a stirred solution of rel-(2S,4S,5R)-2-isobutyl-5-(1,3-thiazol-2-yl)pyrrolidine-2,4-dicarboxylic acid, 2-tert-butyl ester, 4-methyl ester (Intermediate 2; 4.13 g, 11.21 mmol) in 2-propanol (20.5 mL) was added a solution of (R)-1,1'-binaphthyl-2,2'-diyl-hydrogen phosphate (3.91 g, 11.22 mmol) in 2-propanol (217 mL) at 90° C. After 19 h at room temperature the crystals were collected by filtration, washed with 2-propanol (10 mL) and finally dried in vacuo to give a solid.

Stage B: This material was partitioned between ethyl acetate and saturated aqueous sodium bicarbonate and then the layers were filtered. The organic phase was separated, dried ($Na_2SO_4$) and evaporated to give Enantiomer A of the title compound as an oil.

MS calcd for $(C_{18}H_{28}N_2O_4S+H)^+$: 369.
MS found (electrospray): $(M+H)^+=369$.

Analytical chiral HPLC of rel-(2S,4S,5R)-2-isobutyl-5-(1,3-thiazol-2-yl)pyrrolidine-2,4-dicarboxylic acid, 2-tert-butyl ester, 4-methyl ester (Intermediate 2) on Chiralcel OD-H support and eluting with 5% ethanol in heptane showed two peaks of retention time 5.7 and 6.9 minutes. The title compound, Enantiomer A, was shown to correspond to the second eluting enantiomer.

The absolute stereochemistry of this compound was determined by reference to Intermediate 19.

Intermediate 19

(2S,4S,5R)-2-Isobutyl-1-(3-methoxy-4-tert-butyl-benzoyl)-5-(1,3-thiazol-2-yl) -pyrrolidine-2,4-dicarboxylic acid, 2-tert-butyl ester, 4-methyl ester Enantiomer A of rel-(2S,4S,5R)-2-Isobutyl-1-(3-methoxy-4-tert-butylbenzoyl)-5-(1,3-thiazol-2-yl)-pyrrolidine-2,4-dicarboxylic acid, 2-tert-butyl ester, 4-methyl ester

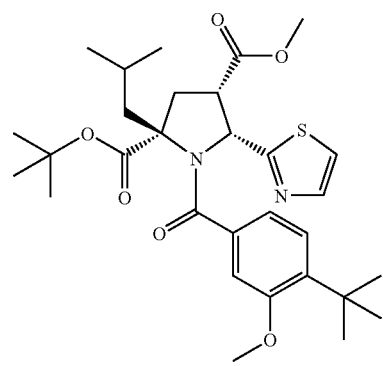

Chiral, Enantiomer A
Absolute stereochemistry shown
Stereochemistry determined by reference to Intermediate 20

To a stirred solution of Enantiomer A of rel-(2S,4S,5R)-2-isobutyl-5-(1,3-thiazol-2-yl)pyrrolidine-2,4-dicarboxylic acid, 2-tert-butyl ester, 4-methyl ester (Intermediate 18; 1.91 g, 5.18 mmol) in anhydrous dichloromethane (75 mL) was added triethylamine (0.91 mL, 6.62 mmol) and 3-methoxy-4-tert-butylbenzoyl chloride (1.39 g, 6.14 mmol). This mixture was allowed to stand at room temperature for 19 h and was then diluted with dichloromethane and then washed successively with saturated aqueous sodium bicarbonate solution (×2) and water. The organic phase was dried ($Na_2SO_4$) and evaporated to a gum which was crystallised from 1:3 ethyl acetate/cyclohexane to give Enantiomer A of the title compound as a crystalline solid.

MS calcd for $(C_{30}H_{42}N_2O_6S+H)^+$: 559.
MS found (electrospray): $(M+H)^+=559$.

The absolute stereochemistry of this compound was determined by reference to Intermediate 20.

Intermediate 20

(2S,4S,5R)-2-Isobutyl-1-(3-methoxy-4-tert-butyl-benzoyl)-4-hydroxymethyl-5-(1,3-thiazol-2-yl)pyrrolidine-2-carboxylic acid, tert-butyl ester Enantiomer A of rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid, tert-butyl ester

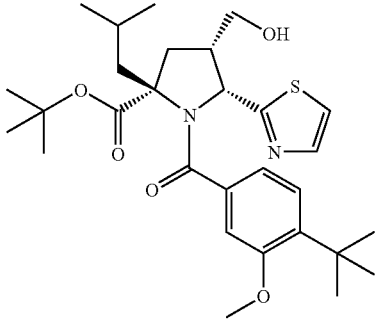

Chiral, Enantiomer A
Absolute stereochemistry shown
Stereochemistry determined by reference to Intermediate 22 and 92

A solution of Intermediate 19 (1.00 g) in dry THF (50 mL) was stirred under nitrogen at −78° C. 1.0M lithium aluminium hydride solution in THF (1.8 mL) was added dropwise. The resulting mixture was stirred and allowed to warm to −40° C. over 2 h. The mixture was quenched with 1M potassium carbonate solution (25 mL) and extracted with ethyl acetate (2×50 mL). Extracts were washed with water, then brine and dried ($MgSO_4$). Removal of solvent gave the crude product. This was dissolved in THF (30 mL), cooled under nitrogen to −78° C. and treated dropwise with stirring with 1M solution of lithium aluminium hydride in THF (1.0 mL). The mixture was allowed to warm to −20° C. over 3 h. The mixture was quenched with 1M potassium carbonate solution and extracted with ethyl acetate (2×50 mL). Extracts were washed with water, then brine and dried ($MgSO_4$). Removal of solvent gave Enantiomer A of the title compound.

MS calcd for $(C_{29}H_{42}N_2O_5S+H)^+$: 531.
MS found (electrospray): $(M+H)^+=531$.

The absolute stereochemistry of this compound was determined by reference to Intermediates 22 and 92. This compound was spectroscopically identical to that described as Intermediate 92.

Intermediate 21

(2S,4S,5R)-2-Isobutyl-1-(3-methoxy-4-tert-butylbenzoyl)-4-methoxymethyl-5-(1,3-thiazol-2-yl)pyrrolidine-2-carboxylic acid, tert-butyl ester Enantiomer A of rel-(2S,4S,5R)-2-Isobutyl-1-(3-methoxy-4-tert-butylbenzoyl)-4-methoxymethyl-5-(1,3-thiazol-2-yl)pyrrolidine-2-carboxylic acid, tert-butyl ester

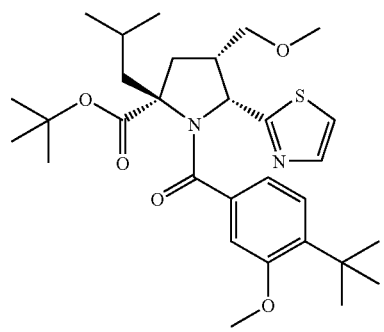

Chiral, Enantiomer A
Absolute stereochemistry shown
Stereochemistry determined by reference to Intermediate 20

A solution of Intermediate 20 (400 mg) in dry dimethylformamide (15 mL) was stirred at −15° C. under nitrogen. Sodium hydride (60% dispersion in mineral oil, 32 mg) was added and the mixture was stirred at −15° C. for 20 min. Iodomethane (0.25 mL) was added and the resulting mixture was stirred under nitrogen between −15° C. and 10° C. for 24 h. Methanol (10 mL) was added and the mixture was stirred for 10 min. The mixture was evaporated to give a yellow gum which was purified by silica gel chromatography eluting with cyclohexane/ethyl acetate mixtures (6:1 to 3:1) to give Enantiomer A of the title compound as a crystalline solid.

MS calcd for $(C_{30}H_{44}N_2O_5S+H)^+$: 545.
MS found (electrospray): $(M+H)^+=545$.

$^1$H NMR (CDCl$_3$): δ 7.49 (1H, d), 7.19 (1H, d), 7.10 (1H, d), 6.62 (1H, dd), 6.32 (1H, s), 5.46 (1H, d), 3.56 (3H, s), 3.07 (3H, s), 3.06 (1H, m), 2.96 (1H, dd), 2.82 (1H, dd), 2.25-2.40 (3H, m), 2.11 (1H, dd), 1.97 (1H, m), 1.58 (9H, s), 1.28 (9H, s), 1.08 (3H, d), 1.07 (3H, d).

The absolute stereochemistry of this compound was determined by reference to Intermediate 20.

Intermediate 22

(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid, tert-butyl ester Enantiomer A of rel-(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid, tert-butyl ester

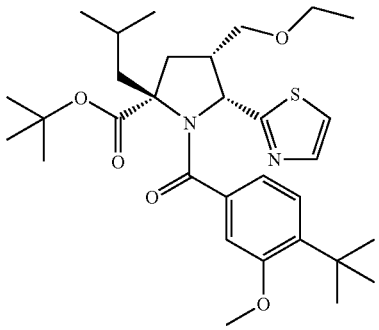

Chiral, Enantiomer A
Absolute stereochemistry shown
Stereochemistry determined by reference to Example 16

A solution of Intermediate 20 (400 mg) in dry dimethylformamide (15 mL) was stirred at −15° C. under nitrogen. Sodium hydride (60% dispersion in mineral oil, 32 mg) was added and the mixture was stirred at −15° C. for 20 min. Iodoethane (0.25 mL) was added and the resulting mixture was stirred under nitrogen between −15° C. and 10° C. for 24 h. Methanol (10 mL) was added and the mixture was stirred for 10 min. The mixture was evaporated to give a yellow gum which was purified by silica gel chromatography eluting with cyclohexane/ethyl acetate mixtures (6:1 to 3:1) to give Enantiomer A of the title compound as a crystalline solid.

MS calcd for $(C_{31}H_{46}N_2O_5S+H)^+$: 559.
MS Found (electrospray): $(M+H)^+=559$.

$^1$H NMR (CDCl$_3$): δ 7.49 (1H, d), 7.17 (1H, d), 7.10 (1H, d), 6.63 (1H, dd), 6.31 (1H, s), 5.45 (1H, d), 3.56 (3H, s), 3.00-3.20 (4H, m), 2.84 (1H, dd), 2.25-2.40 (3H, m), 2.11 (1H, dd), 1.98 (1H, m), 1.58 (9H, s), 1.28 (9H, s), 1.08 (3H, d), 1.07 (3H, d), 1.00 (3H, t).

The absolute stereochemistry of this compound was determined by reference to Example 16.

Intermediate 23

(2S,4S,5R)-2-Isobutyl-1-(3-bromo-4-tert-butylbenzoyl)-5-(1,3-thiazol-2-yl)-pyrrolidine-2,4-dicarboxylic acid, 2-tert-butyl ester, 4-methyl ester

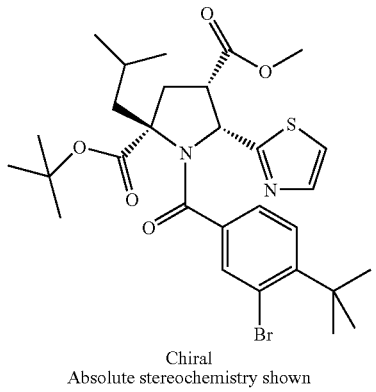

Chiral
Absolute stereochemistry shown

The title compound was prepared in a similar manner to Intermediate 19 using 3-bromo-4-tert-butylbenzoyl chloride in place of 3-methoxy-4-tert-butylbenzoyl chloride MS calcd for $(C_{29}H_{39}BrN_2O_5S+H)^+$: 607/609.
MS found (electrospray): $(M+H)^+=607/609$.

Intermediate 24

(2S,4S,5R)-1-(3-chloro-4-tert-butylbenzoyl)-2-Isobutyl-5-(1,3-thiazol-2-yl)-pyrrolidine-2,4-dicarboxylic acid, 2-tert-butyl ester, 4-methyl ester

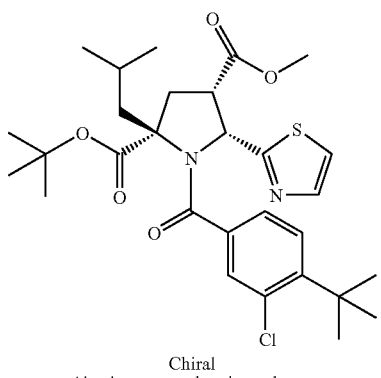

Chiral
Absolute stereochemistry shown

3-Chloro-4-tert-butylbenzoyl chloride (0.58 g, 2.51 mmol) was added to a stirred solution of the pyrrolidine salt (Stage A of Intermediate 18; 1.43 g, 1.9 mmol) and triethylamine (0.55 mL, 3.96 mmol) in anhydrous dichloromethane (18 mL) and the resulting mixture stirred at room temperature for 19 h. The mixture was diluted with dichloromethane, washed with saturated aqueous sodium bicarbonate solution, dried over $Na_2SO_4$ and evaporated. The residue was purified by chromatography on silica gel using cyclohexane-ethyl acetate (8:1 v/v) as eluent to afford the title compound, a solid.

MS calcd for $(C_{29}H_{39}ClN_2O_5S+H)^+$: 563/565.
MS found (electrospray): $(M+H)^+=563/565$.

Intermediate 25

(2S,4S,5R)-2-Isobutyl-1-(3-methyl-4-tert-butylbenzoyl)-5-(1,3-thiazol-2-yl)-pyrrolidine-2,4-dicarboxylic acid, 2-tert-butyl ester, 4-methyl ester

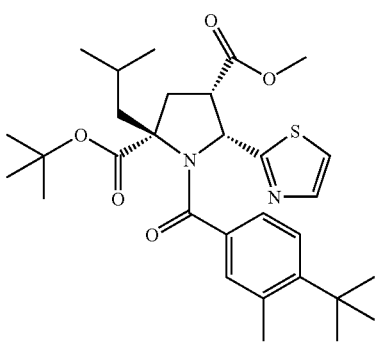

Chiral
Absolute stereochemistry shown

3-Methyl-4-tert-butylbenzoyl chloride (0.56 g, 2.65 mmol) was added to a stirred solution of the pyrrolidine salt (Stage A of Intermediate 18; 1.14 g, 1.59 mmol) and triethylamine (0.44 mL, 3.17 mmol) in anhydrous dichloromethane (15 mL) and the resulting mixture stirred at room temperature for 18 h. The mixture was diluted with dichloromethane, washed with saturated aqueous sodium bicarbonate solution, dried over $Na_2SO_4$ and evaporated. The residue was purified by chromatography on silica gel using cyclohexane-ethyl acetate (8:1 v/v) as eluent to afford the title compound, a solid.

MS calcd for $(C_{30}H_{42}N_2O_5S+H)^+$: 543.
MS found (electrospray): $(M+H)^+=543$.

Intermediate 26

(2S,4S,5R)-2-Isobutyl-1-(3-bromo-4-tert-butylbenzoyl)-4-hydroxymethyl-5-(1,3-thiazol-2-yl)-pyrrolidine-2-carboxylic acid, 2-tert-butyl ester

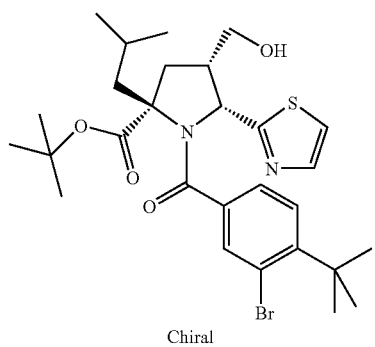

Chiral
Absolute stereochemistry shown

The title compound was prepared in a similar manner to Intermediate 20, using
Intermediate 23 as starting material.
MS calcd for $(C_{28}H_{39}BrN_2O_4S+H)^+$: 579/581.
MS found (electrospray): $(M+H)^+=579/581$.

Intermediate 27

(2S,4S,5R)-2-Isobutyl-1-(3-chloro-4-tert-butylbenzoyl)-4-hydroxymethyl-5-(1,3-thiazol-2-yl)-pyrrolidine-2-carboxylic acid, 2-tert-butyl ester

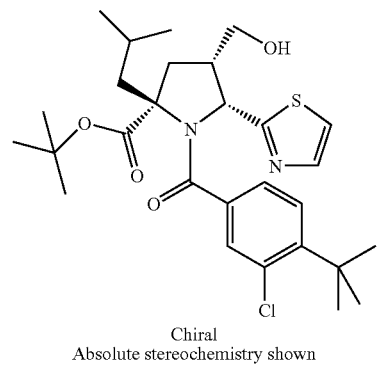

Chiral
Absolute stereochemistry shown

The title compound was prepared in a similar manner to Intermediate 20, using Intermediate 24 as starting material.
MS calcd for $(C_{28}H_{39}ClN_2O_4S+H)^+$: 535/537.
MS found (electrospray): $(M+H)^+=535/537$.

Intermediate 28

(2S,4S,5R)-2-Isobutyl-1-(3-methyl-4-tert-butylbenzoyl)-4-hydroxymethyl-5-(1,3-thiazol-2-yl)-pyrrolidine-2-carboxylic acid, 2-tert-butyl ester

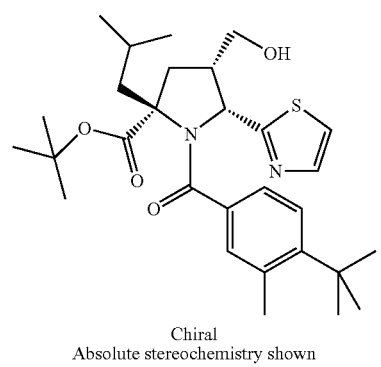

Chiral
Absolute stereochemistry shown

The title compound was prepared in a similar manner to Intermediate 20, using Intermediate 25 as starting material.
MS calcd for $(C_{29}H_{42}N_2O_4S+H)^+$: 515.
MS found (electrospray): $(M+H)^+=515$.

Intermediate 29

(2S,4S,5R)-2-Isobutyl-1-(3-bromo-4-tert-butylbenzoyl)-4-ethoxymethyl-5-(1,3-thiazol-2-yl)-pyrrolidine-2-carboxylic acid, 2-tert-butyl ester

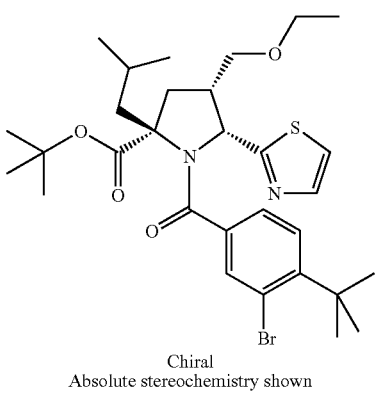

Chiral
Absolute stereochemistry shown

The title compound was prepared in a similar manner to Intermediate 22, using
Intermediate 26 as starting material.
MS calcd for $(C_{30}H_{43}BrN_2O_4S+H)^+$: 607/609.
MS found (electrospray): $(M+H)^+=607/609$.

Intermediate 30

(2S,4S,5R)-2-Isobutyl-1-(3-chloro-4-tert-butylbenzoyl)-4-ethoxymethyl-5-(1,3-thiazol-2-yl)-pyrrolidine-2-carboxylic acid, 2-tert-butyl ester

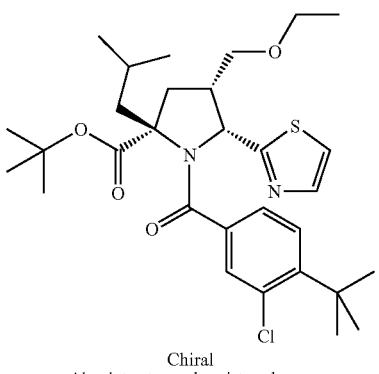

Chiral
Absolute stereochemistry shown

The title compound was prepared in a similar manner to Intermediate 22, using Intermediate 27 as starting material.
MS calcd for $(C_{30}H_{43}ClN_2O_4S+H)^+$: 563/565.
MS found (electrospray): $(M+H)^+=563/565$.

Intermediate 31

2-[N-(1,3-Thiazol-2-ylmethylene)amino]-3-phenyl-propanoic acid, tert-butyl ester

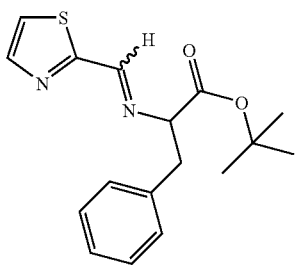

The title compound was prepared in a similar manner to Intermediate 1 replacing 2-amino-4-methyl-pentanoic acid, tert butyl ester with 2-amino-3-phenylpropanoic acid, tert butyl ester.

$^1$H NMR (CDCl3): 8.08 (1H, s), 7.80 (1H, d), 7.39 (1H, d), 7.10 (5H, m), 4.11 (1H, dd), 3.25 (1H, dd), 3.06 (1H, dd), and 1.36 (9H, s).

Intermediate 32 rel-(42R,4S,5R)-2-Benzyl-5-(1,3-thiazol-2-yl)pyrrolidine-2,4-dicarboxylic acid, 2-tert-butyl ester, 4-methyl ester

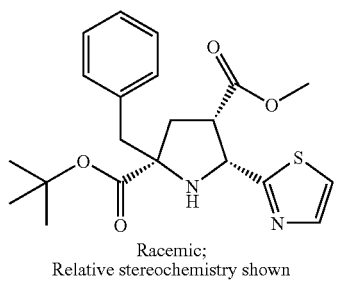

Racemic;
Relative stereochemistry shown

The title compound was prepared in a similar manner to Intermediate 2, using

Intermediate 31 as starting material.
MS calcd for $(C_{21}H_{26}N_2O_4S+H)^+$: 403.
MS found (electrospray): $(M+H)^+=403$.

Intermediate 33 rel-(42R,4S,5R)-2-Benzyl-1-(3-methoxy-4-tert-butylbenzoyl)-5-(1,3-thiazol-2-yl)-pyrrolidine-2,4-dicarboxylic acid, 2-tert-butyl ester, 4-methyl ester

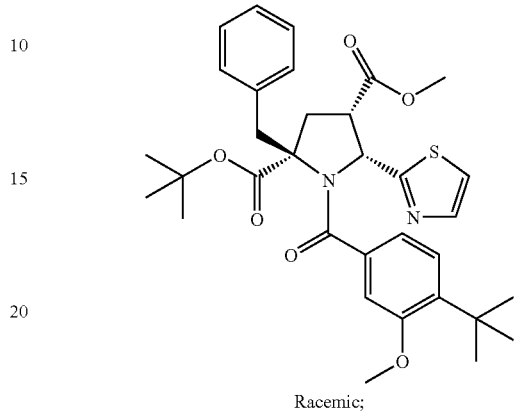

Racemic;
Relative stereochemistry shown

The title compound was prepared in a similar manner to Intermediate 3, using Intermediate 32 as starting material.
MS calcd for $(C_{33}H_{42}N_2O_6S+H)^+$: 593.
MS found (electrospray): $(M+H)^+=593$.

Intermediate 34 rel-(2R,4S,5R)-2-Benzyl-1-(3-methoxy-4-tert-butylbenzoyl)-4-hydroxymethyl-5-(1,3-thiazol-2-yl)-pyrrolidine-2-carboxylic acid, 2-tert-butyl ester

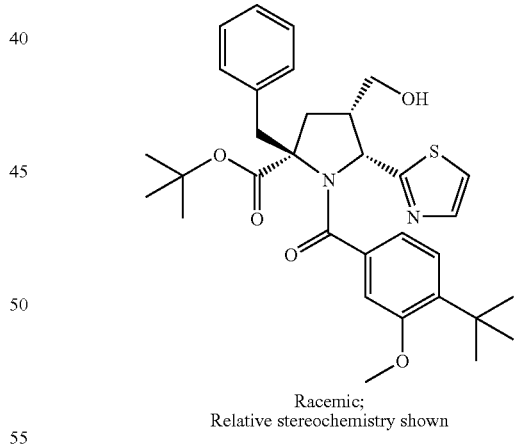

Racemic;
Relative stereochemistry shown

A solution of Intermediate 33 (1.08 g) in dry tetrahydrofuran (30 mL) was stirred under nitrogen and cooled to 0° C. 2M lithium borohydride solution in THF (1.8 mL) was added and the mixture was stirred at 0° C. for 30 min and then at room temperature for 2 days. 1M Potassium carbonate solution (10 mL) was added and the mixture was extracted with ethyl acetate. The extracts were dried (Na$_2$SO$_4$) and solvent was removed. The residue was purified by chromatography on silica gel, eluting with ethyl acetate/cyclohexane mixtures to give the title compound.
MS calcd for $(C_{32}H_{40}N_2O_5S+H)^+$: 565.

MS found (electrospray): (M+H)+=565.

Intermediate 35 rel-(42R,4R,5R)-2-Benzyl-1-(3-methoxy-4-tert-butylbenzoyl)-5-(1,3-thiazol-2-yl)-pyrrolidine-2,4-dicarboxylic acid, 2-tert-butyl ester

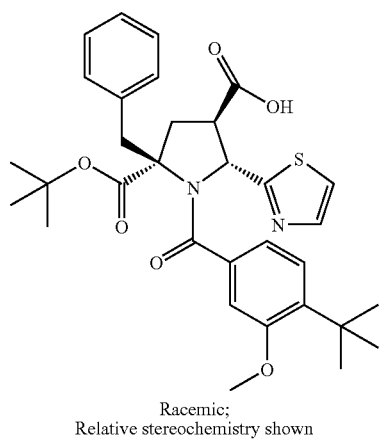

Racemic;
Relative stereochemistry shown

A solution of Intermediate 33 (1.2 g) in methanol (30 mL) was treated with 25% w/v methanolic sodium methoxide (0.439 mL) and was warmed until a complete solution was obtained. The resulting mixture was stirred at room temperature overnight. A further equivalent of sodium methoxide solution was added and the mixture was stirred for a further 4 h. The mixture was neutralised with concentrated hydrochloric acid and evaporated to dryness. The residue was dissolved in water and extracted with ethyl acetate. Solvent was removed and the residue was dissolved in methanol (10 mL) and 2M sodium hydroxide solution was added. The mixture was stirred at room temperature overnight. Solvent was removed and the residue partitioned between water and ethyl acetate. The aqueous phase was acidified to pH 6 with 2M hydrochloric acid and extracted with ethyl acetate. The combined extracts were concentrated and the residue was purified on silica gel, eluting initially with cyclohexane-ethyl acetate (9:1 v/v) and then gradually changing to ethyl acetate-methanol (95:5 v/v) to give the title compound.

MS calcd for $(C_{32}H_{38}N_2O_6S+H)^+$: 579.
MS found (electrospray): (M+H)+=579.

Intermediate 36 rel-(42R,4R,5R)-2-Benzyl-1-(3-methoxy-4-tert-butylbenzoyl)-4-hydroxymethyl-5-(1,3-thiazol-2-yl)-pyrrolidine-2-carboxylic acid, 2-tert-butyl ester

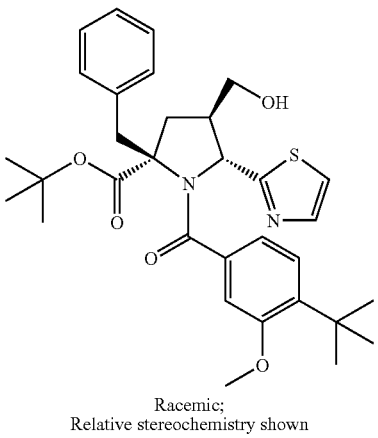

Racemic;
Relative stereochemistry shown

A solution of Intermediate 35 (602 mg) in THF (50 mL) was stirred under nitrogen at −10° C. 2M borane/dimethyl sulfide complex in THF (2 mL) was added. The mixture was warmed to room temperature and stirred overnight. Methanol was added, the solvent was removed and the residue was partitioned between 1M potassium carbonate solution and ethyl acetate. The organic layer was dried (Na2SO4). Solvent was removed and the residue was purified by chromatography on silica gel, eluting with cyclohexane:ethyl acetate (7:3 v/v) to give the title compound.

MS calcd for $(C_{32}H_{40}N_2O_5S+H)^+$: 565.
MS found (electrospray): (M+H)+=565.

Intermediate 37 rel-(2R,4R,5R)-2-Benzyl-1-(3-methoxy-4-tert-butylbenzoyl)-4-methoxymethyl-5-(1,3-thiazol-2-yl)-pyrrolidine-2-carboxylic acid, 2-tert-butyl ester

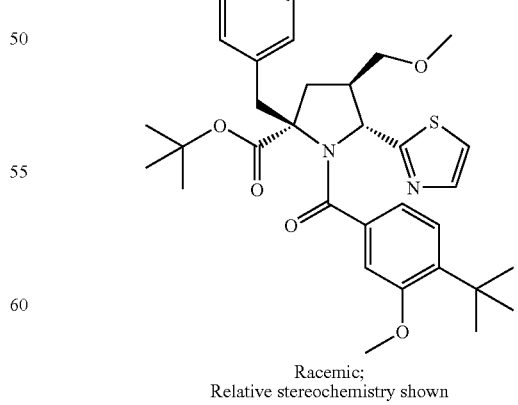

Racemic;
Relative stereochemistry shown

The title compound was prepared in a similar manner to Intermediate 16, using Intermediate 36 as starting material.

MS calcd for $(C_{33}H_{42}N_2O_5S+H)^+$: 579.
MS found (electrospray): $(M+H)^+=579$.

Intermediate 38 rel-(2R,4R,5R)-2-Benzyl-1-(3-methoxy-4-tert-butyl-benzoyl)-4-ethoxymethyl-5-(1,3-thiazol-2-yl)-pyrrolidine-2-carboxylic acid, 2-tert-butyl ester

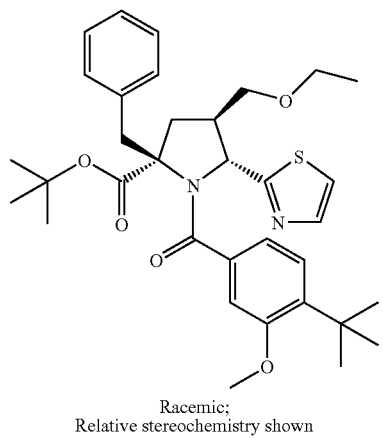

Racemic;
Relative stereochemistry shown

The title compound was prepared in a similar manner to Intermediate 17, using Intermediate 36 as starting material.
MS calcd for $(C_{34}H_{44}N_2O_5S+H)^+$: 593.
MS found (electrospray): $(M+H)^+=593$.

Intermediate 39

2-[N-(Pyrazin-2-ylmethylene)amino]-4-methylpentanoic acid, tert-butyl ester

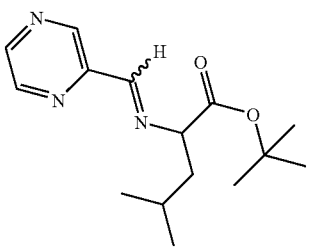

The title compound was prepared in a similar manner to Intermediate 1, using pyrazine-2-carboxaldehyde in place of 1,3-thiazole-2-carboxaldehyde.
$^1$H NMR (CDCl$_3$) δ 9.31 (d, 1H), 8.61 (m, 2H), 8.39 (s, 1H), 4.08 (dd, 1H), 1.84 (m, 2H), 1.59 (m, 1H), 1.48 (s, 9H), 0.96 (d, 3H), 0.92 (d, 3H).

Intermediate 40 rel-(2S,4S,5R)-2-Isobutyl-5-(pyrazin-2-yl)pyrrolidine-2,4-dicarboxylic acid, 2-tert-butyl ester, 4-methyl ester

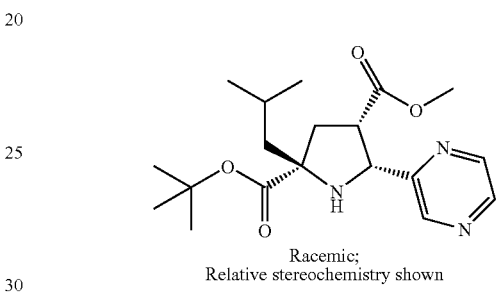

Racemic;
Relative stereochemistry shown

The title compound was prepared in a similar manner to Intermediate 2, using Intermediate 39 as starting material.
MS calcd for $(C_{19}H_{29}N_3O_4+H)^+$: 364.
MS found (electrospray): $(M+H)^+=364$.

Intermediate 41 rel-(2S,4S,5R)-2-Isobutyl-1-(3-methoxy-4-tert-butyl-benzoyl)-5-(pyrazin-2-yl)pyrrolidine-2,4-dicarboxylic acid, 2-tert-butyl ester, 4-methyl ester

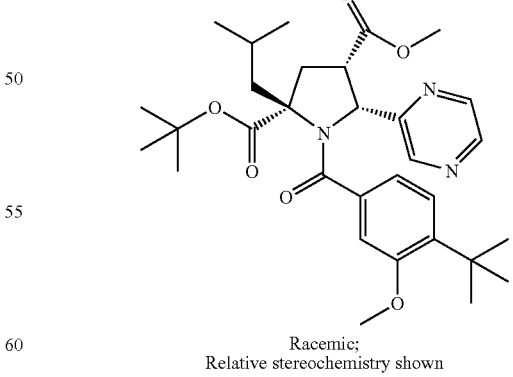

Racemic;
Relative stereochemistry shown

The title compound was prepared in a similar manner to Intermediate 3, using Intermediate 40 as starting material.
MS calcd for $(C_{31}H_{43}N_3O+H)^+$: 554.
MS found (electrospray): $(M+H)^+=554$.

Intermediate 42 rel-2S,4S,5R)-2-Isobutyl-1-(3-methoxy-4-tert-butylbenzoyl)-4-hydroxymethyl-5-(pyrazin-2-yl)-pyrrolidine-2-carboxylic acid, 2-tert-butyl ester

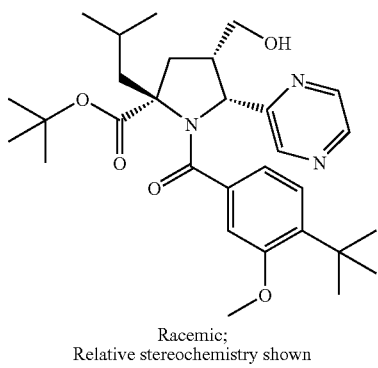

Racemic;
Relative stereochemistry shown

The title compound was prepared in a similar manner to Intermediate 20, using Intermediate 41 as starting material.

MS calcd for $(C_{30}H_{43}N_3O_r +H)^+$: 526
MS found (electrospray): $(M+H)^+$=526

Intermediate 43

Enantiomer A of rel-2S,4S,5R)-2-Isobutyl-1-(3-methoxy-4-tert-butylbenzoyl)-4-hydroxymethyl-5-(pyrazin-2-yl)-pyrrolidine-2-carboxylic acid, 2-tert-butyl ester

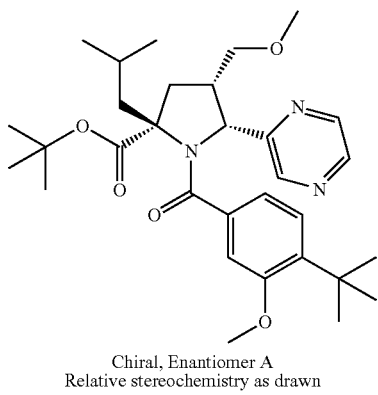

Chiral, Enantiomer A
Relative stereochemistry as drawn

A solution of Intermediate 42 (367 mg) in dry DMF (15 mL) was stirred under nitrogen and cooled to a temperature of −15° C. To this solution was added sodium hydride (60% dispersion in mineral oil, 28 mg) and the resultant solution was stirred for 20 minutes at a temperature of −15° C. Iodomethane (88 uL) was then added and the reaction was stirred for 2.5 hours at a temperature between −15 to −10° C. Methanol (10 mL) was added at −10° C. and the mixture was allowed to warm to room temperature. The mixture was diluted with ethyl acetate and washed with aqueous ammonium chloride solution, the organic phase was separated and dried (MgSO$_4$). Solvent was removed and the residue was purified by silica gel chromatography, eluting with ethyl acetate-cyclohexane (1:4 v/v) to give the racemate of the title compound. This was separated into enantiomers using preparative chiral HPLC (stationary phase: chiralpak AD, mobile phase: heptane-isopropanol 95:5 v/v). The title compound was obtained as the first eluting enantiomer.

MS calcd for $(C_{31}H_{45}N_3O_5+H)^+$: 540
MS found (electrospray): $(M+H)^+$=540

Intermediate 44 rel-(2S,4R,5R)-2-Isobutyl-1-(3-methoxy-4-tert-butylbenzoyl)-5-pyrazin-2-yl)pyrrolidine-2,4-dicarboxylic acid, 2-tert-butyl ester, 4-methyl ester

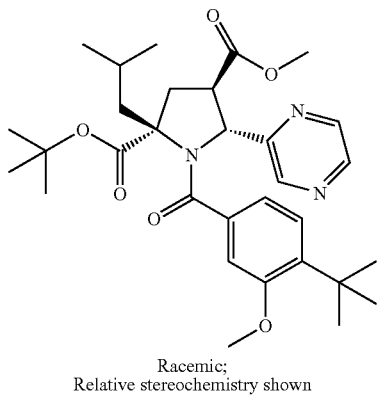

Racemic;
Relative stereochemistry shown

To a solution of Intermediate 41 (500 mg) in dry MeOH (10 mL) was added a solution of sodium methoxide (195 uL, 25% w/v). The resultant solution was stirred overnight at room temperature, before being stripped to dryness. The residue was purified by silica gel chromatography eluting with ethyl acetate-cyclohexane (1:1 v/v) to give the title compound as a white solid.

MS calcd for $(C_{31}H_{43}N_3O_6+H)^+$: 554
MS found (electrospray): $(M+H)^+$=554

Intermediate 45 rel-(2S,4R,5R)-2-Isobutyl-1-(3-methoxy-4-tert-butylbenzoyl)-4-hydroxymethyl-5-(pyrazin-2-yl)-pyrrolidine-2-carboxylic acid, 2-tert-butyl ester

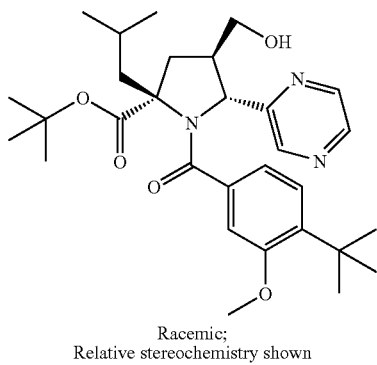

Racemic;
Relative stereochemistry shown

The title compound was prepared in a similar manner to Intermediate 4, using Intermediate 44 as starting material.

MS calcd for $(C_{30}H_{43}N_3O_5+H)^+$: 526
MS found (electrospray): $(M+H)^+$=526

Intermediate 46 rel-(2S,4R,5R)-2-Isobutyl-1-(3-methoxy-4-tert-butylbenzoyl)-4-methoxymethyl-5-(pyrazin-2-yl)-pyrrolidine-2-carboxylic acid, 2-tert-butyl ester

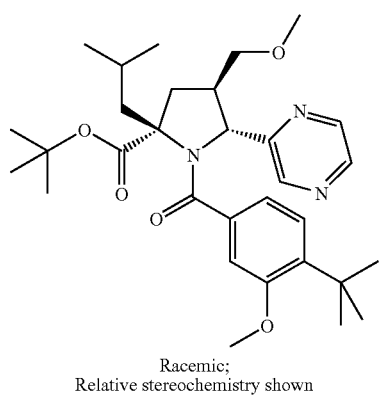

Racemic;
Relative stereochemistry shown

The title compound was prepared in a similar manner to Intermediate 16, using Intermediate 45 as starting material.

MS calcd for $(C_{31}H_{45}N_3O_5+H)^+$: 540
MS found (electrospray): $(M+H)^+=540$ Intermediate 47

2-[N-5-Methyl-1,3-thiazol-2-ylmethylene)amino]-4-methylpentanoic acid, tert-butyl ester

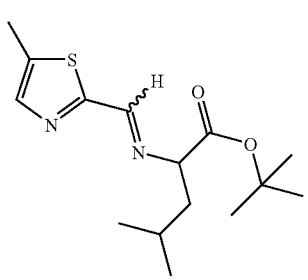

The title compound was prepared in a similar manner to Intermediate 1, using 5-methyl-1,3-thiazole-2-carboxaldehyde in place of 1,3-thiazole-2-carboxaldehyde.

$^1$H NMR (CDCl$_3$): δ 8.33 (s, 1H), 7.56 (s, 1H), 4.01 (m, 1H), 2.49 (s, 3H), 1.75 (m, 2H), 1.52 (m, 1H), 1.45 (s, 9H), 0.93 (d, 3H) and 0.88 (d, 3H).

Intermediate 48 rel-(2S,4S,5R)-2-Isobutyl-5-(5-methyl-1,3-thiazol-2-yl)pyrrolidine-2,4-dicarboxylic acid, 2-tert-butyl ester, 4-methyl ester

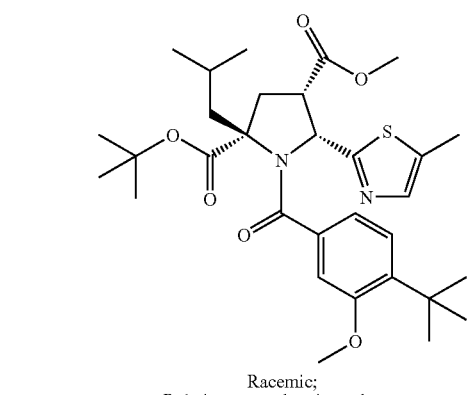

Racemic;
Relative stereochemistry shown

The title compound was prepared in a similar manner to Intermediate 2, using Intermediate 47 as starting material.

MS calcd for $(C_{19}H_{30}N_2O_4S+H)^+$: 383
MS found (electrospray): $(M+H)^+=383$ Intermediate 49 rel-(2S,4S,5R)-2-Isobutyl-1-(3-methoxy-4-tert-butylbenzoyl)-5-(5-methyl-1,3-thiazol-2-yl)pyrrolidine-2,4-dicarboxylic acid, 2-tert-butyl ester, 4-methyl ester Racemic;
Relative stereochemistry shown The title compound was prepared in a similar manner to Intermediate 3, using Intermediate 48 as starting material.

MS calcd for $(C_{31}H_{44}N_2O_6S+H)^+$: 573
MS found (electrospray): $(M+H)^+=573$

Intermediate 50 rel-(2S,4S,5R)-2-Isobutyl-1-(3-methoxy-4-tert-butyl-benzoyl)-4-hydroxymethyl-5-(5-methyl-1,3-thiazol-2-yl)pyrrolidine-2-carboxylic acid, 2-tert-butyl ester

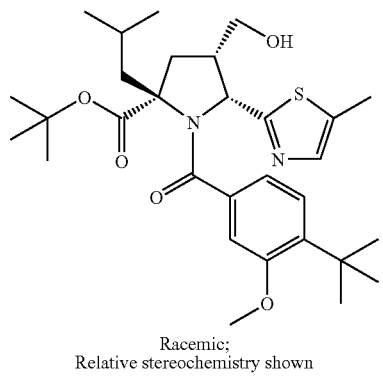

Racemic;
Relative stereochemistry shown

The title compound was prepared in a similar manner to Intermediate 20, using Intermediate 49 as starting material.

MS calcd for $(C_{30}H_{44}N_2O_5S+H)+545$

MS found (electrospray): $(M+H)^+=545$

Intermediate 51 rel-(2S,4S,5R)-2-Isobutyl-1-(3-methoxy-4-tert-butyl-benzoyl)-4-methoxymethyl-5-(5-methyl-1,3-thiazol-2-yl)pyrrolidine-2-carboxylic acid, 2-tert-butyl ester

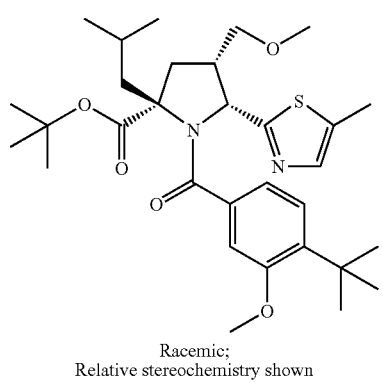

Racemic;
Relative stereochemistry shown

The title compound was prepared in a similar manner to Intermediate 21, using Intermediate 50 as starting material.

MS calcd for $(C_{31}H_{46}N_2O_5S+H)^+$: 559

MS found (electrospray): $(M+H)^+=559$

Intermediate 52

2-[N-(2-Chloro-1,3-thiazol-5-ylmethylene)amino]-4-methylpentanoic acid, tert-butyl ester

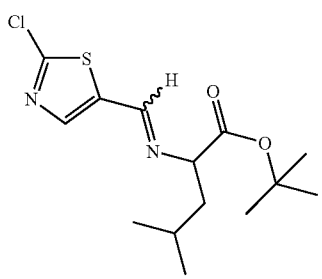

The title compound was prepared in a similar manner to Intermediate 1, using 2-chloro-1,3-thiazole-5-carboxaldehyde in place of 1,3-thiazole-2-carboxaldehyde.

$^1$H NMR (CD$_3$OD): δ 8.31 (1H,s), 7.61 (1H,s), 3.96 (1H,m), 1.75 (2H,m), 1.55 (1H, m), 1.46 (9H,s), 0.94 (3H,d) and 0.89 (3H,d)

Intermediate 53 rel-(2S,4S,5R)-2-Isobutyl-5-(2-chloro-1,3-thiazol-5-yl)pyrrolidine-2,4-dicarboxylic acid, 2-tert-butyl ester, 4-methyl ester

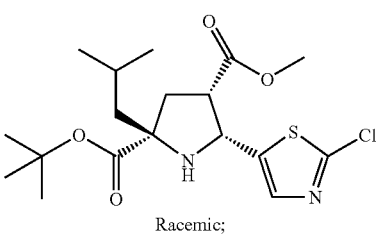

Racemic;
Relative stereochemistry shown

The title compound was prepared in a similar manner to Intermediate 2, using Intermediate 52 as starting material.

MS calcd for $(C_{18}H_{27}ClN_2O_4S+H)+$: 403/405

MS found (electrospray): $(M+H)+=403/405$

Intermediate 54 rel-(2S,4S,5R)-2-Isobutyl-1-(3-methoxy-4-tert-butyl-benzoyl)-5-(2-chloro-1,3-thiazol-5-yl)pyrrolidine-2,4-dicarboxylic acid, 2-tert-butyl ester, 4-methyl ester

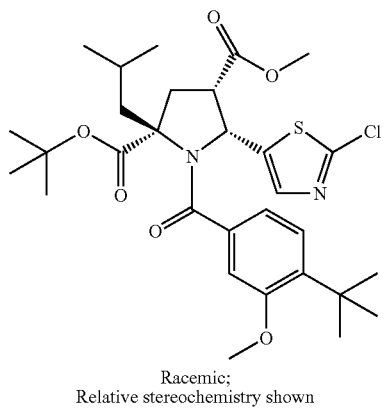

Racemic;
Relative stereochemistry shown

The title compound was prepared in a similar manner to Intermediate 3, using Intermediate 53 as starting material.
MS calcd for $(C_{30}H_{41}ClN_2O_6S+H)+$: 593/595
MS found (electrospray): (M+H)+=593/595

Intermediate 55 rel-(2S,4S,5R)-2-Isobutyl-1-(3-methoxy-4-tert-butyl-benzoyl)-4-hydroxymethyl-5(2-chloro-1,3-thiazol-5-yl)pyrrolidine-2-carboxylic acid, 2-tert-butyl ester

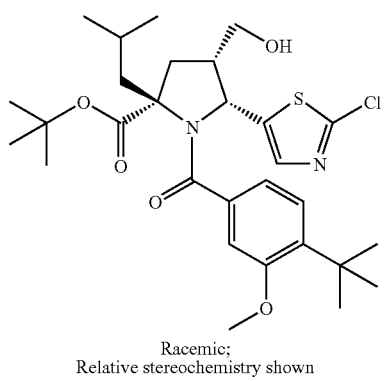

Racemic;
Relative stereochemistry shown

The title compound was prepared in a similar manner to Intermediate 20, using Intermediate 54 as starting material.

MS calcd for $(C_{29}H_{41}ClN_2O_5S+H)+$: 565/567
MS found (electrospray): (M+H)+=565/567.

Intermediate 56 rel-(2S,4S,5R)-2-Isobutyl-1-(3-methoxy-4-tert-butyl-benzoyl)-4-methoxymethyl-5-(2-chloro-1,3-thiazol-5-yl)pyrrolidine-2-carboxylic acid, 2-tert-butyl ester

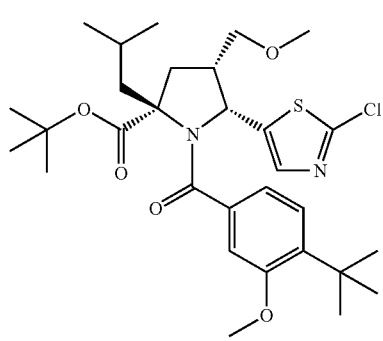

Racemic;
Relative stereochemistry shown

The title compound was prepared in a similar manner to Intermediate 16, using Intermediate 55 as starting material.
MS calcd for $(C_{30}H_{43}ClN_2O_5S+H)+$: 579/581
MS found (electrospray): (M+H)+=579/581

Intermediate 57 rel-(2S,4S,5R)-2-Isobutyl-1-(3-methoxy-4-tert-butyl-benzoyl)-4-methoxymethyl-5-(2-methoxy-1,3-thiazol-5-yl)pyrrolidine-2-carboxylic acid, 2-tert-butyl ester

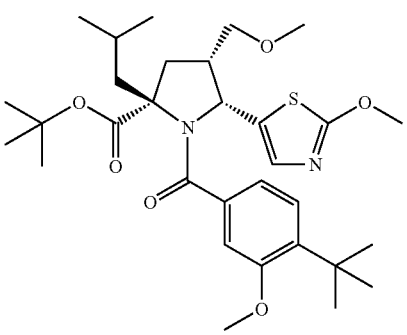

Racemic;
Relative stereochemistry shown

To a solution of Intermediate 56 (70 mg) in methanol (0.8 mL) was added 1M sodium hydroxide in methanol (0.207 mL). The mixture was heated at 50° C. overnight and then at reflux for 8 h. The mixture was purified by preparative HPLC on a C18 column using a two-solvent gradient elution with (A) water containing formic acid (0.1%) and (B) acetonitrile-water (95:5 v/v) containing formic acid (0.05%) as eluents to give the title compound.

MS calcd for $(C_{31}H_{46}N_2O_6S+H)^+$: 575
MS found (electrospray): $(M+H)^+=575$
$^1$H NMR (CDCl$_3$): δ 7.13 (1H, d), 6.91 (1H, s), 6.66 (1H, d), 6.43 (1H, s), 5.04 (1H, d), 3.99 (3H, s), 3.65 (3H, s), 3.18 (1H, m) 3.13 (3H, s), 2.94 (2H, m), 2.26 (1H, m), 2.17 (1H, m), 2.05 (2H, m), 1.95 (1H, m), 1.59 (9H, s), 1.32 (9H, s), 1.06 (6H, d).

Intermediate 58 rel-(2S,4R,5R)-2-Isobutyl-1 (3-methoxy-4-tert-butylbenzoyl)-4-((methylthio)methyl)-5-(1,3-thiazol-2-yl)pyrrolidine-2-carboxylic acid, tert-butyl ester

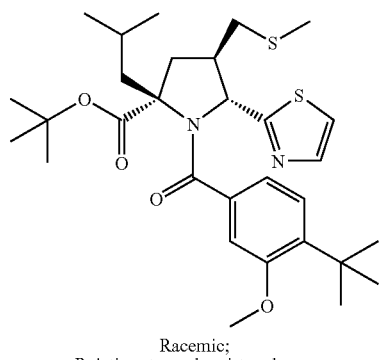

Racemic;
Relative stereochemistry shown

A solution of trifluoromethanesulfonic anhydride (53 mg) and pyridine (15 mg) in dichloromethane (0.5 mL) was stirred at −10° C. under nitrogen and treated with a solution of Intermediate 4 (100 mg) in dichloromethane (1 mL) for 1.5 h. Water (3 mL) was added, the organic layer was collected and dried by passage through a hydrophobic frit. Solvent was removed and the residue was treated, under nitrogen, with a solution of sodium methanethiolate (60 mg) in dimethyl formamide (1.5 mL) at room temperature for 3 days. Solvent was removed in vacuum and the residue was partitioned between dichloromethane and brine. The dichloromethane solution was chromatographed on silica gel using cyclohexane-ethyl acetate (gradient elution from 15:1 v/v to 12:1 v/v) to give the title compound.

MS calcd for $(C_{30}H_{44}N_2O_4S_2+H)^+$: 561
MS found (electrospray): $(M+H)^+=561$ Intermediate 59 rel-(2S,4R,5R)-2-Isobutyl-1-(3-methoxy-4-tert-butylbenzoyl)-4-((methanesulfonyl)-methyl)-5-(1,3-thiazol-2-yl)pyrrolidine-2-carboxylic acid, tert-butyl ester

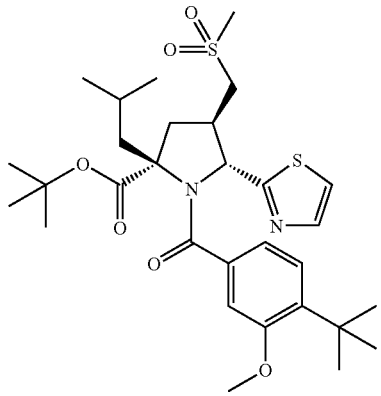

Racemic;
Relative stereochemistry shown

To a solution of Intermediate 58 (28.8 mg) in dichloromethane (1 mL) at 0° C. was added a solution of 3-chloroperbenzoic acid (21 mg) in dichloromethane (1 mL). The mixture was stirred at 0° C. under nitrogen for 2.75 h and then washed successively with sodium sulfide solution, sodium bicarbonate solution and water, and then dried by passage through a hydrophobic frit. The resulting solution was chromatographed on silica gel using cyclohexane-ethyl acetate (gradient elution from 2:1 v/v to 1:1 v/v) to give the title compound.

MS calcd for $(C_{30}H_{44}N_2O_6S_2+H)^+$: 593
MS found (electrospray): $(M+H)^+=593$ Intermediate 60 rel-(2S,4R,5R)-2-Isobutyl-1-(3-methoxy-4-tert-butylbenzoyl)-4-(1,1 difluoroethyl)-5-(1,3-thiazol-2-yl) pyrrolidine-2-carboxylic acid, tert-butyl ester

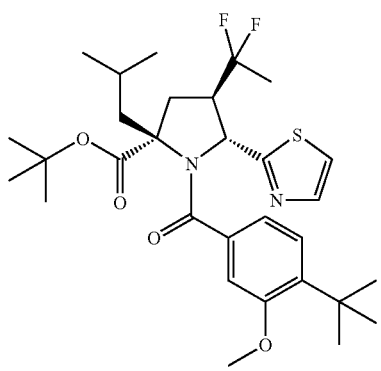

Racemic;
Relative stereochemistry shown

Diethylamino sulfur trifluoride (450 uL) was added dropwise to a stirred solution of Intermediate 11 (282.3 mg) in dichloromethane (2.5 mL) at 0° C. under nitrogen. The temperature was raised to room temperature and stirring was continued overnight. After being cooled to 0° C. the mixture was poured into ice-cold saturated sodium hydrogen carbonate solution (12 mL). The mixture was extracted with dichloromethane (40 mL) and the extracts dried (MgSO$_4$). The solvent was removed to give a residue which was purified by chromatography on silica gel, eluting with cyclohexane-ethyl acetate (9:1 v/v), to give the title compound.

MS calcd for $(C_{30}H_{42}F_2N_2O_4S+H)^+$: 565
MS found (electrospray): $(M+H)^+$=565

Intermediate 61 rel-(2S,4R,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid, tert-butyl ester

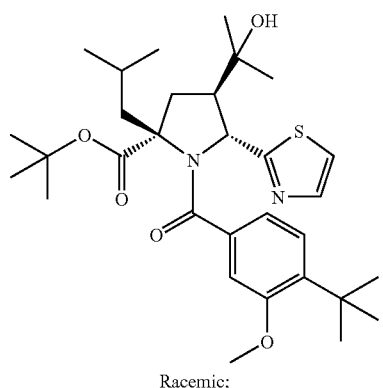

Racemic;
Relative stereochemistry shown

Method A: To a solution of Intermediate 11 (46 mg) in tetrahydrofuran (1 mL) was added 1.4M methylmagnesium bromide solution in toluene/THF (0.1 mL). The mixture was stirred at 0° C. under nitrogen for 70 min and then allowed to warm to room temperature. Saturated ammonium chloride solution (2 mL) was added and the mixture was extracted with dichloromethane. Extracts were dried (MgSO$_4$) and solvent removed to give the crude product which was purified by preparative HPLC on a C18 column using a two-solvent gradient elution with (A) water containing formic acid (0.1%) and (B) acetonitrile-water (95:5 v/v) containing formic acid (0.05%) as eluents to afford the title compound MS calcd for $(C_{31}H_{46}N_2O_5S+H)^+$: 559
MS found (electrospray): $(M+H)^+$=559

Method B: A solution of Intermediate 11 (51.7 mg) in dry tetrahydrofuran (1 mL) was stirred at −78° C. under nitrogen. 1.5M methyl lithium as complex with lithium bromide in ether (76 uL) was added and the mixture was stirred at −78° C. for 2 h. A further quantity of the 1.5M methyl lithium-lithium bromide complex in ether (32 uL) was added and stirring was continued for a further 40 min. Saturated ammonium chloride solution (10 mL) was added and the mixture was extracted with dichloromethane. The extracts were dried (MgSO$_4$). Solvent was removed to give a residue which was purified by silica gel chromatography, eluting with cyclohexane-ethyl acetate (4:1 v/v) to give the title compound.

Spectroscopic data consistent with that for the product obtained by Method A.

Intermediate 62

Enantiomer A of rel-(2S,4R,5R)-2-Isobutyl-1-(3-methoxy-4-tert-butylbenzoyl)-4-methoxymethyl-5-(1,3-thiazol-2-yl)pyrrolidine-2-carboxylic acid, tert-butyl ester

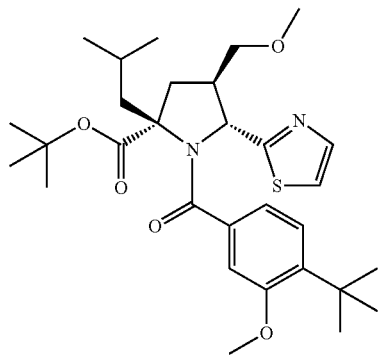

Chiral Enantiomer A;
Relative stereochemistry shown

Intermediate 6 was resolved on a Chiralpak AD preparative chiral hplc column using heptane-isopropanol (98:2 v/v) as eluent to give the title compound, the second eluting enantiomer.

MS calcd for $(C_{30}H_{44}N_2O_5S+H)^+$: 545
MS found (electrospray): $(M+H)^+$=545

Intermediate 63 rel-(2R,4S,5R)-2-Benzyl-1-(3-methoxy-4-tert-butylbenzoyl)-4-methoxymethyl-5-(1,3-thiazol-2-yl)-pyrrolidine-2-carboxylic acid, 2-tert-butyl ester

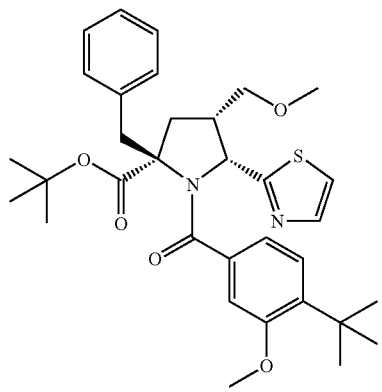

Racemic;
Relative stereochemistry shown

The title compound was prepared in a similar manner to Intermediate 16, using Intermediate 34 as starting material.

MS calcd for $(C_{33}H_{42}N_2O_5S+H)^+$: 579
MS found (electrospray): $(M+H)^+$=579

Intermediate 64 rel-(2R,4S,5R)-2-Benzyl-1-(3-methoxy-4-tert-butyl-benzoyl)-4-ethoxymethyl-5-(1,3-thiazol-2-yl)-pyrrolidine-2-carboxylic acid, 2-tert-butyl ester

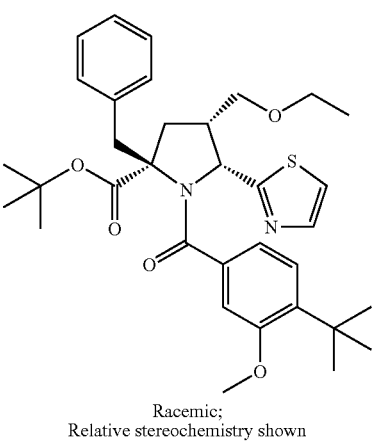

Racemic;
Relative stereochemistry shown

The title compound was prepared in a similar manner to Intermediate 17, using Intermediate 34 as starting material.
MS calcd for $(C_{34}H_{44}N_2O_5S+H)^+$: 593
MS found (electrospray): $(M+H)^+=593$

Intermediate 65

2-[N-Pyridin-2-ylmethylene)amino]-4-methylpentanoic acid, tert-butyl ter

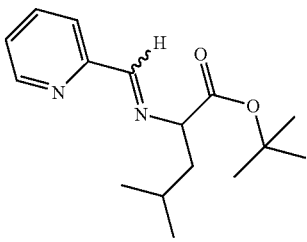

The title compound was prepared in a similar manner to Intermediate 1, using pyridine-2-carboxaldehyde in place of 1,3-thiazole-2-carboxaldehyde.
$^1$H NMR (CD$_3$OD): δ 8.66 (1H, d), 8.37 (1H, s), 8.12 (1H, d), 7.75 (1H, t), 4.05 (1H, m), 1.83 (2H, m), 1.55 (1H, m) 1.48 (9H, s), 0.96 (3H, d), 0.91 (3H, d).

Intermediate 66 rel-(2S,4S,5R)-2-Isobutyl-5-(pyridin-2-yl)pyrrolidine-2,4-dicarboxylic acid, 2-tert-butyl ester, 4-methyl ester

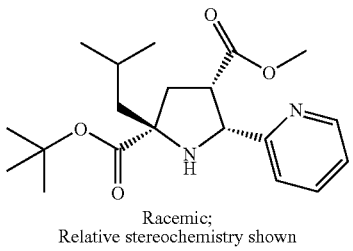

Racemic;
Relative stereochemistry shown

The title compound was prepared in a similar manner to Intermediate 2, using Intermediate 65 as starting material.
$^1$H NMR (CD$_3$OD): δ 8.52 (1H, d), 7.62 (1H, t), 7.29 (1H, d), 7.13 (1H, t), 4.60 (1H, t), 3.37 (1H, q), 3.26 (3H, s) 2.60 (1H, dd), 2.01 (1H, dd), 1.80 (2H, m), 1.54 (1H, m), 1.51 (9H, s), 0.97 (3H, d), 0.90 (3H, d).

Intermediate 67 rel-(2S,4S,5R)-2-Isobutyl-1-(3-methoxy-4-tert-butyl-benzoyl)-5-(pyridin-2-yl)-pyrrolidine-2,4-dicarboxylic acid, 2-tert-butyl ester, 4-methyl ester

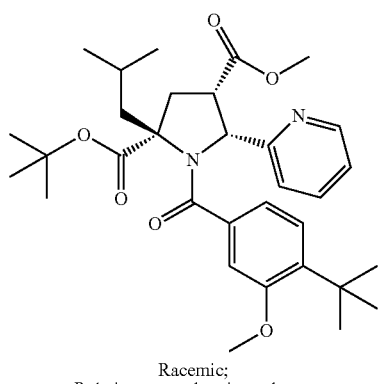

Racemic;
Relative stereochemistry shown

The title compound was prepared in a similar manner to Intermediate 3, using Intermediate 66 as starting material.
$^1$H NMR (CD$_3$OD): δ 8.20 (1H, d), 7.92 (1H, d), 7.57 (1H, t), 7.07 (1H, d), 7.07 (1H, d), 7.03 (1H, t), 6.63 (1H, d), 6.26 (1H, s), 5.42 (1H, d), 3.77 (1H, m), 3.49 (3H, s), 3.33 (3H, s), 2.90 (1H, t), 2.31 (2H, m), 2.14 (1H, m), 1.95 (1H, m), 1.43 (9H, s), 1.25 (9H, s), 1.10 (6H, d).

Intermediate 68 rel-(2S,4S,5R)-2-Isobutyl-1-(3-methoxy-4-tert-butyl-benzoyl)-4-hydroxymethyl-5-(pyridin-2-yl)pyrrolidine-2-carboxylic acid, 2-tert-butyl ester

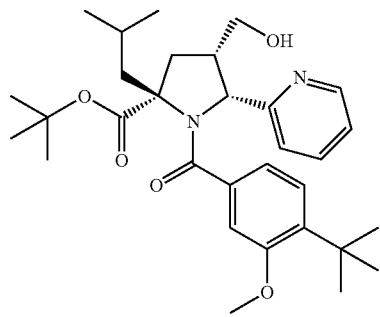

Racemic;
Relative stereochemistry shown

The title compound was prepared in a similar manner to Intermediate 20, using Intermediate 67 as starting material.

MS calcd for $(C_{31}H_{44}N_2O_5+H)^+$: 525
MS found (electrospray): $(M+H)^+=525$ Intermediate 69 rel-(2S,4S,5R)-2-Isobutyl-1-(3-methoxy-4-tert-butyl-benzoyl)-4-methoxymethyl-5-(pyridin-2-yl)pyrrolidine-2-carboxylic acid, 2-tert-butyl ester

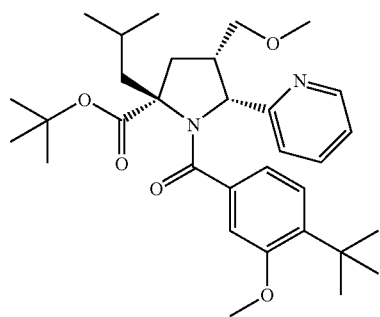

Racemic;
Relative stereochemistry shown

The title compound was prepared in a similar manner to Intermediate 16, using Intermediate 68 as starting material.

MS calcd for $(C_{32}H_{46}N_2O_5+H)^+$: 539
MS found (electrospray): $(M+H)^+=539$ Intermediate 70

(2S,4R,5R)-2-Isobutyl-4-acetyl-5-(1,3-thiazol-2-yl)pyrrolidine-2-carboxylic acid, tert-ester, (R)-(−)-1,1'-binaphthyl-2,2'-diyl-hydrogen phosphate salt

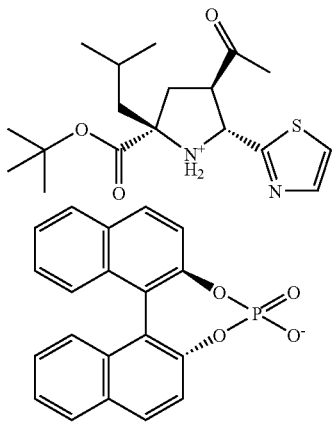

Chiral;
Absolute stereochemistry shown

To a solution of Intermediate 10 (6.51 g) in isopropyl alcohol (30 mL) was added a hot (90° C.) solution of (R)-(−)-1,1'-binaphthyl-2,2'-diyl-hydrogen phosphate (6.30 g) in isopropyl alcohol (337 mL). The mixture was allowed to stand at room temperature overnight and then concentrated by evaporation of ca. 80 mL of solvent. After being allowed to stand at room temperature overnight the title compound was collected by filtration. The absolute stereochemistry was confirmed by X-ray crystallography and showed the pyrrolidine base to have (2S,4R,5R) chirality.

$^1$H NMR (CD$_3$OD) δ 8.03 (d, 2H), 7.96 (d, 2H), 7.85 (d, 1H), 7.72 (d, 1H), 7.54 (d ,2H), 7.42 (t, 2H), 7.26 (m, 4H), 5.37 (d, 1H), 3.79 (m, 1H), 3.10 (s, 3H), 2.25 (dd , 1H), 2.22 (s, 3H), 1.96 (m, 2H), 1.74 (m, 1H), 1.53 (s, 9H), 0.97 (d, 3H), 0.95 (d, 3H).

Intermediate 71

(2S,4R,5R)-2-Isobutyl-1-(3-methoxy-4-tert-butyl-benzoyl)-4-acetyl-5-(1,3-thiazol -2-yl)pyrrolidine-2-carboxylic acid, tert-butyl ester

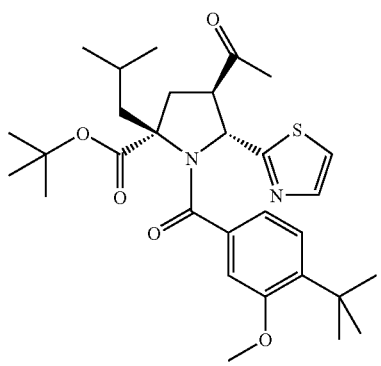

Chiral;
Absolute stereochemistry shown

Intermediate 70 (4.2 g) was added to a solution of 3-methoxy-4-tert-butylbenzoyl chloride (1.4949) in dichloromethane (150 mL) and stirred until homogeneous. Triethylamine (2.087 mL) was added and the mixture was stirred under nitrogen at room temperature overnight. A further portion of 3-methoxy-4-tert-butylbenzoyl chloride (272 mg) in dichloromethane (1 mL) was added and stirring was continued for a further 24 h. Saturated sodium bicarbonate solution (150 mL) was added and the organic layer was collected and dried (MgSO$_4$). Solvent was removed and the residue was purified by silica gel chromatography, eluting with cyclohexane-ethyl acetate (3:1 v/v) to give the title compound as a solid.

MS calcd for (C$_{30}$H$_{42}$N$_2$O$_5$S+H)$^+$: 543
MS found (electrospray): (M+H)$^+$=543

Intermediate 72

(2S,4R,5R)-2-Isobutyl-1-(3-methoxy-4-tert-butyl-benzoyl)-4-(1-hydroxy-1-methylethyl)-5-(1,3-thiazol-2-yl)pyrrolidine-2-carboxylic acid, tert-butyl ester

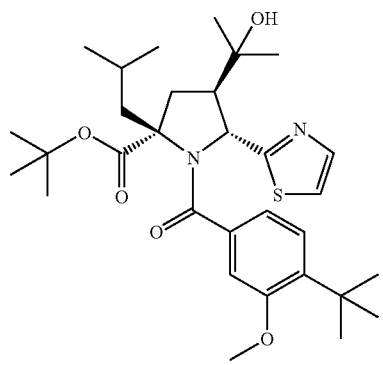

Chiral;
Absolute stereochemistry shown

The title compound was prepared in a similar manner to that described in Intermediate 61 (Method B), replacing Intermediate 11 with Intermediate 71.

MS calcd for (C$_{31}$H$_{46}$N$_2$O$_5$S+H)$^+$: 559
MS found (electrospray): (M+H)$^+$=559

Intermediate 73

(2S,4R,5R)-2-isobutyl-1-(3-methoxy-4-tert-butyl-benzoyl)-4-acetyl-5-(1,3-thiazol-2-yl)pyrrolidine-2-carboxylic acid

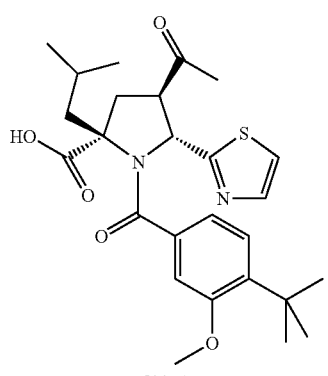

Chiral;
Absolute stereochemistry shown

The title compound was prepared in a similar manner to Example 1, using Intermediate 71 as the starting material.

$^1$H NMR (CDCl$_3$): δ 8.10 (d, 1H), 7.68 (d, 1H), 7.39 (d, 1H), 7.05 (d, 1H), 6.60 (s, 1H), 6.27 (d, 1H), 3.88 (m 1H), 3.72, (s, 3H), 3.03 (dd, 1H), 2.79 (t, 1H), 2.73 (dd, 1H), 2.32 (s, 3H), 2.18 (dd, 1H), 1.86 (m, 1H), 1.35 (s, 9H), 1.16 (d, 3H), 1.04 (d, 3H).

Intermediate 74

2-[N-(1,3-thiazol-4-ylmethylene)amino]-4-methyl-pentanoic acid, tert-butyl ester

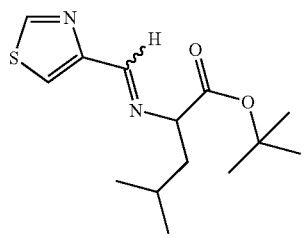

The title compound was prepared in a similar manner to Intermediate 1, using 1,3 thiazole-4-carboxaldehyde in place of 1,3-thiazole-2-carboxaldehyde.

$^1$H NMR (CDCl$_3$): δ 8.85 (1H, d), 8.49 (1H, s), 8.01 (1H, d), 4.03-3.98 (1H, m), 3.11 (2H, dd), 1.64-1.52(1H, m), 1.48 (9H, s), 0.96 (3H, d) and 0.91 (3H, d).

Intermediate 75 rel-(2S,4S,5R)-2-Isobutyl-5-(1,3-thiazol-4-yl)pyrrolidine-2,4-dicarboxylic acid, 2-tert-butyl ester, 4-methyl ester

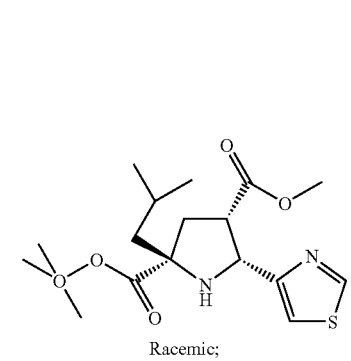

Racemic;
Relative stereochemistry shown

The title compound was prepared in a similar manner to Intermediate 2, using Intermediate 74 as starting material.
MS calcd for $(C_{18}H_{28}N_2O_4S+H)^+$: 369
MS found (electrospray): $(M+H)^+=369$ Intermediate 76 rel-(2S,4S,5R)-2-Isobutyl-1-(3-methoxy-4-tert-butyl-benzoyl)-5-(1,3-thiazol-4-yl)pyrrolidine-2,4-dicarboxylic acid, 2-tert-butyl ester, 4-methyl ester

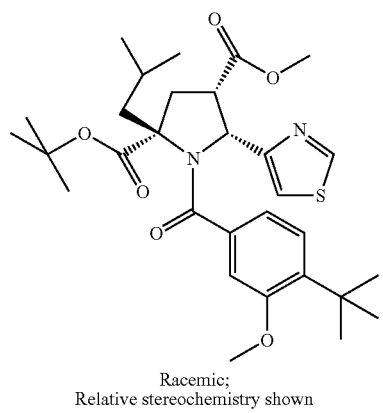

Racemic;
Relative stereochemistry shown

The title compound was prepared in a similar manner to Intermediate 3, using Intermediate 75 as starting material.
MS calcd for $(C_{30}H_{42}N_2O_6S+H)^+$: 559
MS found (electrospray): $(M+H)^+=559$ Intermediate 77 rel-(2S,4S,5R)-2-Isobutyl-1-(3-methoxy-4-tert-butyl-benzoyl)-4-hydroxymethyl-5-(1,3-thiazol-yl)pyrrolidine-2-carboxylic acid, 2-tert-butyl ester

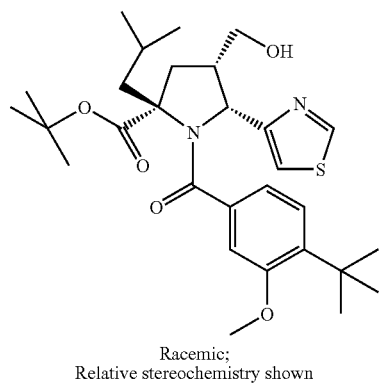

Racemic;
Relative stereochemistry shown

The title compound was prepared in a similar manner to Intermediate 20, using intermediate 76 as starting material.
MS calcd for $(C_{29}H_{42}N_2O_5S+H)^+$: 531
MS found (electrospray): $(M+H)^+=531$ Intermediate 78 rel-(2S,4S,5R)-2-Isobutyl-1-(3-methoxy-4-tert-butyl-benzoyl)-4-ethoxymethyl-54-(1,3-thiazol-4-yl)pyrrolidine-2-carboxylic acid, 2-tert-butyl ester

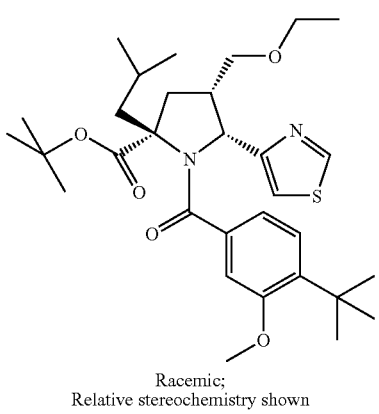

Racemic;
Relative stereochemistry shown

The title compound was prepared in a similar manner to Intermediate 22, using Intermediate 77 as starting material.
MS calcd for $(C_{31}H_{46}N_2O_5S+H)^+$: 559
MS found (electrospray): $(M+H)^+=559$ Intermediate 79

Enantiomer A of rel-(2S,4S,5R)-2-Isobutyl-1 (3-methoxy-4-tert-butylbenzoyl)-4-ethoxymethyl-5-(1,3-thiazol-4-yl)pyrrolidine-2-carboxylic acid, 2-tert-butyl ester

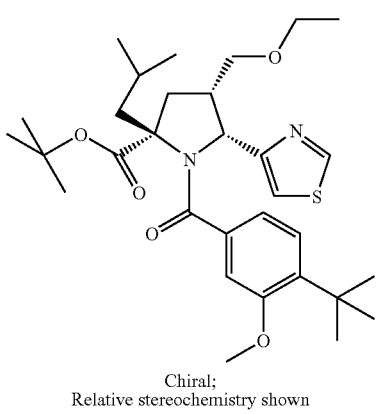

Chiral;
Relative stereochemistry shown

The enantiomers of Intermediate 78 were separated by preparative hplc on a Whelk-01 column, eluting with with heptane-ethanol (95:5 v/v) to give the title compound as the first eluting isomer.
MS calcd for $(C_{31}H_{46}N_2O_5S+H)^+$: 559
MS found (electrospray): $(M+H)^+=559$

Intermediate 80 rel-(4(2S,4S,5R)-2-Isobutyl-1-(3-methoxy-4-tert-butylbenzoyl)-4-allyloxymethyl-5-(1,3-thiazol-2-yl)pyrrolidine-2-carboxylic acid, tert-butyl ester

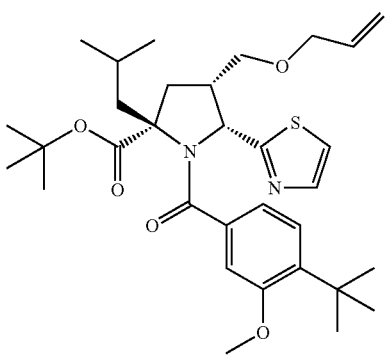

Racemic;
Relative stereochemistry shown

The title compound was prepared in a similar manner to Intermediate 14 replacing Intermediate 4 with Intermediate 4a.

MS calcd for $(C_{32}H_{46}N_2O_5S+H)+571$
MS found (electrospray): $(M+H)^+=571$

Intermediate 81 rel-(2S,4S,5R)-2-Isobutyl-1-(3-methoxy-4-tert-butylbenzoyl)-4-cyanomethyl-5-(1,3-thiazol-2-yl)pyrrolidine-2-carboxylic acid, tert-butyl ester

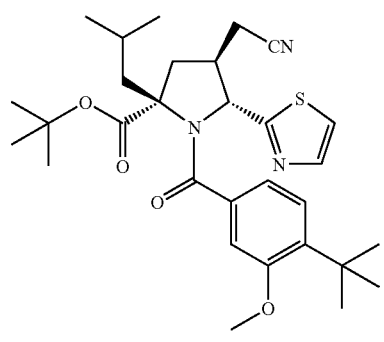

Racemic;
Relative stereochemistry shown

To a solution of trifluoromethanesulfonic anhydride (51 uL) in dry dichloromethane (2 mL) stirred under nitrogen at −15° C. was added a solution of intermediate 4 (159 mg) and pyridine (23 uL) in dichloromethane (2 mL). The mixture was stirred at 0° C. for 1.5 h. Water (5 mL) was added with vigorous stirring and the mixture was then passed through a hydrophobic frit. The dichloromethane solution so obtained was added to a solution of tetrabutylammonium cyanide (80 mg) in dichloromethane (2 mL) and stirred at room temperature for 3 h. The mixture was purified by chromatography on silica gel with cyclohexane-ethyl acetate (gradient elution from 4:1 v/v to 3:1 v/v) as eluent to give the title compound.

MS calcd for $(C_{30}H_{41}N_3O_4S+H)^+$: 540
MS found (electrospray): $(M+H)^+=540$

Intermediate 82

(2S,4S,5R)-2-Isobutyl-1-(3-methoxy-4-tert-butyl-benzoyl)-4-(1-hydroxy-1-methylethyl)-5-(1,3-thiazol-2-yl)pyrrolidine-2-carboxylic acid, tert-butyl ester

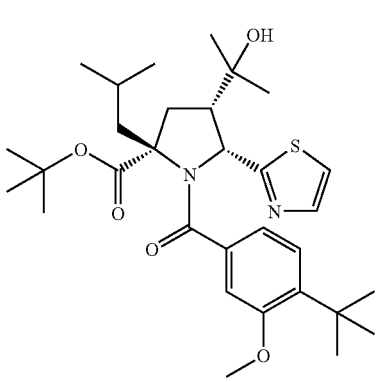

Chiral;
Relative stereochemistry shown

A solution of Intermediate 19 (280 mg) in tetrahydrofuran (10 mL) was stirred and cooled under nitrogen at −78° C. 1.4M methylmagnesium bromide solution in toluene/THF (2 mL) was added. The cooling bath was removed and the mixture was stirred for 2 h. Saturated ammonium chloride solution (10 mL) was added and the mixture was extracted with ethyl acetate (2×20 mL). The combined extracts were washed with water and brine and then dried (MgSO$_4$). Solvent was removed and the residue was purified by silica gel chromatography using cyclohexane-ethyl acetate (4:1 v/v) as eluent to give the title compound.

MS calcd for $(C_{31}H_{46}N_2O_5S+H)^+$: 559
MS found (electrospray): $(M+H)^+=559$

Intermediate 83 rel-(2S,4R,5R)-2-Isobutyl-1-(3-methoxy-4-tert-butylbenzoyl)-4-(1-hydroxyethyl)-5-(1,3-thiazol-2-yl_pyrrolidine-2-carboxylic acid, tert-butyl ester

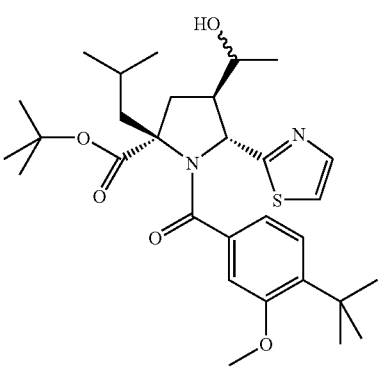

Racemic;
Relative stereochemistry shown

To a solution of Intermediate 11 (224 mg) in THF (3 mL) and ethanol (1 mL) was added sodium borohydride (31 mg)

and the resulting mixture was stirred at room temperature for 5 h. Solvent was removed and the residue was partitioned between ethyl acetate and water. The organic phase was collected and dried (MgSO$_4$). Removal of solvent gave the title compound as a 3:1 mixture of diastereoisomers.

MS calcd for (C$_{30}$H$_{44}$N$_2$O$_5$S+H)$^+$: 545
MS found (electrospray): (M+H)$^+$=545

Intermediate 84 rel-(2S,4R,5R)-2-Isobutyl-1-(3-methoxy-4-tert-butylbenzoyl)-4-(1-(4-fluorophenoxythiocarbonyloxy)ethyl)-5-(1,3-thiazol-2-yl)pyrrolidine-2-carboxylic acid, tert-butyl ester

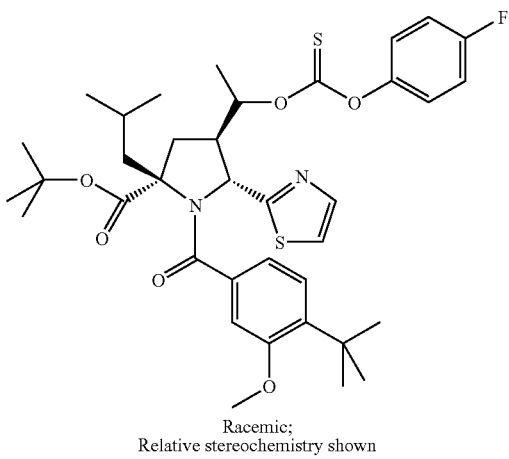

Racemic;
Relative stereochemistry shown

The title compound was prepared in a similar manner to Intermediate 8, using Intermediate 83 as starting material.

MS calcd for (C$_{37}$H$_{47}$FN$_2$O$_6$S$_2$+H)$^+$: 699
MS found (electrospray): (M+H)$^+$=699

Intermediate 85 rel-(2S,4R,5R)-2-Isobutyl-1-(3-methoxy-4-tert-butylbenzoyl)-4-ethyl-54(1,3-thiazol-2-yl)pyrrolidine-2-carboxylic acid, tert-butyl ester

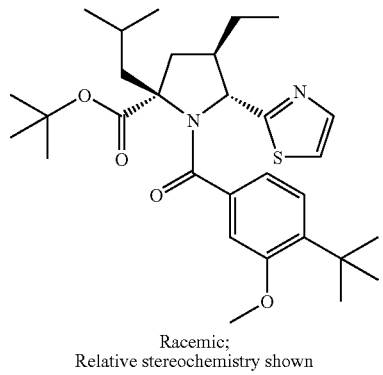

Racemic;
Relative stereochemistry shown

To a solution of Intermediate 84 (152 mg) in 1,4-dioxan (3 mL) was added AIBN (14 mg) and tris(trimethylsilyl) silane (0.089 mL). The mixture was heated at 115° C. for 3.75 h and then set aside at room temperature overnight. The mixture was further heated at 115° C. for 2 h. Solvent was evaporated and the residue was purified by silica gel chromatography eluting with cyclohexane-ethyl acetate (9:1 v/v) to give the title compound as a gum.

MS calcd for (C$_{30}$H$_{44}$N$_2$O$_4$S+H)$^+$: 529
MS found (electrospray): (M+H)$^+$=529

Intermediate 86 rel-(2S,4R,5R)-2-Isobutyl-1-(3-methoxy-4-tert-butylbenzoyl)-5-(pyridin-2-yl)pyrrolidine-2,4-dicarboxylic acid, 2-tert-butyl ester, 4-methyl ester

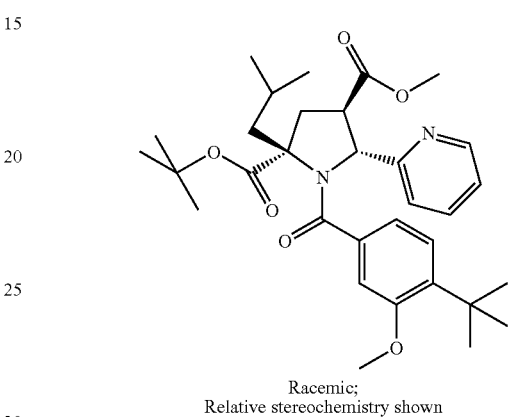

Racemic;
Relative stereochemistry shown

To a solution of Intermediate 67 (1.29 g) in methanol (15 mL) was added 25% w/v methanolic sodium methoxide (0.51 mL). The mixture was stirred at room temperature overnight. Solvent was removed and the residue was purified by silica chromatography eluting with cyclohexane-ethyl acetate (4:1 v/v) to give the title compound.

MS calcd for (C$_{32}$H$_{44}$N$_2$O$_6$+H)$^+$: 553
MS found (electrospray): (M+H)$^+$=553

Intermediate 87 rel-(2S,4R,5R)-2-Isobutyl-1-(3-methoxy-4-tert-butylbenzoyl)-4-hydroxymethyl-5-(pyridin-2-yl)pyrrolidine-2-carboxylic acid, 2-tert-butyl ester

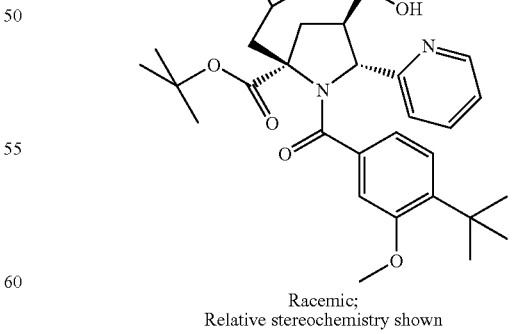

Racemic;
Relative stereochemistry shown

To a solution of Intermediate 86 (758 mg) in tetrahydrofuran (10 mL) was added 2M lithium borohydridfe solution in tetrahydrofuran (0.98 mL). The mixture was stirred at room temperature for 18 h. Solvent was removed and the residue was partitioned between ethyl acetate and potassium carbonate solution. The organic layer was collected and the aqueous layer further extracted with ethyl acetate. The combined organic solutions were dried (Na$_2$SO$_4$). Solvent was removed and the residue was purified by silica gel chromatography eluting with cyclohexane-ethyl acetate (gradient elution from 100:0 v/v to 3:2 v/v) to give the title compound.

MS calcd for (C$_{31}$H$_{44}$N$_2$O$_5$+H)$^+$: 525
MS found (electrospray): (M+H)$^+$=525

Intermediate 88 rel-(2S,4R,5R)-2-Isobutyl-1-(3-methoxy-4-tert-butylbenzoyl)-4-methoxymethyl-5-(pyridin-2-yl)pyrrolidine-2-carboxylic acid, 2-tert-butyl ester

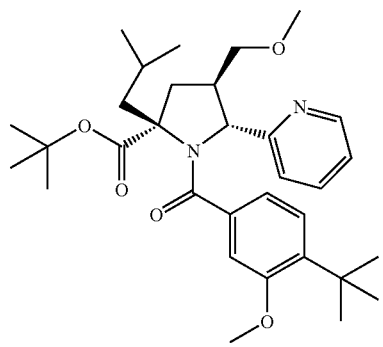

Racemic;
Relative stereochemistry shown

The title compound was prepared in a similar manner to Intermediate 16, using Intermediate 87 as starting material.

MS calcd for (C$_{32}$H$_{46}$N$_2$O$_5$+H)$^+$: 539
MS found (electrospray): (M+H)$^+$=539

Intermediate 89

(2S,4S,5R)-2-(Isobutyl)-5-(1,3-thiazol-2-yl)pyrrolidine-2,4-dicarboxylic acid, 2-(tert-butyl) ester, 4-[(1R,2S,5R)-5-methyl-2-(isopropyl)cyclohexyl] ester

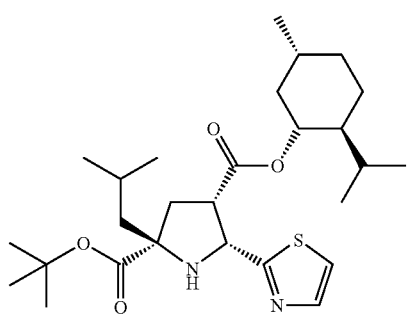

Diastereoisomer ratio 85:15 (chiral hplc)
Major diastereoisomer shown
Absolute stereochemistry shown L-menthyl acrylate (11.24 g, 53.5 mmol) was added to a solution of (Intermediate 1; 13.73 g, 48.6 mmol) in anhydrous THF (165 mL). Lithium bromide (8.43 g, 97.1 mmol) was added and the mixture stirred for 5 minutes prior to the dropwise addition of triethylamine (10.11 mL, 72.9 mmol). The resulting mixture was stirred at room temperature under nitrogen for 18 hours then quenched with saturated aqueous ammonium chloride solution, extracted into ethyl acetate and washed with brine, dried (Na$_2$SO$_4$) and evaporated to afford the title compound as a dark red oil, a mixture of diastereoisomers at the pyrrolidine C(4)-centre. The absolute stereochemistry of the major diastereoisomer was confirmed by reference to Intermediate 90 (below).

MS calcd. for (C$_{27}$H$_{44}$N$_2$O$_4$S+H)$^+$: 493.
MS found (electrospray): (M+H)$^+$=493

$^1$H NMR (DMSO-d$_6$): δ 7.64 (1H, d), 7.60 (1H, d), 4.72 (1H, t), 4.32 (1H, m), 3.42 (1H, m), 2.46 (1H, dd), 2.02 (1H, dd), 1.71-1.48 (6H, m), 1.41 (9H, s), 1.38-1.10 (3H, m), 0.97-0.47 (4H, br), 0.91 (3H, d), 0.84 (3H, d), 0.78 (6H, d), 0.58 (3H, d).

Intermediate 90

(2S,4S,5R)-2-(Isobutyl)-5-(1,3-thiazol-2-yl)pyrrolidine-2,4-dicarboxylic acid, 2-(tert-butyl) ester, 4-[(1R,2S,5R)-5-methyl-2-(isopropyl)cyclohexyl] ester hydrochloride

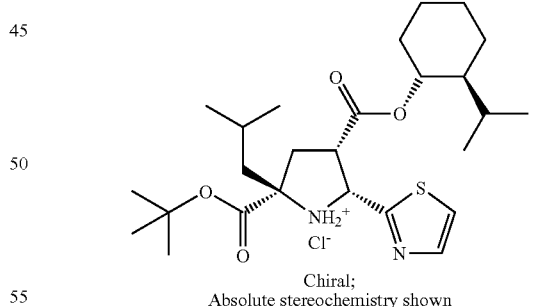

Chiral;
Absolute stereochemistry shown
Stereochemistry determined by X-ray crystallography Anhydrous hydrogen chloride (1M in diethyl ether) (75.9 mL, 75.9 mmol) was added dropwise to a solution of Intermediate 89 (24.84 g, 50.4 mmol) in diethyl ether at 0° C. The solvent was removed under reduced pressure and the resulting solid was recrystallised from 2-propanol. The resulting solid was washed with diethyl ether and dried to give the title compound as a crystalline solid.

¹H NMR (CD₃OD): δ 7.78 (d, 1H), 7.76 (d, 1H), 5.56 (d, 1H), 4.53 (m, 1H), 3.84 (dd, 1H), 3.42 (dd, 1H), 2.53 (dd, 1H), 2.11-2.01 (m, 2H), 1.85-1.70 (m, 2H), 1.69-1.60 (br m, 2H), 1.53 (s, 9H), 1.45-1.23 (br m, 3H), 1.07-0.95 (m, 1H), 1.03 (d, 3H), 1.00 (d, 3H), 0.89 (d, 3H), 0.83 (d, 3H), 0.80-0.72 (br m, 1H), 0.70 (d, 3H) 0.50 (dd, 1H).

The absolute stereochemistry of this compound was determined by X-ray crystallography and shown to be (2S,4S, 5R), as drawn.

Intermediate 91

(2S,4S,5R)-2-isobutyl-1-(3-methoxy-4-tert-butylbenzoyl)-5-(1,3-thiazol-2-yl) pyrrolidine-2,4-dicarboxylic acid, 2-(tert-butyl)ester, 4-[(1R,2S,5R)-5-methyl-2-(isopropyl)cyclohexyl]ester

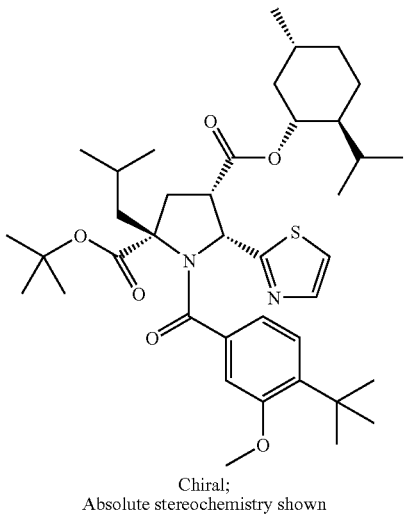

Chiral;
Absolute stereochemistry shown

Triethylamine (6.16 mL, 44.4 mmol) was added dropwise to a solution of Intermediate 90; 11.75 g, 22.20 mmol) and 4-tert-butyl-3-methoxybenzoyl chloride (7.57 g, 33.4 mmol) in anhydrous dichloromethane (190 mL). The reaction mixture was stirred at room temperature under nitrogen for 18 hours, washed with saturated aqueous sodium bicarbonate solution, dried (hydrophobic frit) and concentrated in vacuo. The crude product mixture was purified by chromatography on silica gel using toluene then cyclohexane-ethyl acetate (1:1 v/v) as eluent to afford the title compound as a gum.

MS calcd. for $(C_{39}H_{58}N_2O_6S+H)^+$: 683.

MS found (electrospray): $(M+H)^+$=683.

¹H NMR (CD₃OD): δ 7.42 (s, 1H), 7.28 (d, 1H), 6.86 (d, 1H), 6.51 (s, 1H), 5.85 (d, 1H), 4.39 (m, 1H), 3.92 (m, 1H), 3.67 (s, 3H), 3.06 (dd, 1H), 2.41 (dd, 1H), 2.26-2.11 (m, 2H), 2.09-1.90 (m, 1H), 1.89-1.74 (br, 1H), 1.66-1.52 (br, 2H), 1.47 (s, 9H), 1.35 (s, 9H), 1.38-1.11 (br, 4H), 1.08 (d, 6H), 1.06-0.89 (br, 1H), 0.86 (d, 3H), 0.82-0.67 (br, 1H), 0.76 (d, 3H), 0.66 (d, 3H), 0.51-0.35 (q, 1H).

Intermediate 92

(2S,4S,5R)-2-Isobutyl-1-(3-methoxy-4-tert-butyl-benzoyl)-4-(hydroxymethyl)-5-(1,3-thiazol-2-yl) pyrrolidine-2-carboxylic acid, tert-butyl ester

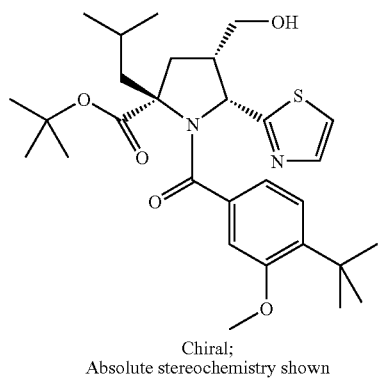

Chiral;
Absolute stereochemistry shown

Lithium aluminiumhydride (1M in tetrahydrofuran) (0.22 mL, 0.22 mmol) was added dropwise over 1 minute to a solution of Intermediate 91 (0.15 g, 0.22 mmol) in anhydrous diethyl ether (3 mL) at room temperature under nitrogen. The reaction mixture was quenched after 10 minutes by dropwise addition of 1.0 M aqueous potassium carbonate and extracted twice into ethyl acetate. The extracts were combined, washed with water, dried (Na₂SO₄) and evaporated to afford a gum. The crude product was purified by chromatography on silica gel using cyclohexane-ethyl acetate (2:1 v/v) as eluent to give the title compound.

MS calcd. for $(C_{29}H_{42}N_2O_5S+H)^+$: 531.

MS found (electrospray): $(M+H)^+$=531.

¹H NMR (CDCl₃): 7.57 (d, 1H), 7.27 (d, 1H), 7.09 (d, 1H), 6.69 (d, 1H), 6.53 (s, 1H), 5.64 (d, 1H), 3.59 (s, 3H), 3.43 (dd, 1H), 3.26-3.12 (br, 1H), 2.80 (t, 1H), 2.34 (dd, 1H), 2.22-1.82 (m, 4H), 1.59 (s, 9H), 1.52-1.30 (m, 1H), (s, 9H), 1.06 (m, 6H).

This compound was spectroscopically identical to that described in Intermediate 20.

Intermediate 93

Enantiomer A of rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid, 2-tert-butyl ester

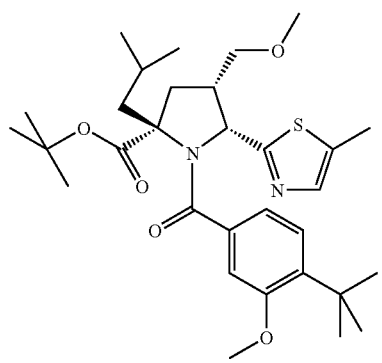

Chiral; Enantiomer A
Absolute stereochemistry shown

Intermediate 51 was separated into enantiomers using chiral hplc on a Chiralpak AD column and eluting with heptane-isopropyl alcohol (95:5 v/v). The title compound was obtained as the first eluting enantiomer.

MS calcd for $(C_{31}H_{46}N_2O_5S+H)^+$: 559

MS found (electrospray): $(M+H)^+=559$

Intermediate 94 and 95

Diastereoisomer 1 and diastereoisomer 2 of rel-(2S, 4R,5R)-2-Isobutyl-1-(3-methoxy-4-tert-butylbenzoyl)-4-(1-methoxyethyl)-5-(1,3-thiazol-2-yl)pyrrolidine-2-carboxylic acid, tert-butyl ester

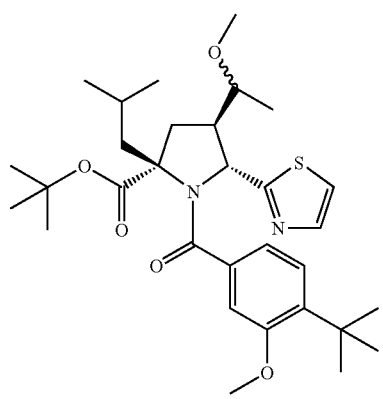

Racemic
Relative stereochemistry shown
Diastereoisomer 1 - Intermediate 94
Diastereoisomer 2 - Intermediate 95

To a stirred solution of Intermediate 83 (0.84 g, 1.54 mmol) (7:3 mixture of diastereoisomeric alcohols) in anhydrous DMF (15 mL) was added sodium hydride (60% dispersion in mineral oil; 0.15 g, 3.64 mmol). The resultant mixture was stirred at room temperature for 1 h and then iodomethane (0.75 mL, 12.05 mmol) was added with stirring. After 1 h the reaction mixture was partitioned between ethyl acetate and 1N hydrochloric acid. The aqueous phase was separated off and was back extracted once with ethyl acetate. The organic phases were combined dried ($Na_2SO_4$) and evaporated to leave a gum. This material was pre-absorbed onto silica gel prior to chromatography on silica gel using cyclohexane-ethyl acetate (7:1 v/v) as eluent. Early fractions were combined and then evaporated to give Intermediate 94.

MS calcd. for $(C_{31}H_{46}N_2O_5S+H)^+$: 559.

MS found (electrospray): $(M+H)^+=559$.

Later fractions were combined and evaporated to give Intermediate 95.

MS calcd. for $(C_{31}H_{46}N_2O_5S+H)^+$: 559.

MS found (electrospray): $(M+H)=559$

Intermediate 96

Enantiomer A of (2S,4S,5R)-2-Isobutyl-1-(3-methoxy-4-tert-butylbenzoyl)-4-methoxy methyl-5-(pyridin-2-yl)pyrrolidine-2-carboxylic acid, 2-tert-butyl ester

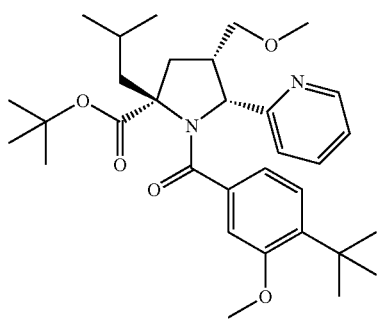

Chiral; Enantiomer A
Relative stereochemistry shown

To a stirred solution of intermediate 68 (845 mg, 1.6 mmol) in anhydrous DMF (30 mL) was added sodium hydride (60% in mineral oil, 64 mg, 1.6 mmol) under nitrogen at −15° C. The slurry was stirred at −15° C. for 30 min, then methyl iodide (0.1 mL, 227 mg, 1 eq) was added and the reaction stirred and allowed to warm from −15° C. to room temp over 18 hours. Methanol (30 mL) was added and the reaction stirred for 15 min. The solvent was evaporated and the residue partitioned between water and ethyl acetate. The organic layer was dried with $Na_2SO_4$ and evaporated to give an oil, which was purified by chromatography on silica gel using a cyclohexane-ethyl acetate gradient elution, affording a solid. This was separated into its enantiomers using preparative chiral HPLC on a Welk 01 column, eluting with heptane-isopropanol (95:5 v/v). The title compound was obtained as the first eluting enantiomer.

MS calcd for $(C_{32}H_{46}N_2O_5+H)^+$: 539

MS found (electrospray): $(M+H)^+=539$

Intermediate 97

2-[N-(5-Methylisoxazol-3-ylmethylene)amino]-4-methylpentanoic acid, tert-butyl ester

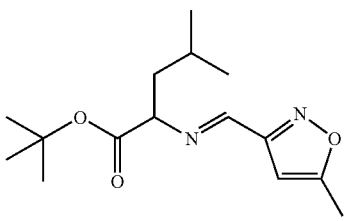

The title compound was prepared in a similar manner to Intermediate 1, using 5-methyl-isoxazole-3-carboxaldehyde in place of 1,3-thiazole-2-carboxaldehyde.

$^1$H NMR ($CDCl_3$): δ 8.35 (1H, s), 6.48 (1H, s), 4.00 (1H, m), 2.45 (3H, s), 1.79 (2H, m), 1.53 (1H, m), 1.46 (9H, s), 0.98 (3H, dd), 0.89 (3H, dd)

Intermediate 98 rel-(2S,4S,5R)-2-isobutyl-5-(5-methylisoxazol-3-yl)pyrrolidine-2,4-dicarboxylic acid, 2-tert-butyl ester, 4-methyl ester

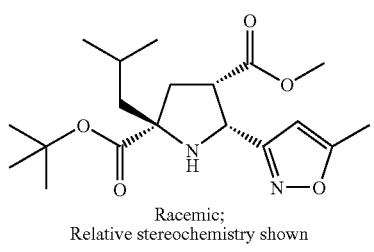

Racemic;
Relative stereochemistry shown

The title compound was prepared in a similar manner to Intermediate 2, using Intermediate 97 as starting material.
MS calcd for $(C_{19}H_{30}N_2O_5+H)^+$: 367
MS found (electrospray): $(M+H)^+=367$

Intermediate 99 rel-(2S,4S,5R)-2-isobutyl-1-(3-methoxy-4-tert-butyl-benzoyl)-5-(5-methyl-1,2-oxazol-3-yl)-pyrrolidine-2,4-dicarboxylic acid, 2-tert-butyl ester, 4-methyl ester

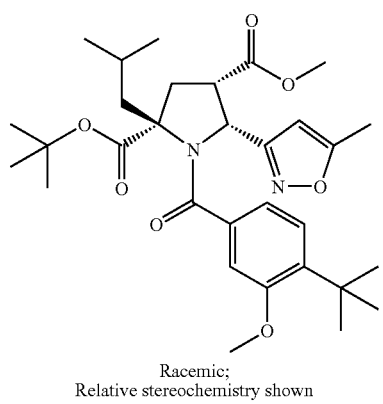

Racemic;
Relative stereochemistry shown

The title compound was prepared in a similar manner to Intermediate 3, using Intermediate 98 as starting material.
MS calcd for $(C_{31}H_{44}N_2O_7+H)^+$: 557
MS found (electrospray): (M+H)=557

Intermediate 100 rel-(2S,4S,5R)-2-Isobutyl-1-(3-methoxy-4-tert-butyl-benzoyl)-4-hydroxymethyl-5-(5-methylisoxazol-3-yl)pyrrolidine-2-carboxylic acid, tert-butyl ester

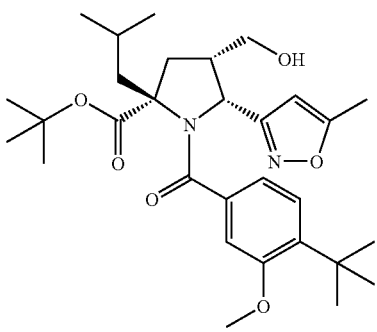

Racemic;
Relative stereochemistry shown

The title compound was prepared in a similar manner to Intermediate 20, using Intermediate 99 as starting material.
MS calcd for $(C_{30}H_{44}N_2O_6+H)^+$: 529
MS found (electrospray): $(M+H)^+=529$

Intermediate 101 rel-(2S,4S,5R)-2-Isobutyl-1-(3-methoxy-4-tert-butyl-benzoyl)-4-ethoxymethyl-5-(5-methylisoxazol-3-yl)pyrrolidine-2-carboxylic acid, tert-butyl ester

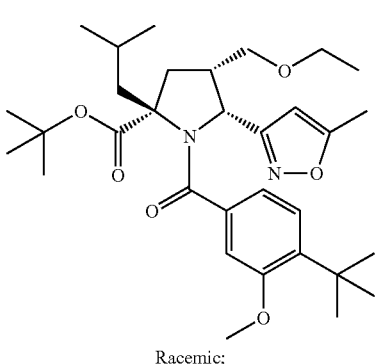

Racemic;
Relative stereochemistry shown

The title compound was prepared in a similar manner to Intermediate 16, using Intermediate 100 as starting material.
MS calcd for $(C_{32}H_{48}N_2O_6+H)^+$: 557
MS found (electrospray): $(M+H)^+=557$ Intermediate 102

Enantiomer A of rel-(2S,4S,5R)-2-Isobutyl-1-(3-methoxy-4-tert-butylbenzoyl)-4-ethoxymethyl-5-(5-methylisoxazol-3-yl)pyrrolidine-2-carboxylic acid, tert-butyl ester

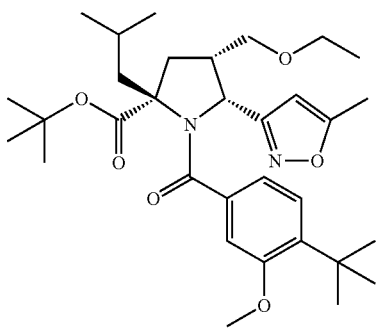

Chiral; Enantiomer A
Relative stereochemistry shown

Intermediate 101 was separated into its enantiomers by preparative chiral hplc on a Whelko-1 column and eluting with heptane-ethanol (90:10 v/v). The title compound was obtained as the first eluting enantiomer.
MS calcd for $(C_{32}H_{48}N_2O_6+H)^+$: 557
MS found (electrospray): $(M+H)^+=557$ Intermediate 103

2-Bromo-1,3-thiazole-5-carboxaldehyde

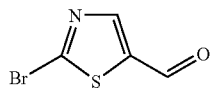

2-Amino-1,3-thiazole-5-carboxaldehyde (13.78 g, 0.108 mol, 1 eq) in acetonitrile (200 mL) (slurry) was added portionwise to a stirred suspension of $CuBr_2$ (36.03 g, 0.129 mol) and t-butyl nitrite (19 mL, 0.161 mL) in acetonitrile (550 mL). The reaction was stirred at room temperature for 4 hours then evaporated to give a solid. This was treated with ethyl acetate (400 mL) and 2M HCl (400 mL). Water (200 mL), brine (100 mL) and ethyl acetate (200 mL) were added. The phases were separated. The aqueous phase was extracted with ethyl acetate (250 mL). The combined organic layers were dried ($MgSO_4$) and evaporated to give the title compound.
$^1$H NMR ($CDCl_3$): δ 9.97 (1H, s), 8.19 (1H, s)

Intermediate 104

(2-bromo-1,3-thiazol-5-yl)methanol

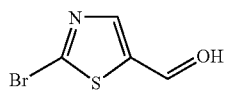

Intermediate 103 (16.34 g, 0.086 mol) was dissolved in methanol (300 mL) and cooled to 10° C. Sodium borohydride (1.63 g, 0.043 mol) was added portionwise over 15 min. The cooling bath was removed and the reaction allowed to warm to room temperature and stirred for 3 hours. The solvent was evaporated. Water (100 mL) was added followed by 1N HCl (200 mL). Ethyl acetate (450 mL) was added and the phases were separated. The organic layer was washed with brine (450 mL), dried ($MgSO_4$) and concentrated to give a brown liquid. The crude product was purified by chromatography on silica, using cyclohexane-ethyl acetate (80:20 v/v) as eluent to give the title compound.
$^1$H NMR ($CDCl_3$): δ 7.4 (1H, s), 4.82 (2H, d), 2.96 (1H, t)

Intermediate 105

2-bromo-5-(methoxymethyl)-1,3-thiazole

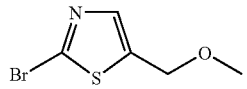

Intermediate 104 (10.58 g, 54.80 mmol) was dissolved in DMF (250 mL) and the solution cooled to −15° C. under nitrogen. Sodium hydride (60% dispersion in oil; 3.29 g, 82.20 mmol) was added and the mixture stirred between −15° C. and −10° C. for 25 min. Methyl iodide (6.82 mL, 0.109 mol) was added and the solution was stirred between −15° C. and −10° C. for 4 hours. The reaction was quenched by addition of methanol (50 mL). The methanol was removed in vacuo, and the residue diluted with water (600 mL) and extracted twice with ether. The organic layer was washed twice with water, dried ($MgSO_4$), and concentrated to give a liquid. The crude product was purified by chromatography on silica gel, using cyclohexane-ethyl acetate (90:10 v/v) as eluent to give the title compound.
$^1$H NMR ($CDCl_3$): δ 7.45 (1H, s), 4.58 (2H, s), 3.37 (3H, s)

Intermediate 106

5-(Methoxymethyl)-1,3-thiazole-2-carboxaldehyde

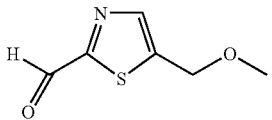

An oven dried 3 necked flask was purged with nitrogen and charged with n-BuLi (1.6 M solution in hexanes; 21.80 mL, 34.54 mmol) followed by dry diethyl ether (42 mL). The solution was cooled in an ice/acetone bath to −78° C. and a solution of Intermediate 105 (7.01 g, 33.86 mmol) in diethyl ether (28 mL) was added dropwise over a period of 20 min, maintaining the internal temperature below −68° C. The resultant reaction mixture was stirred at −78° C. for 20 min. Anhydrous DMF (3.9 mL, 50.79 mmol) was added in one portion. The reaction was allowed to warm slowly over 4 hours to 15° C. The reaction was carefully quenched by adding 4N hydrochloric acid (50 mL), not allowing the temperature to rise above 20° C. Ice/water was added followed by diethyl ether (140 mL). The mixture was extracted with 4N hydrochloric acid (4×70 mL). and the resultant aqueous extracts combined. These extracts were then neutralised to pH 7 using sodium hydrogen carbonate and the resultant aqueous phase was extracted with diethyl ether (2×140 mL). The diethyl ether extracts were combined, dried (MgSO$_4$) and evaporated with care under vacuo, to give a liquid. The crude product was purified by chromatography on silica gel using cyclohexane-ethyl acetate (80:20 v/v) as eluent to give the title compound.

$^1$H NMR (CDCl$_3$): δ 9.95 (1H, s), 7.98 (1H, s), 4.72 (2H, s), 3.44 (3H, s).

Intermediate 107

2-[N-(5-Methoxymethyl-1,3-thiazol-2-ylmethylene)amino]-4-methylpentanoic acid, tert-butyl ester

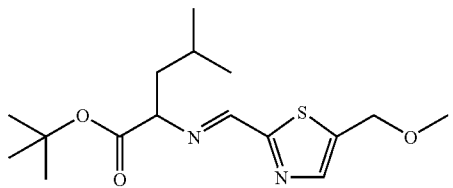

The title compound was prepared in a similar manner to Intermediate 1, using Intermediate 106 in place of 1,3-thiazole-2-carboxaldehyde.

$^1$H NMR (CDCl$_3$): δ 8.36 (1H, s), 7.79 (1H, s), 4.65 (2H, s), 4.48-4.01 (1H, m), 3.39 (3H, s), 1.89-1.71, (2H, m), 1.63-1.50 (1H, m), 1.47 (9H, s), 0.94 (3H, d), 0.89 (3H, d)

Intermediate 108 rel-(2S,4S,5R)-2-isobutyl-5-(5-methoxymethyl-1,3-thiazol-2-yl)pyrrolidine-2,4-dicarboxylic acid, 2-tert-butyl ester, 4-methyl ester

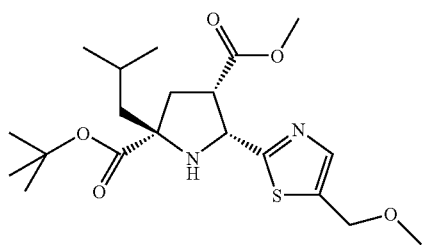

Racemic;
Relative stereochemistry shown

The title compound was prepared in a similar manner to Intermediate 2, using Intermediate 107 as starting material.

MS calcd for (C$_{20}$H$_{32}$N$_2$O$_5$S+H)$^+$: 413
MS found (electrospray): (M+H)$^+$=413

Intermediate 109 rel-(2S,4S,5R)-2-isobutyl-1-(3-methoxy-4-tert-butyl-benzoyl)-5-(5-methoxymethyl-1,3-thiazol-2-yl)pyrrolidine-2,4-dicarboxylic acid, 2-tert-butyl ester, 4-methyl ester

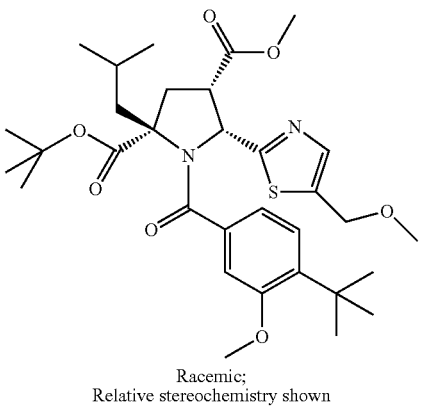

Racemic;
Relative stereochemistry shown

The title compound was prepared in a similar manner to Intermediate 3, using Intermediate 108 as starting material.

MS calcd for (C$_{32}$H$_{46}$N$_2$O$_7$S+H)$^+$: 603
MS found (electrospray): (M+H)$^+$=603

Intermediate 110 rel-(2S,4S,5R)-2-Isobutyl-1-(3-methoxy-4-tert-butyl-benzoyl)-4-hydroxymethyl-5-(5-methoxymethyl-1,3-thiazol-2-yl)pyrrolidine-2-carboxylic acid, tert-butyl ester

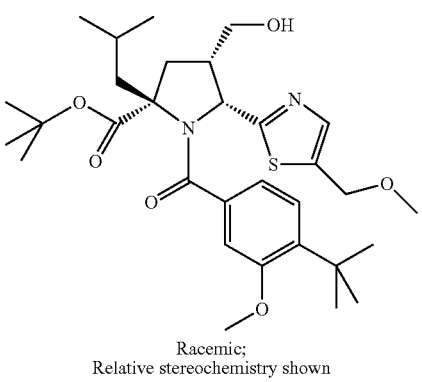

Racemic;
Relative stereochemistry shown

The title compound was prepared in a similar manner to Intermediate 20, using Intermediate 109 as starting material.

MS calcd for (C$_{31}$H$_{46}$N$_2$O$_6$S+H)$^+$: 575
MS found (electrospray): (M+H)$^+$=575

Intermediate 111 rel-(2S,4S,5R)-2-Isobutyl-1-(3-methoxy-4-tert-butyl-benzoyl)-4-methoxymethyl-5-(5-methoxymethyl-1,3-thiazol-2-yl)pyrrolidine-2-carboxylic acid, tert-butyl ester

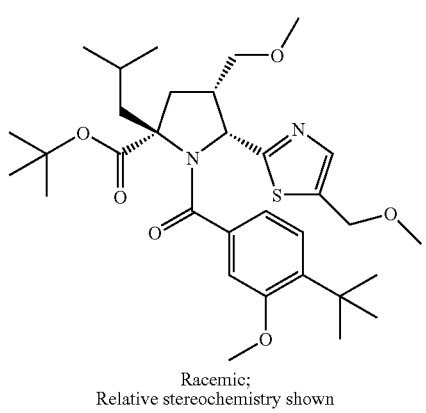

Racemic;
Relative stereochemistry shown

The title compound was prepared in a similar manner to Intermediate 16, using Intermediate 110 as starting material.
MS calcd for $(C_{32}H_{48}N_2O_6S+H)^+$: 589
MS found (electrospray): $(M+H)^+=589$

Intermediate 112

2-[N-(5-Methylpyridin-2-ylmethylene)amino]4-methylpentanoic acid, tert-butyl eser

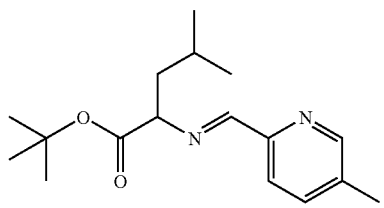

The title compound was prepared in a similar manner to Intermediate 1, using 5-methylpyridine-2-carboxaldehyde in place of 1,3-thiazole-2-carboxaldehyde.
$^1$H NMR (CDCl3): δ 8.47 (1H, s), 8.33 (1H, s), 8.02 (1H, d), 7.55 (1H, d), 4.02 (1H, m), 2.37 (3H, s), 1.72-1.9 (2H, m), 1.47-1.64 (1H, m), 1.47 (9H, s), 0.94 (3H, d), 0.89 (3H, d).

Intermediate 113 rel-(2S,4S,5R)-2-isobutyl-S-(5-methylpyridin-2-yl)pyrrolidine-2,4-dicarboxylic acid, 2-tert-butyl ester, 4-methyl ester

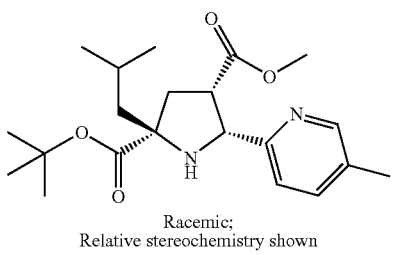

Racemic;
Relative stereochemistry shown

The title compound was prepared in a similar manner to Intermediate 2, using Intermediate 112 as starting material.
MS calcd for $(C_{21}H_{32}N_2O_4+H)^+$: 377
MS found (electrospray): $(M+H)^+=377$

Intermediate 114 rel-(2S,4S,5R)-2-Isobutyl-1-(3-methoxy-4-tert-butyl-benzoyl)-5-(5-methylpyridin-2-yl)-pyrrolidine-2,4-dicarboxylic acid, 2-tert-butyl ester, 4-methyl ester

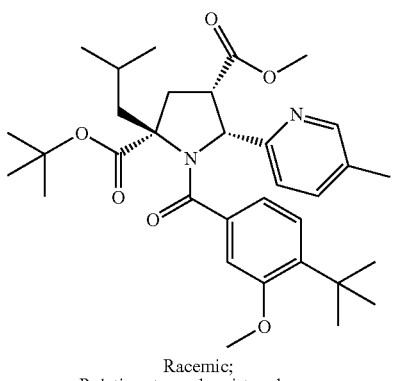

Racemic;
Relative stereochemistry shown

The title compound was prepared in a similar manner to Intermediate 3, using Intermediate 113 as starting material.
MS calcd for $(C_{33}H_{46}N_2O_6+H)^+$: 567
MS found (electrospray): $(M+H)^+=567$

85

Intermediate 115 rel-(2S,4S,5R)-2-Isobutyl-1-(3-methoxy-4-tert-butyl-benzoyl)-4-hydroxymethyl-5-(5-methylpyridin-2-yl)pyrrolidine-2-carboxylic acid, tert-butyl ester

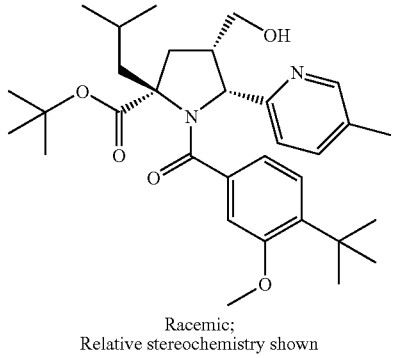

Racemic;
Relative stereochemistry shown

The title compound was prepared in a similar manner to Intermediate 20, using Intermediate 114 as starting material.

MS calcd for $(C_{32}H_{46}N_2O_5+H)^+$: 539
MS found (electrospray): $(M+H)^+=539$ Intermediate 116 rel-(2S,4S,5R)-2-Isobutyl-1-(3-methoxy-4-tert-butyl-benzoyl)-4-methoxymethyl-5-(5-methylpyridin-2-yl)pyrrolidine-2-carboxylic acid, tert-butyl ester

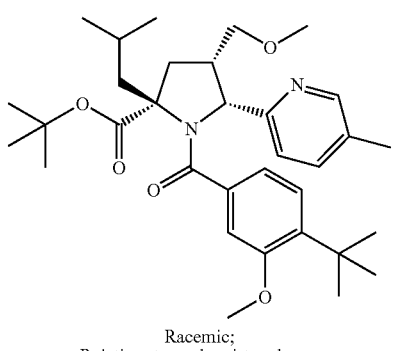

Racemic;
Relative stereochemistry shown

The title compound was prepared in a similar manner to Intermediate 16, using Intermediate 115 as starting material.

MS calcd for $(C_{33}H_{48}N_2O_5+H)^+$: 553
MS found (electrospray): $(M+H)^+=553$

86

Intermediate 117

2-[N-(Thien-2-ylmethylene)amino]-4-methylpentanoic acid, tert-butyl ester

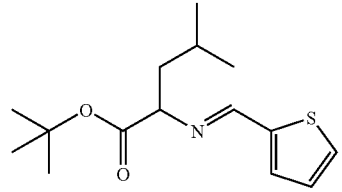

The title compound was prepared in a similar manner to Intermediate 1, using thiophene-2-carboxaldehyde in place of 1,3-thiazole-2-carboxaldehyde.

$^1$H NMR (CDCl$_3$): δ 8.88 (s, 1H), 7.43 (dd, 1H), 7.35 (dd, 1H), 7.08 (dd, 1H), 3.94 (dd, 1H), 1.86-1.72 (m, 2H), 1.63-1.53 (m, 1H), 1.47 (s, 9H), 0.95 (d, 3H), 0.90 (d, 3H).

Intermediate 118 rel-(2S,4S,5R)-2-Isobutyl-5-(thien-2-yl)pyrrolidine-2,4-dicarboxylic acid, 2-tert-butyl ester, 4-methyl ester

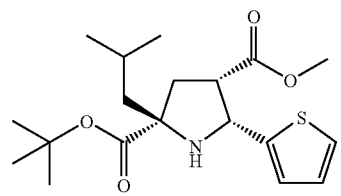

Racemic;
Relative stereochemistry shown

The title compound was prepared in a similar manner to Intermediate 2, using Intermediate 117 as starting material.

MS calcd for $(C_{19}H_{29}NO_4S+H)^+$: 368
MS found (electrospray) $(M+H)^+$: 368

Intermediate 119 rel-(2S,4S,5R)-2-Isobutyl-1-(3-methoxy-4-tert-butyl-benzoyl)-5-(thien-2-yl)pyrrolidine-2,4-dicarboxylic acid, 2-tert-butyl ester, 4-methyl ester

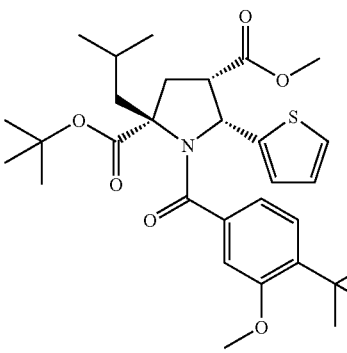

Racemic;
Relative stereochemistry shown

The title compound was prepared in a similar manner to Intermediate 3, using Intermediate 118 as starting material.

MS calcd for $(C_{31}H_{43}NO_6S+H)^+$: 558
MS found (electrospray) $(M+H)^+$: 558

Intermediate 120 rel-(2S,4S,5R)-2-isobutyl-1-(3-methoxy-4-tert-butyl-benzoyl)-4-hydroxymethyl-5-(thien-2-yl)pyrrolidine-2-carboxylic acid, tert-butyl ester

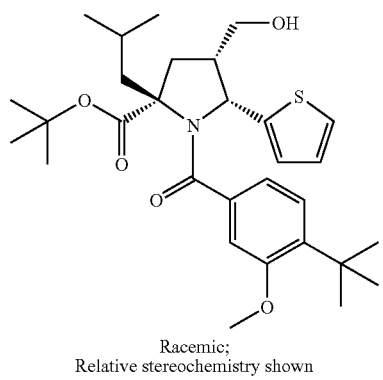

Racemic;
Relative stereochemistry shown

The title compound was prepared in a similar manner to Intermediate 20, using Intermediate 119 as starting material.

MS calcd for $(C_{30}H_{43}NO_5S+H)^+$: 530
MS found (electrospray) $(M+H)^+$: 530

Intermediate 121 rel-(2S,4S,5R)-2-isobutyl-1 (3-methoxy-4-tert-butyl-benzoyl)-4-methoxymethyl-5-(thien-2-yl)pyrrolidine-2-carboxylic acid, tert-butyl ester

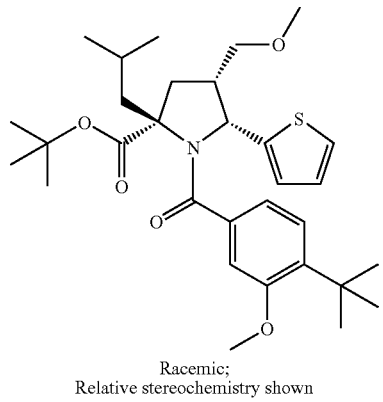

Racemic;
Relative stereochemistry shown

The title compound was prepared in a similar manner to Intermediate 16, using Intermediate 120 as starting material.

MS calcd for $(C_{31}H_{45}NO_5S+H)^+$: 544
MS found (electrospray) $(M+H)^+$: 544

EXAMPLE 1 rel-(2S,4R,5R)-2-isobutyl-1-(3-methoxy-4-tert-butylbenzoyl)-4-ethoxymethyl-5-(1,3-thiazol-2-yl)pyrrolidine-2-carboxylic acid

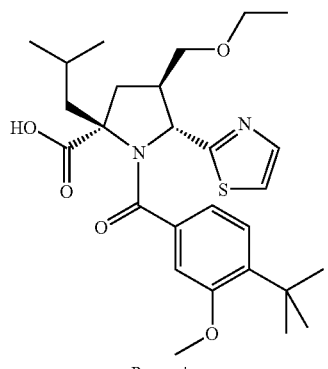

Racemic;
Relative stereochemistry shown

To a solution of Intermediate 5 (0.053 g) in anhydrous dichloromethane (1 mL) was added trifluoroacetic acid (1 mL). The mixture was stored at 20° C. temperature overnight. The mixture was evaporated and the residue was triturated with ether to give the title compound as a solid.

MS calcd for $(C_{27}H_{38}N_2O_5S+H)^+$: 503
MS found (electrospray): $(M+H)^+$=503

$^1$H NMR (CD$_3$OD): δ 7.37 (1H, d), 7.23 (1H, br s), 7.14 (1H, d), 6.85 (1H, s), 6.54 (1H, s), 5.37 (1H, d), 3.70 (3H, s), 3.34-3.47 (4H, m), 2.79 (1H, m), 2.50 (2H, m), 2.31 (1H, dd), 1.98 (1H, dd), 1.86 (1H, m), 1.30 (9H, s), 1.13 (3H, d), 1.12 (3H, t), 1.00 (3H, d).

EXAMPLE 2 rel-2S,4R,5R)-2-isobutyl-1-(3-methoxy-4-tert-butylbenzoyl)-4-methoxymethyl-5-(1,3-thiazol-2-yl)pyrrolidine-2-carboxylic acid

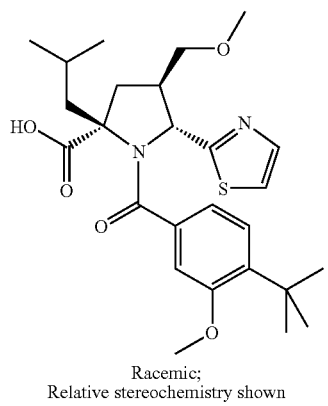

Racemic;
Relative stereochemistry shown

The title compound was prepared in a similar manner to Example 1 from Intermediate 6.

MS calcd for $(C_{26}H_{36}N_2O_5S+H)^+$: 489
MS found (electrospray): $(M+H)^+$=489

¹H NMR (CD₃OD): δ 7.40 (1H, d), 7.26 (1H, br s), 7.17 (1H, d), 6.89 (1H, d), 6.56 (1H, s), 5.38 (1H, d), 3.72 (3H, s), 3.41 (1H, dd), 3.31 (3H, s), 2.80 (1H, m), 2.51 (2H, m), 2.33 (1H, m), 2.02 (1H, dd), 1.88 (1H, m), 1.33 (9H, s), 1.15 (3H, d), 1.02 (3H, d). 1 proton obscured by solvent

EXAMPLE 3 rel-(2S,4R,5R)-2-isobutyl-1-(3-methoxy-4-tert-butylbenzoyl)-4-fluoromethyl-5-(1,3-thiazol-2-yl)pyrrolidine-2-carboxylic acid

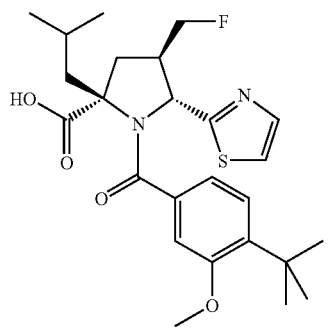

Racemic;
Relative stereochemistry shown

The title compound was prepared in a similar manner to Example 1 from Intermediate 7.

MS calcd for $(C_{25}H_{33}FN_2O_4S+H)^+$: 477
MS found (electrospray): $(M+H)^+=477$
¹H NMR (CD₃OD): δ 7.43 (1H, d), 7.26 (1H, br s), 7.18 (1H, d), 6.91 (1H, d), 6.59 (1H, s), 5.44 (1H, s), 4.33-4.58 (2H, m), 3.73 (3H, s), 2.93 (1H, m), 2.52 (2H, m), 2.39 (1H, dd), 2.03 (1H, m), 1.89 (1H, m), 1.33 (9H, s), 1.16 (3H, d), 1.02 (3H, d)

EXAMPLE 4 rel-(2S,4R,5R)-2-isobutyl-1-(3-methoxy-4-tert-butylbenzoyl)-4-methyl-5-(1,3-thiazol-2-yl)pyrrolidine-2-carboxylic acid

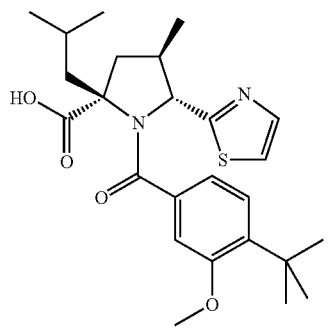

Racemic;
Relative stereochemistry shown

The title compound was prepared in a similar manner to Example 1 from Intermediate 9.

MS calcd for $(C_{25}H_{34}N_2O_4S+H)^+$: 459
MS found (electrospray): $(M+H)^+=459$
¹H NMR (CD₃OD): δ 7.40 (1H, d), 7.25 (1H, brs), 7.15 (1H, d), 6.89 (1H, d), 6.59 (1H, s), 5.03 (1H, d), 3.73 (3H, s), 2.62 (1H, m), 2.53 (1H, m), 2.43 (1H, dd), 2.18 (1H, t), 2.04 (1H, m), 1.90 (1H, m), 1.33 (9H, s), 1.15 (3H, d), 1.04 (3H, d), 1.02 (3H, d)

EXAMPLE 5

2-Allyl-1-(3-bromo 4-tert-butylbenzoyl)-pyrrolidine-2-carboxylic acid

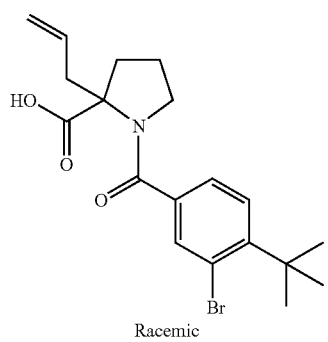

Racemic

2-Allyl-pyrrolidine-2-carboxylic acid hydrochloride (*J. Chem. Soc. Chem. Commun.*, 1988, 22, 1447) (64 mg) was dissolved in dichloromethane (5 mL) and treated with 3-bromo-4-tert-butylbenzoyl chloride[1] (101 mg) and triethylamine (139 uL). The mixture was stirred at room temperature for 18 h. Hydrochloric acid (2N, 5 mL) was added and the mixture stirred for 5 min. The organic was separated using a PTFE filter and concentrated to give a yellow gum. This was purified by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy, to give the title compound as a solid (68 mg)

MS calcd for $(C_{19}H_{24}BrNO_3+H)^+$: 394/396
MS found (electrospray): $(M+H)^+=394/396$
¹H NMR (CDCl₃): δ 7.75 (1H, d), 7.50 (1H, d), 7.42 (1H, dd), 5.79 (1H, m), 5.22-5.28 (2H, m), 3.53 (2H, m), 3.15 (1H, dd), 2.86 (1H, dd), 2.70 (1H, m), 2.07 (1H, m), 1.87 (2H, m), 1.52 (9H, s)

Ref. (1): Synthesised from 3-bromo-4-tert-butylbenzoic acid (*Aust J. Chem.*, 1990, 43, 807).

EXAMPLE 6

2-Benzyl-1 (3-bromo-4-tert-butylbenzoyl)-pyrrolidine-2-carboxylic acid

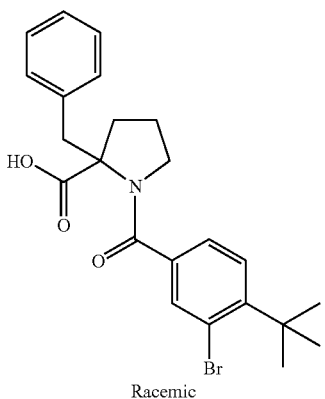

Racemic

The title compound was prepared in a similar manner to Example 5 from 2-benzyl-pyrrolidine-2-carboxylic acid.

MS calcd for $(C_{23}H_{26}BrNO_3+H)^+$: 444/446
MS found (electrospray): $(M+H)^+$=444/446
$^1H$ NMR (CD$_3$OD): δ 7.64 (1H, d), 7.61 (1H, d), 7.36 (4H, m), 7.26 (2H, m), 3.92 (1H, d), 3.39 (1H, m), 3.13 (1H, d), 2.82 (1H, m) 2.33 (1H, m), 2.19 (1H, m), 1.85 (1H, m), 1.55 (9H, s), 1.35 (1H, m)

EXAMPLE 7 rel-(2S,4R,5R)-2-isobutyl-1-(3-methoxy-4-tert-butylbenzoyl)-4-hydroxymethyl-5-(1,3-thiazol-2-yl) pyrrolidine-2-carboxylic acid

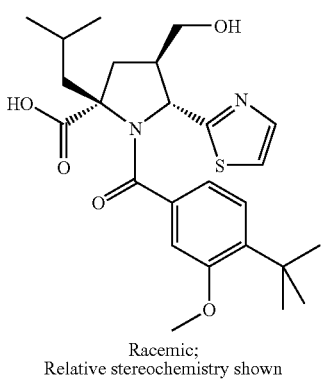

Racemic;
Relative stereochemistry shown

To a solution of Intermediate 4 (52 mg, 0.098 mmol), was added trifluoroacetic acid (2 mL). The solution was left overnight at room temperature. The solvent was evaporated in vacuo and the residue was co-evaporated with CH$_2$Cl$_2$ (×2) and toluene, then triturated with diethyl ether. The resulting white solid was treated with 1 mL of a solution of NaOH in methanol (6.4 mg NaOH in 1 mL MeOH) and was stirred at room temperature overnight. The solvent was then evaporated in vacuo and the residue was purified by reverse phase HPLC on a C$_{18}$ column using a two-solvent gradient elution with (A) water containing formic acid (0.1%) and (B) acetonitrile-water (95:5 v/v) containing formic acid (0.05%) as the eluents to give the title compound as a solid.

MS calcd for $(C_{25}H_{34}N_2O_5S+H)^+$: 475
MS found (electrospray): $(M+H)^+$=475
$^1H$ NMR (CD$_3$OD): δ 7.37 (1H, d), 7.25 (1H, br s), 7.13 (1H, d), 6.86 (1H, d, 6.56 (1H, s), 5.34 (1H, d), 3.71 (3H, s), 3.55 (1H, dd), 3.46 (1H, dd), 2.68 (1H, m), 2.49 (2H, m), 2.33 (1H, dd), 2.02 (1H, m), 1.88 (1H, m), 1.30 (9H, s), 1.14 (3H, d), 1.00 (3H, d)

EXAMPLE 8 rel-(4(2S,4S,5R)-2-isobutyl-1-(3-methoxy-4-tert-butylbenzoyl)-4-hydroxymethyl-5-(1,3-thiazol-2-yl) pyrrolidine-2-carboxylic acid The title compound was prepared in a similar manner to Example 7 from Intermediate 4a.

MS calcd for $(C_{25}H_{34}N_2O_5S+H)^+$: 475
MS found (electrospray): $(M+H)^+$=475
$^1H$ NMR (CD$_3$OD): δ 7.82 (1H, d), 7.56 (1H, d), 7.19 (1H, d), 6.68 (1H, dd), 6.35 (1H, d), 5.69 (1H, d), 3.63 (3H, s), 3.18 (2H, m), 3.01 (1H, m), 2.00-2.35 (5H, m), 1.30 (9H, s), 1.14 (3H, d), 1.11 (3H, d).

EXAMPLE 9 rel-(12S,4R,5R)-2-isobutyl-1-(3-methoxy-4-tert-butylbenzoyl)-4-allyloxymethyl-5-(1,3-thiazol-2-yl)pyrrolidine-2-carboxylic acid

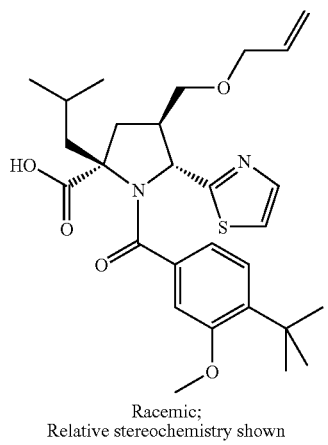

Racemic;
Relative stereochemistry shown

The title compound was prepared in a similar manner to Example 1 from Intermediate 14.

MS calcd for $(C_{28}H_{38}N_2O_5S+H^+)$: 515
MS found (electrospray): $(M+H)^+=515$
$^1$H NMR (CD$_3$OD): δ 7.38 (1H, d), 7.24 (1H, br s), 7.14 (1H, d), 6.85 (1H, d), 6.54 (1H, s), 5.85 (1H, m), 5.40 (1H, d), 5.19 (1H, dd), 5.11 (1H, dd), 3.92 (2H, m), 3.70 (3H, s), 3.46 (1H, m), 3.38 (1H, m), 2.80 (1H, m), 2.52 (2H, m), 2.32 (1H, dd), 1.99 (1H, dd), 1.87 (1H, m), 1.30 (9H, s), 1.14 (3H, d), 1.00 (3H, d).

EXAMPLE 10 rel-(2S,4R,5R)-2-isobutyl-1-(3-methoxy-4-tert-butylbenzoyl)-4-propyloxymethyl-5-(1,3-thiazol-2-yl)pyrrolidine-2-carboxylic acid

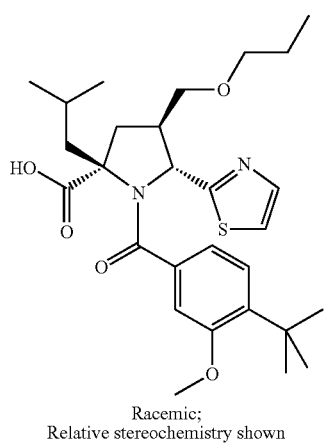

Racemic;
Relative stereochemistry shown

The title compound was prepared in a similar manner to Example 1 from Intermediate 15.

MS calcd for $(C_{28}H_{40}N_2O_5S+H+)$: 517
MS found (electrospray): $(M+H)^+=517$
$^1$H NMR (CD$_3$OD): δ 7.36 (1H, d), 7.21 (1H, br s), 7.13 (1H, d), 6.84 (1H, d), 6.54 (1H, s), 5.38 (1H, d), 3.70 (3H, s), 3.42 (1H, dd), 3.34 (4H, m—partially hidden by solvent), 2.79 (1H, m), 2.52 (1H, t), 2.29 (1H, dd), 1.97 (1H, dd), 1.86 (1H, m), 1.53 (2H, m), 1.30 (9H, s), 1.14 (3H, d), 1.00 (3H, d), 0.90 (3H, t).

EXAMPLE 11 rel-(2S,4S,5R)-2-isobutyl-1-(3-methoxy-4-tert-butylbenzoyl)-4-methoxymethyl-5-(1,3-thiazol-2-yl)pyrrolidine-2-carboxylic acid

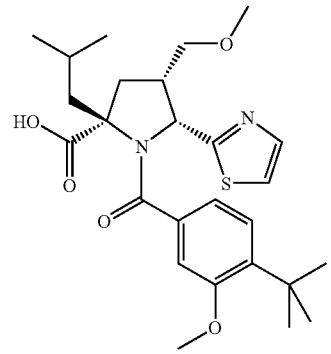

Racemic;
Relative stereochemistry shown

To a solution of Intermediate 16 (51 mg, 0.1 mmol) in dichloromethane (5 mL) was added trifluoroacetic acid (2 mL) and the solution stirred at ambient temperature overnight. The reaction mixture was evaporated and the residue triturated with diethyl ether to give the title compound as a solid.

MS calcd for $(C_{26}H_{36}N_2O_5S+H)^+$: 489.
MS found (electrospray): $(M+H)^+=489$ Nmr spectroscopy showed this compound to be identical to example 15—racemate vs single enantiomer.

EXAMPLE 12 rel-(2S,4S,5R)-2-isobutyl-1-(3-methoxy-4-tert-butylbenzoyl)-4-ethoxymethyl-5-(1,3-thiazol-2-yl)pyrrolidine-2-carboxylic acid

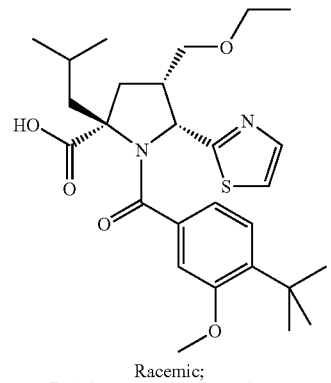

Racemic;
Relative stereochemistry shown

The title compound was prepared in a similar manner to Example 11 from Intermediate 17

MS calcd for $(C_{27}H_{38}N_2O_5S+H)^+$: 503
MS found (electrospray): $(M+H)^+=503$.
Nmr spectroscopy showed this compound to be identical to example 16—racemate vs single enantiomer

EXAMPLE 13 rel-(2S,4S,5R)-2-isobutyl-1-(3-methoxy-4-tert-butyl-benzoyl)-4-isopropenyl-5-(1,3-thiazol-2-yl)pyrrolidine-2-carboxylic acid

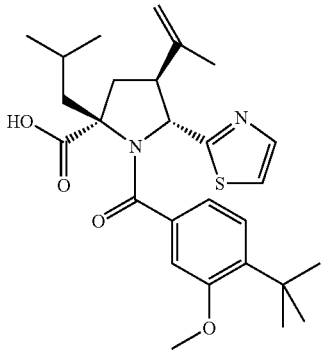

Racemic;
Relative stereochemistry shown

Intermediate 12 (74 mg, 0.14 mmol) was dissolved in trifluoroacetic acid (2 mL). The reaction was left at room temperature overnight. The solvent was then evaporated in vacuo and the residue was triturated with diethyl ether. The resulting solid was collected by filtration and dried in vacuo to give the title compound.

MS calcd for $(C_{27}H_{36}N_2O_4S+H)^+$: 485.
MS found (electrospray): $(M+H)^+=485$.
$^1$H NMR (CD$_3$OD): δ 7.36 (1H, d), 7.15 (2H, m), 6.88 (1H, d), 6.51 (1H, s), 5.32 (1H, d), 4.78 (1H, br s), 4.68 (1H, s), 3.69 (3H, s), 3.32 (1H, m), 2.49 (2H, m), 2.33 (1H, dd), 2.02 (1H, dd), 1.88 (1H, m), 1.71 (3H, s), 1.30 (9H, s), 1.16 (3H, d), 1.01 (3H, d).

EXAMPLE 14 rel-(2S,4S,5R)-2-isobutyl-1-(3-methoxy-4-tert-butyl-benzoyl)-4-isopropyl-5-(1,3-thiazol-2-yl)pyrrolidine-2-carboxylic acid

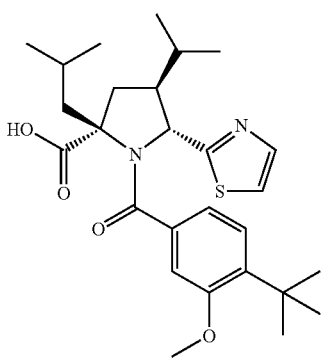

Racemic;
Relative stereochemistry shown

The title compound was prepared in a similar manner to Example 1 from Intermediate 13.

MS calcd for $(C_{27}H_{38}N_2O_4S+H)^+$: 487.
MS found (electrospray): $(M+H)^+=487$.
$^1$H NMR (CD$_3$OD): δ 7.38 (1H, d), 7.16 (2H, m), 6.85 (1H, d), 6.46 (1H, s), 5.22 (1H, d), 3.69 (3H, s), 2.51 (2H, m), 2.26 (2H, m), 1.97 (1H, dd), 1.84 (1H, m), 1.66 (1H, m), 1.31 (9H, s), 1.14 (3H, d), 1.00 (3H, d), 0.93 (3H, d), 0.75 (3H, d).

EXAMPLE 15

(2S,4S,5R)-2-isobutyl-1-(3-methoxy-4-tert-butylbenzoyl)-4-methoxymethyl-5-(1,3-thiazol-2-yl)pyrrolidine-2-carboxylic acid Enantiomer A of rel-(2S,4S,5R)-2-isobutyl-1-(3-methoxy-4-tert-butylbenzoyl)-4-methoxymethyl-5-(1,3-thiazol-2-yl)pyrrolidine-2-carboxylic acid

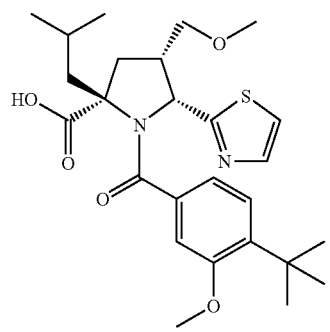

Chiral, Enantiomer A
Absolute stereochemistry shown
Stereochemistry determined by reference to Intermediate 21

To a solution of Intermediate 21 (191 mg) in dichloromethane (5 mL) was added trifluoroacetic acid (5 mL) and the resulting solution was allowed to stand at 20° C. for 18 h. The mixture was evaporated to dryness and the residue was triturated with ether to give Enantiomer A of the title compound as a solid.

MS calcd for $(C_{26}H_{36}N_2O_5S+H)^+$: 489.
MS found (electrospray): $(M+H)^+=489$
$^1$H NMR (CD$_3$OD): δ 7.87 (1H, d), 7.61 (1H, d), 7.23 (1H, d), 6.72 (1H, dd), 6.37 (1H, s), 5.67 (1H, d), 3.65 (3H, s), 3.21 (2H, m), 3.11 (3H, s), 2.69 (1H, t), 2.17-2.33 (4H, m), 2.05 (1H, m), 1.33 (9H, s), 1.15 (3H, d), 1.13 (3H, d), Carboxylic acid proton exchanged with solvent. This compound was identical by NMR to Example 11 (above).

The absolute stereochemistry of this compound was determined by reference to Intermediate 21 and shown to be (2S,4S,5R), as drawn.

EXAMPLE 16

(2S,4S,5R)-2-isobutyl-1-(3-methoxy-4-tert-butylbenzoyl)-4-ethoxymethyl-5-(1,3-thiazol-2-yl)pyrrolidine-2-carboxylic acid Enantiomer A of rel-(2S,4S,5R)-2-isobutyl-1-(3-methoxy-4-tert-butylbenzoyl)-4-ethoxymethyl-5-(1,3-thiazol-2-yl)pyrrolidine-2-carboxylic acid

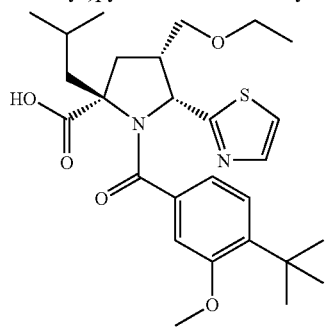

Chiral, Enantiomer A
Absolute stereochemistry shown
Stereochemistry determined by X-ray crystallography To a solution of Intermediate 22 (219 mg) in dichloromethane (5 mL) was added trifluoroacetic acid (5 mL) and the resulting solution was stored at 20° C. for 18 h. The mixture was evaporated to dryness and the residue was triturated with ether to give Enantiomer A of the title compound as a solid.

MS calcd for $(C_{27}H_{38}N_2O_5S+H)^+$: 503

MS found (electrospray): $(M+H)^+=503$.

$^1$H NMR (CD$_3$OD): δ 7.87 (1H, d), 7.61 (1H, d), 7.23 (1H, d), 6.73 (1H, dd), 6.36 (1H, d), 5.69 (1H, d), 3.65 (3H, s), 3.15-3.30 (4H, m), 2.72 (1H, t), 2.20-2.35 (4H, m), 2.05 (1H, m), 1.33 (9H, s), 1.15 (3H, d), 1.13 (3H, d), 1.09 (3H, t), Carboxylic acid proton exchanged with solvent. This compound was identical by NMR to Example 12 (above).

The absolute stereochemistry of this compound was determined by X-ray crystallography and shown to be (2S,4S, 5R), as drawn.

EXAMPLE 17

(2S,4S,5R)-2-isobutyl-1-(3-bromo-4-tert-butylbenzoyl)-4-ethoxymethyl-5-(1,3-thiazol-2-yl)-pyrrolidine-2-carboxylic acid

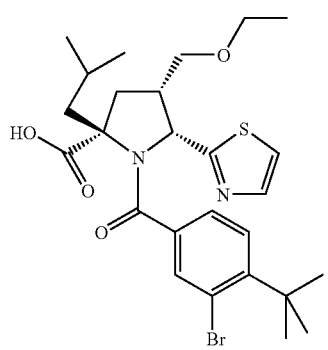

Chiral;
Absolute stereochemistry as drawn

The title compound was prepared in a similar manner to Example 1, using Intermediate 29 as starting material.

MS calcd for $(C_{26}H_{35}BrN_2O_4S+H)^+$: 551 and 553

MS found (electrospray): $(M+H)^+=551$ and 553

$^1$H NMR (CD$_3$OD): δ 7.83 (d, 1H), 7.60 (d, 1H), 7.42 (d, 1H), 7.09-7.04 (m, 2H), 5.61 (d, 1H), 3.28-3.20 (m, 3H), 3.15 (m, 1H), 2:72 (t, 1H), 2.32-2.15 (m, 4H), 2.02 (m, 1H), 1.45 (s, 9H), 1.10 (t, 6H), 1.06 (t, 3H).

EXAMPLE 18

(2S,4S,5R)-2-isobutyl-1-(3-chloro-4-tert-butylbenzoyl)-4-ethoxymethyl-5-(1,3-thiazol-2-yl)-pyrrolidine-2-carboxylic acid

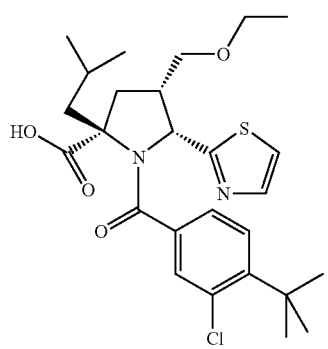

Chiral;
Absolute stereochemistry as drawn

The title compound was prepared in a similar manner to Example 1, using Intermediate 30 as starting material.

MS calcd for $(C_{26}H_{35}ClN_2O_4S+H)^+$: 507 and 509

MS found (electrospray): $(M+H)^+=507$ and 509

$^1$H NMR (CD$_3$OD): δ 7.82 (d, 1H), 7.59 (d, 1H), 7.40 (d, 1H), 7.00 (dd, 1H), 6.86 (1H), 5.63 (d, 1H), 3.29-3.20 (m, 3H), 3.20-3.11 (m, 1H), 2.71 (t, 1H), 2.31-2.15 (m, 4H), 2.03-1.97 (m, 1H), 1.42 (s, 9H), 1.10 (t, 6H), 1.06 (t, 3H).

EXAMPLE 19

(2S,4S,5R)-2-isobutyl-1-(3-methyl-4-tert-butylbenzoyl)-4-ethoxymethyl-5-(1,3-thiazol-2-yl)pyrrolidine-2-carboxylic acid

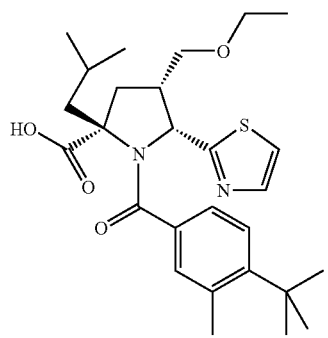

Chiral;
Absolute stereochemistry as drawn

Sodium hydride (60% dispersion in mineral oil; 0.061 g, 1.52 mmol) was added to a stirred solution of Intermediate 28 (0.48 g, 0.93 mmol) in anhydrous DMF (10 mL) at 0° C. The resulting mixture was stirred at 0° C. for 30 minutes prior to the addition of iodoethane (0.37 mL, 4.65 mmol). The mixture was stirred at 5° C. for 2 h, then evaporated to dryness. The residue was dissolved in trifluoroacetic acid (8 mL) and stirred at room temperature for 19 h. The trifluoroacetic acid was evaporated and the residue dissolved in ethyl acetate, washed with water, dried ($Na_2SO_4$) and evaporated. The crude product was purified by chromatography on silica gel using cyclohexane-ethyl acetate (gradient elution from 2:1 v/v to 3:2 v/v) as eluent and then crystallised from diethyl ether to afford the title compound, a solid.

MS calcd for $(C_{27}H_{38}N_2O_4S+H)^+$: 487

MS found (electrospray): (M+H)+487

$^1$H NMR ($CD_3OD$): δ 7.81 (d, 1H), 7.56 (d, 1H), 7.27 (d, 1H), 6.85 (dd, 1H), 6.62 (bs, 1H), 5.625 (d, 1H), 3.28-3.19 (m, 3H), 3.20-3.09 (m, 1H), 2.69 (t, 1H), 2.37 (s, 3H), 2.32-2.14 (m, 4H), 2.02 (m, 1H), 1.35 (s, 9H), 1.12 (d, 3H), 1.09 (d, 3H), 1.05 (t, 3H).

EXAMPLE 20 rel-(2R,4R,5R)-2-Benzyl-1-(3-methoxy-4-tert-butyl-benzoyl)-4-methoxymethyl-5-(1,3-thiazol-2-yl)-pyrrolidine-2-carboxylic acid

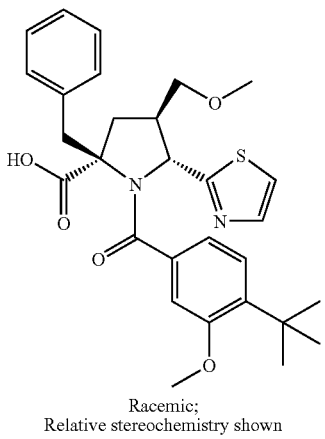

Racemic;
Relative stereochemistry shown

The title compound was prepared in a similar manner to Example 1, using Intermediate 37 as starting material.

MS calcd for $(C_4H_{34}N_2O_5S+H)^+$: 523

MS found (electrospray): (M+H)$^+$=523

$^1$H NMR ($CD_3OD$): δ 7.60 (m, 6H), 7.30 (d, 1H), 7.16 (d, 1H), 6.62 (d, 1H), 6.55 (s, 1H), 4.82 (d, 1H), 4.15 (d, 1H), 3.81 (s, 3H), 3.39 (d, 1H), 3.30 (s, 3H), 3.27 (dd, 1H), 3.21 (dd, 1H), 2.89 (m, 1H), 2.72 (t, 1H), 2.50 (dd, 1H), 1.43 (s, 9H).

EXAMPLE 21 rel-(2R,4R,5R)-2-Benzyl-1-(3-methoxy-4-tert-butyl-benzoyl)-4-ethoxymethyl-5-(1,3-thiazol-2-yl)-pyrrolidine-2-carboxylic acid

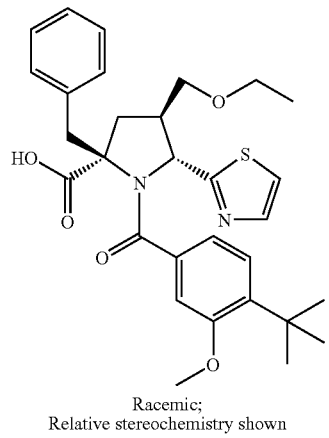

Racemic;
Relative stereochemistry shown

The title compound was prepared in a similar manner to Example 1, using Intermediate 38 as starting material.

MS calcd for $(C_{30}H_{36}N_2O_5S+H)^+$: 537

MS found (electrospray): (M+H)$^+$=537

$^1$H NMR ($CD_3OD$): δ 7.36 (6H, m), 7.19 (1H, d), 7.03 (1H, d), 6.48 (1H, d), 6.42 (1H, s), 4.73 (1H, d), 4.02 (1H, d), 3.68 (3H, s), 3.34 (1H, m), 3.25 (2H, dd), 3.19 (2H, m), 2.76 (1H, m), 2.64 (1H, t), 2.37 (1H, dd), 1.29 (9H, s), 1.03 (3H, t)

EXAMPLE 22

Enantiomer A of rel-(2S,4S,5R)-2-isobutyl-1-(3-methoxy-4-tert-butylbenzoyl)-4-methoxymethyl-5-(pyrazin-2-yl)pyrrolidine-2-carboxylic acid

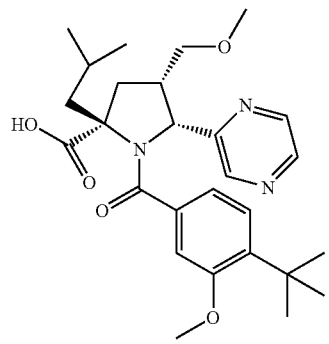

Chiral; Enantiomer A
Relative stereochemistry shown

The title compound was prepared in a similar manner to Example 1, using Intermediate 43 as starting material.

MS calcd for $(C_{27}H_{37}N_3O_5+H)^+$: 484

MS found (electrospray): (M+H)$^+$=484

$^1$H NMR ($CD_3OD$): δ 8.52 (m, 2H), 8.30 (s, 1H), 7.14 (d, 1H), 6.66 (d, 1H), 6.35 (s, 1H), 5.52 (d, 1H), 3.60 (s, 3H), 3.34 (1H, m), 3.13 (m, 1H), 2.92 (s, 3H), 2.70 (m, 1H), 2.27 (m, 4H), 2.05 (m, 1H), 1.27 (s, 9H), 1.14 (d, 3H), 1.11 (d, 3H).

EXAMPLE 23 rel-(2S,4R,5R)-2-isobutyl-1-(3-methoxy-4-tert-butylbenzoyl)-4-methoxymethyl-5-(pyrazin-2-yl)pyrrolidine-2-carboxylic acid

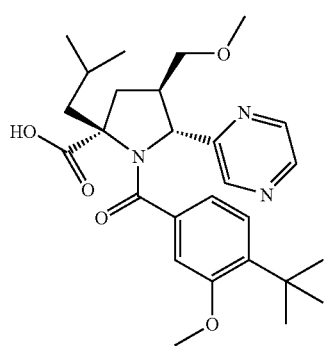

Racemic;
Relative stereochemistry shown

The title compound was prepared in a similar manner to Example 1, using Intermediate 46 as starting material.

MS calcd for $(C_{27}H_{37}N_3O_6+H)^+$: 484
MS found (electrospray): $(M+H)^+=484$
$^1$H NMR (CD$_3$OD): δ 8.62 (s, 1H), 8.11 (s, 1H), 8.08 (s, 1H), 7.00 (d, 1H), 6.73 (d, 1H), 6.40 (s, 1H), 5.00 (d, 1H), 3.60 (s, 3H), 3.29 (m, 1H), 3.23 (m, 1H), 3.14 (s, 3H), 2.62 (m, 1H), 2.43 (m, 1H), 2.31 (m, 2H), 1.99 (m, 1H), 1.80 (m, 1H), 1.18 (s, 9H), 1.05 (d, 3H), 0.93 (d, 3H).

EXAMPLE 24 rel-(2S,4S,5R)-2-isobutyl-1-(3-methoxy-4-tert-butylbenzoyl)-4-methoxymethyl-5-(5-methyl-1,3-thiazol-2-yl)pyrrolidine-2-carboxylic acid

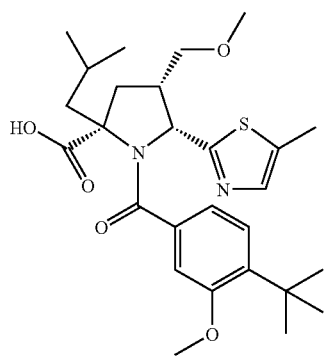

Racemic;
Relative stereochemistry shown

The title compound was prepared in a similar manner to Example 1, using Intermediate 51 as starting material.

MS calcd for $(C_{27}H_{38}N_2O_5S+H)^+$: 503
MS found (electrospray): $(M+H)^+=503$
$^1$H NMR (CD$_3$OD): δ 7.52 (1H, s), 7.22 (1H, d), 6.72 (1H, d), 6.29 (1H, s), 5.5 (1H, d), 3.64 (3H, s), 3.26-3.15 (2H, m), 3.11 (3H, s), 2.77-2.67 (1H, m), 2.37 (3H, s), 2.3-1.94 (5H, m), 1.31 (9H, s), 1.11 (3H, d) and 1.08 (3H, d)

EXAMPLE 25

Enantiomer A of rel-(2S,4S,5R)-2-isobutyl-1-(3-methoxy-4-tert-butylbenzoyl)-4-methoxymethyl-5-(5-methyl-1,3-thiazol-2-yl)pyrrolidine-2-carboxylic acid

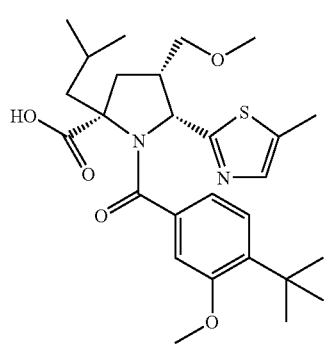

Chiral; Enantiomer A
Relative stereochemistry shown

The title compound was prepared in a similar manner to Example 1, using Intermediate 93 as starting material.

MS calcd for $(C_{27}H_{38}N_2O_5S+H)^+$: 503
MS found (electrospray): $(M+H)^+=503$
$^1$H NMR (CD$_3$OD): δ 7.52 (1H, s), 7.22 (1H, d), 6.72 (1H, d), 6.29 (1H, s), 5.5 (1H, d), 3.64 (3H, s), 3.26-3.15 (2H, m), 3.11 (3H, s), 2.77-2.67 (1H, m), 2.37 (3H, s), 2.3-1.94 (5H, m), 1.31 (9H, s), 1.11 (3H, d) and 1.08 (3H, d).

EXAMPLE 26 rel-(2S,4S,5R)-2-isobutyl-1-(3-methoxy-4-tert-butylbenzoyl)-4-methoxymethyl-5 (2-chloro-1,3-thiazol-5-yl)pyrrolidine-2-carboxylic acid

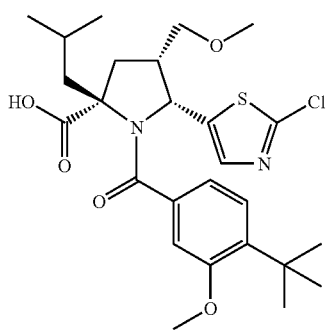

Racemic;
Relative stereochemistry shown

The title compound was prepared in a similar manner to Example 1, using Intermediate 56 as starting material.

MS calcd for $(C_{26}H_{35}ClN_2O_5S+H)^+$: 523/525
MS found (electrospray): $(M+H)^+=523/525$
$^1$H NMR (CD$_3$OD): δ 7.42 (1H, s), 7.21 (1H, d), 6.74 (1H, d), 6.46 (1H, s), 5.42 (1H, s), 3.66 (3H,s), 3.19 (1H, m), 3.12 (1H, m), 3.08 (3H, s), 2.88 (1H, t), 2.32-2.07 (4H, m), 2.00 (1H, m), 1.33 (9H, s), 1.09 (6H, dd).

EXAMPLE 27 rel-(2S,4S,5R)-2-isobutyl-1-(3-methoxy-4-tert-butyl-benzoyl)-4-methoxymethyl-5-(2-methoxy-1,3-thiazol-5-yl)pyrrolidine-2-carboxylic acid

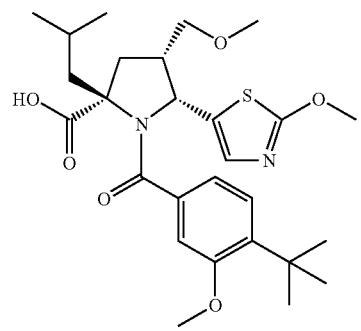

Racemic;
Relative stereochemistry shown

The title compound was prepared in a similar manner to Example 1, using Intermediate 57 as starting material.

MS calcd for $(C_{27}H_{38}N_2O_6S+H)^+$: 519

MS found (electrospray): $(M+H)^+$=519

$^1$H NMR (CD$_3$OD): δ 7.2 (1H, d), 6.89 (1H, s), 6.75 (1H, d), 6.54 (1H, s), 5.23 (1H, d), 3.94 (3H, s), 3.67 (3H, s), 3.16 (1H, m), 3.12 (3H, s), 3.04 (1H, m), 2.96 (1H, m), 2.29-2.05 (4H, m), 1.98 (1H, m), 1.33 (9H, s), 1.08 (6H, m).

EXAMPLE 28 rel-(2S,4R,5R)-2-isobutyl-1-(3-methoxy-4-tert-butylbenzoyl)-4-((methylthio)methyl)-5-(1,3-thiazol-2-yl)pyrrolidine-2-carboxylic acid

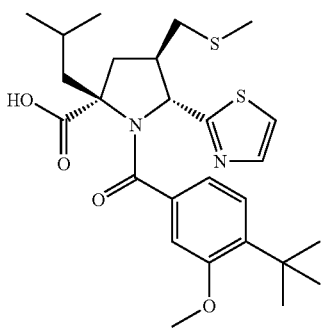

Racemic;
Relative stereochemistry shown

The title compound was prepared in a similar manner to Example 1, using Intermediate 58 as the starting material.

MS calcd for $(C_{26}H_{36}N_2O_4S_2+H)^+$: 505

MS found (electrospray): $(M+H)^+$=505

$^1$H NMR (CDCl$_3$): δ 7.48 (1H, d), 7.19 (1H, d), 7.11 (1H, d), 6.88 (1H, d), 6.45 (1H, s), 5.22 (1H, d), 3.67 (3H, s), 3.07 (1H, dd), 2.76-2.63 (2H, m), 2.63-2.49 (2H, m), 2.11-1.96 (2H, m), 2.04 (3H, s), 1.93-1.81 (1H, m), 1.31 (9H, s), 1.08 (3H, d), 1.04 (3H, d).

EXAMPLE 29 rel-(2S,4R,5R)-2-isobutyl-1-(3-methoxy-4-tert-butylbenzoyl)-4-((methanesulfonyl)methyl)-5-(1,3-thiazol-2-yl)pyrrolidine-2-carboxylic acid

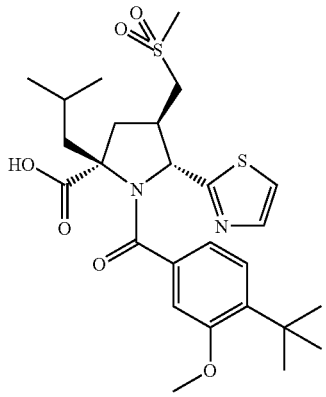

Racemic;
Relative stereochemistry shown

The title compound was prepared in a similar manner to Example 1, using Intermediate 59 as starting material.

MS calcd for $(C_{26}H_{36}N_2O_6S_2+H)^+$: 537

MS found (electrospray): $(M+H)^+$=537

$^1$H NMR (CDCl$_3$): δ 7.40 (1H, d), 7.25 (1H, d), 7.18 (1H, d), 6.85 (1H, d), 6.49 (1H, s), 5.52 (1H, d), 3.69 (3H, s), 3.31 (1H, dd), 3.22-3.09 (2H, m), 2.98-2.89 (1H, m), 2.89 (3H, s), 2.51 (1H, dd), 2.26 (1H, t), 2.04 (1H, dd), 1.94-1.81 (1H, m), 1.31 (9H, s), 1.08 (3H, d), 1.04 (3H, d).

EXAMPLE 30 rel-(2S,4R,5R)-2-isobutyl-1-(3-methoxy-4-tert-butylbenzoyl)-4-(1,1-difluoroethyl)-5-(1,3-thiazol-2-yl)pyrrolidine-2-carboxylic acid

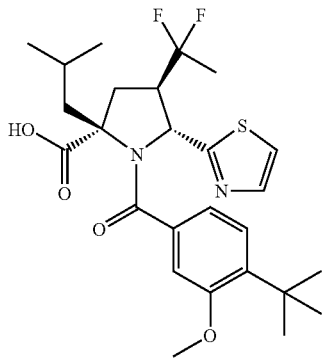

Racemic;
Relative stereochemistry shown

The title compound was prepared in a similar manner to Example 1, using Intermediate 60 as starting material.

MS calcd for $(C_{26}H_{34}N_2F_2O_4S+H)^+$: 509

MS found (electrospray): $(M+H)^+$=509

$^1$H NMR (CDCl$_3$): δ 7.59 (1H, d), 7.23 (1H, d), 7.09 (1H, d), 6.93 (1H, dd) 6.42 (1H, s), 5.57 (1H, d), 3.67 (3H, s), 3.07 (1H, m), 2.96 (1H, dd), 2.51 (1H, dd), 2.25 (1H, dd), 2.13 (1H, dd), 1.85 (1H, m), 1.59 (3H, t), 1.33 (9H, s), 1.08 (3H, d), 10.3 (3H, d).

EXAMPLE 31 rel-(2S,4R,5R)-2-isobutyl-1-(3-methoxy-4-tert-butylbenzoyl)-4-(1-hydroxy-1-methylethyl)-5-(1,3-thiazol-2-yl)pyrrolidine-2-carboxylic acid

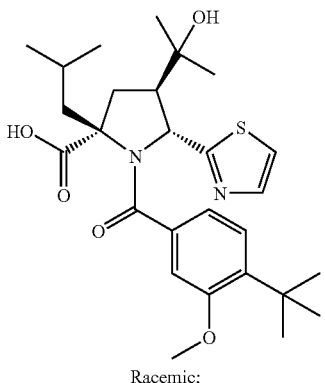

Racemic;
Relative stereochemistry shown

The title compound was prepared in a similar manner to Example 1, using Intermediate 61 as starting material.

MS calcd for $(C_{27}H_{38}N_2O_5S+H)^+$: 503
MS found (electrospray): $(M+H)^+=503$
$^1$H NMR (CDCl$_3$): δ 7.44 (1H, d), 7.22 (1H, d), 7.11 (1H, d), 6.94 (1H, d), 6.43 (1H, s), 5.56 (1H, d), 3.67 (3H, s), 2.87 (1H, dd), 2.65 (1H, m), 2.49 (1H, dd), 2.20 (1H, m), 2.08 (1H dd), 1.87 (1H, m), 1.33 (9H, s), 1.30 (3H, s), 1.08 (6H, m), 1.02 (3H, d).

EXAMPLE 32

Enantiomer A of rel-(2S,4R,5R)-2-Isobutyl-1-(3-methoxy-4-tert-butylbenzoyl)-4-methoxymethyl-5-(1,3-thiazol-2-yl)pyrrolidine-2-carboxylic acid

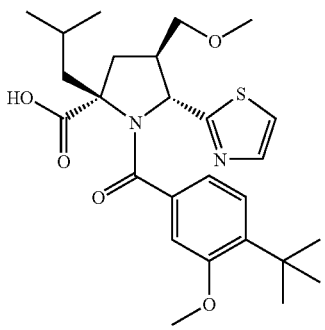

Chiral, Enantiomer A;
Relative stereochemistry shown

The title compound was prepared in a similar manner to Example 1, using Intermediate 62 as starting material.

MS calcd for $(C_{26}H_{36}N_2O_5S+H)^+$: 489
MS found (electrospray): $(M+H)^+=489$
$^1$H NMR (CD$_3$OD): δ7.41 (1H, d), 7.26 (1H, s), 7.16 (1H, d), 6.88 (1H, d), 6.55 (1H, s), 5.38 (1H, d), 3.71 (3H, s), 3.41 (1H, m), 3.28-3.35 (4H, m), 2.80 (1H, m), 2.51 (2H, m), 2.33 (1H, dd), 2.02 (1H, dd), 1.87 (1H, m), 1.32 (9H, s), 1.15 (3H, d), 1.01 (3H, d).

EXAMPLE 33 rel-(2R,4S,5R)-2-Benzyl-1-(3-methoxy-4-tert-butylbenzoyl)-4-methoxymethyl-5-1,3-thiazol-2-yl)-pyrrolidine-2-carboxylic acid

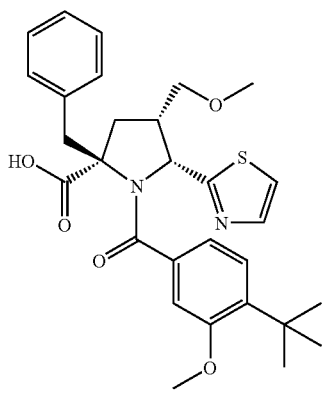

Racemic;
Relative stereochemistry shown

The title compound was prepared in a similar manner to Example 1, using Intermediate 63 as the starting material.

MS calcd for $(C_{29}H_{34}N_2O_5S+H)^+$: 523
MS found (electrospray): $(M+H)^+=523$
$^1$H NMR (CD$_3$OD): δ 7.82 (1H, d), 7.53 (1H, d), 7.45 (5H, m), 7.21 (1H, d), 6.71 (1H, d), 6.44 (1H, s), 5.12 (1H, d), 3.87 (1H, d), 3.67 (3H, s), 3.34 (2H, m), 2.91 (3H, s), 2.88 (1H, dd), 2.38 (1H, m), 2.17 (1H, t), 1.85 (1H, m), 1.30 (9H, s)

EXAMPLE 34 rel-(2R,4S,5R)-2-Benzyl-1-(3-methoxy-4-tert-butylbenzoyl)-4-ethoxymethyl-5-(1,3-thiazol-2-yl)-pyrrolidine-2-carboxylic acid

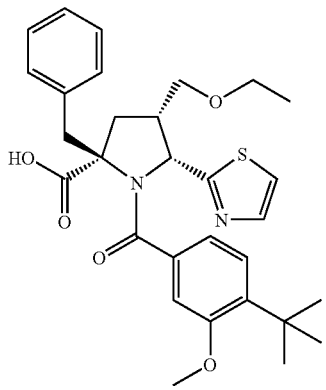

Racemic;
Relative stereochemistry shown

The title compound was prepared in a similar manner to Example 1, using Intermediate 64 as the starting material.
MS calcd for $(C_{30}H_{36}N_2O_5S+H)^+$: 537
MS found (electrospray): $(M+H)^+=537$
$^1$H NMR (CD$_3$OD): δ 7.76 (1H, d), 7.51 (1H, d), 7.43 (5H, m), 7.21 (1H, d), 6.73 (1H, dd), 6.45 (1H, s), 5.13 (1H, d), 3.90 (1H, d), 3.66 (3H, s), 3.35 (1H, d), 3.00 (3H, m), 2.40 (2H, m), 2.20 (1H, t), 1.85 (1H, m), 1.30 (9H, s), 0.93 (3H, t).

EXAMPLE 35 rel-(2S,4S,5R)-2-Isobutyl-1-(3-methoxy-4-tert-butyl-benzoyl)-4-methoxymethyl-5-(pyridin-2-yl)pyrrolidine-2-carboxylic acid

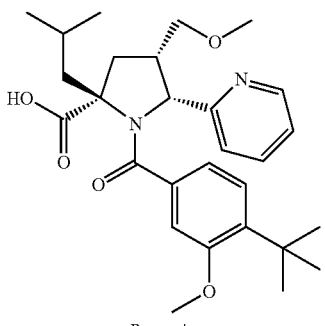

Racemic;
Relative stereochemistry shown

The title compound was prepared in a similar manner to Example 1, using Intermediate 69 as the starting material.
MS calcd for $(C_{28}H_{38}N_2O_5+H)^+$: 483
MS found (electrospray): $(M+H)^+=483$
$^1$H NMR (CDCl$_3$): δ 8.54 (1H, d), 7.51 (1H, t), 7.30 (1H, m), 7.05 (1H, d), 6.73 (1H, d), 6.60 (1H, d), 6.20 (1H, s), 5.31 (1H, d), 3.48 (3H, s), 3.23 (1H, m), 3.16 (1H, m), 3.01 (3H, s), 2.47 (1H, dd), 2.37 (1H, t), 2.29 (1H, dd), 2.18 (2H, m), 1.96 (1H, m), 1.25 (9H, s), 1.16 (3H, d), 1.10 (3H, d).

EXAMPLE 36

(2S,4R,5R)-2-Isobutyl-1-(3-methoxy-4-tert-butyl-benzoyl)-4-(1-hydroxy-1-methylethyl)-5-(1,3-thiazol-2-yl)pyrrolidine-2-carboxylic acid

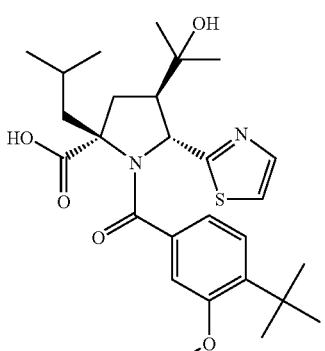

Chiral;
Absolute stereochemistry shown

The title compound was prepared in a similar manner to Example 1, using Intermediate 72 as the starting material.
MS calcd for $(C_{27}H_{38}N_2O_5S+H)^+$: 503
MS found (electrospray): $(M+H)^+=503$
$^1$H NMR (CDCl$_3$): δ 7.45 (1H, d), 7.23 (1H, d), 7.10 (1H, d), 6.95 (1H, d), 6.43 (1H, s), 5.56 (1H, d), 3.67 (3H, s), 2.88 (1H, dd), 2.65 (1H, m), 2.49 (1H, dd), 2.20 (1H, dd), 2.08 (1H, dd), 1.87 (1H, m), 1.34 (9H, s), 1.31 (3H, s), 1.08 (6H, m), 1.03 (3H, d).

EXAMPLE 37a & EXAMPLE 37b

Diastereoisomer 1 and diastereoisomer 2 of (2S,4R,5R)-2-Isobutyl-1-(3-methoxy-4-tert-butylbenzoyl)-4-(1-hydroxyethyl)-5-(1,3-thiazol-2-yl)pyrrolidine-2-carboxylic acid

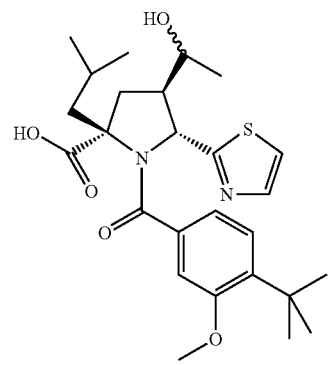

Chiral;
Absolute stereochemistry shown for pyrrolidine ring
Separated diastereoisomers at the alcohol centre
Absolute stereochemistry of alcohol centre in Diastereoisomers 1 & 2 not known.

Sodium borohydride (0.025 g, 0.68 mmol) was added to a cold (0° C.) solution of Intermediate 73 (0.065 g, 0.133 mmol) in anhydrous THF (5 mL) under nitrogen. The mixture was stirred at 0° C. for 30 minutes, then at room temperature for 3 hours. The mixture was acidified (2M HCl) and extracted with ethyl acetate. The organic solution was dried (Na$_2$SO$_4$) and evaporated to afford a gummy solid. This was purified by repeated preparative HPLC on a C18 column using a two-solvent gradient elution with (A) water containing formic acid (0.1%) and (B) acetonitrile-water (95:5 v/v) containing formic acid (0.05%) as eluents to afford a mixture of diastereoisomers of the alcohol. Further HPLC purification on a Chiralpak AD column with heptane-ethanol (90:10 v/v) containing 0.1% trifluoroacetic acid as eluent afforded Diastereoisomer 1 (Example 37a), the earlier eluting diastereoisomer and, subsequently, Diastereoisomer 2 (Example 37b), the later eluting diastereoisomer.

EXAMPLE 37a

MS calcd for $(C_{26}H_{36}N_2O_5S+H)^+$: 489
MS found (electrospray): $(M+H)^+$=489
$^1$H NMR (CD$_3$OD): δ 7.37 (d, 1H), 7.23 (bs, 1H), 7.13 (d, 1H), 6.85 (d, 1H) 6.55 (s, 1H), 5.43 (d, 1H), 3.75-3.68 (m, 1H), 3.71 (s, 3H), 3.67-3.60 (m, 1H), 2.61-2.49 (m, 2H), 2.23 (q, 1H), 2.00 (dd, 1H), 1.93-1.80 (m, 3H), 1.30 (s, 9H), 1.15 (d, 3H), 1.04 (d, 3H), 0.995 (d, 3H).

EXAMPLE 37b

MS calcd for $(C_{26}H_{36}N_2O_5S+H)^+$: 489
MS found (electrospray): $(M+H)^+$=489
$^1$H NMR (CD$_3$OD): δ 7.41 (s, 1H), 7.31 (s, 1H), 7.18 (d, 1H), 6.68 (d, 1H), 6.46 (s, 1H), 5.50 (d, 1H), 3.79 (m, 1H), 3.74-3.66 (m, 1H), 3.70 (s, 3H), 2.74-2.64 (m, 1H), 2.49 (bd, 1H), 2.39 (t, 1H), 2.28 (dd, 1H), 2.00 (m, 1H), 1.91-1.81 (m, 1H), 1.32 (s, 9H), 1.13 (d, 3H), 1.03 (d, 3H), 0.99 (d, 3H).

EXAMPLE 38 rel-(2S,4S,5R)-2-Isobutyl-1-(3-methoxy-4-tert-butyl-benzoyl)-4-ethoxymethyl-5-(1,3-thiazol-4-yl)pyrrolidine-2-carboxylic acid

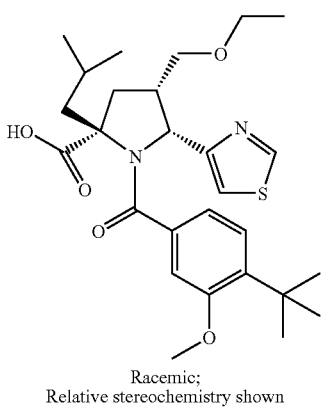

Racemic;
Relative stereochemistry shown

The title compound was prepared in a similar manner to Example 1, using Intermediate 78 as the starting material.
MS calcd for $(C_{27}H_{38}N_2O_5S+H)^+$: 503
MS found (electrospray): $(M+H)^+$=503
$^1$H NMR (CD$_3$OD): δ 9.07 (1H, s), 7.17 (1H, d), 7.08 (1H, s), 6.68 (1H, d), 6.35 (1H, s), 5.59 (1H, d), 3.64 (3H, s), 3.25-3.10 (3H, m), 3.05-3.01 (1H, m), 2.78 (1 H, t), 2.34-1.98 (5H, m), 1.28 (9H, s), 1.14 (3H, d), 1.10 (3H, d) and 1.03 (3H, t).

EXAMPLE 39

Enantiomer A of rel-(2S,4S,5R)-2-Isobutyl-1-(3-methoxy-4-tert-butylbenzoyl)-4-ethoxymethyl-5-(1,3-thiazol-4-yl))-pyrrolidine-2-carboxylic acid

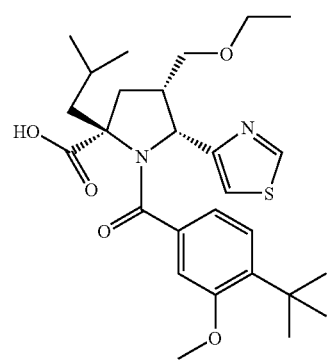

Chiral; Enantiomer A
Relative stereochemistry shown

The title compound was prepared in a similar manner to Example 1, using Intermediate 79 as the starting material.
MS calcd for $(C_{27}H_{39}N_2O_5S+H)^+$: 503
MS found (electrospray): $(M+H)^+$=503
$^1$H NMR (CD$_3$OD): δ 9.08 (1H, s), 7.17 (1H, d), 7.08 (1H, s), 6.68 (1H, d), 6.34 (1H, s), 5.59 (1H, d), 3.64 (3H, s), 3.24-3.10 (3H, m), 3.05-3.01(1H, m), 2.78 (1 H, t), 2.34-1.98 (5H, m), 1.28 (9H, s), 1.14 (3H, d), 1.10 (3H, d) and 1.03 (3H, t).

EXAMPLE 40 rel-(2S,4S,5R)-2-Isobutyl-1-(3-methoxy-4-tert-butyl-benzoyl)-4-allyloxymethyl-5-(1,3-thiazol-2-yl)pyrrolidine-2-carboxylic acid

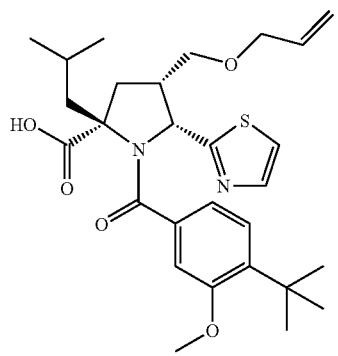

Racemic;
Relative stereochemistry shown

The title compound was prepared in a similar manner to Example 1, using Intermediate 80 as the starting material.
$^1$H NMR (CD$_3$OD): δ 7.74 (d, 1H), 7.48 (d, 1H), 7.11 (d, 1H), 6.61 (dd, 1H) 6.25 (d, 1H), 5.67 (m, 1H), 5.58 (d, 1H), 5.05 (dd, 1H), 4.99 (dd, 1H), 3.61 (d, 2H), 3.53 (s, 3H), 3.17 (m, 2H), 2.66 (t, 1H), 2.08-2.23 (m, 4H), 1.94 (m, 1H), 1.20 (s, 9H), 1.03 (d, 3H) and 1.00 (d, 3H)

EXAMPLE 41 rel-(2S,4S,5R)-2-Isobutyl-1-(3-methoxy-4-tert-butyl-benzoyl)-4-propyloxymethyl-5-(1,3-thiazol-2-yl)pyrrolidine-2-carboxylic acid

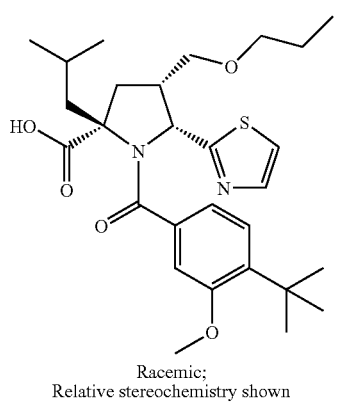

Racemic;
Relative stereochemistry shown

A solution of Example 40 (10 mg) in ethanol (4 mL) was added to 10% palladium on carbon (50 mg) and stirred under 1 atmosphere pressure of hydrogen at 20 degrees for 4 h. Catalyst was removed by filtration and washed with ethanol (10 mL). Filtrate and washings were combined and solvent was removed to give the title compound.

MS calcd for $(C_{28}H_{40}N_2O_5S+H)^+$: 517
MS found (electrospray): $(M+H)^+$=517
$^1$H NMR (CD$_3$OD): δ 7.83 (1H, d), 7.57 (1H, d), 7.20 (1H, d), 6.70 (1H, d), 6.34 (1H, dr s), 5.66 (1H, d), 3.62 (3H, s), 3.24 (2H, m), 3.10 (2H, m), 2.73 (1H, t), 2.23 (4H, m), 2.04 (1H, m), 1.45 (2H, m), 1.30 (9H, s), 1.13 (3H, d), 1.10 (3H, d) 0.84 (3H, t).

EXAMPLE 42 rel-(2S,4S,5R)-2-isobutyl-1-(3-methoxy-4-tert-butyl-benzoyl)-4-cyanomethyl-5-(1,3-thiazol-2-yl)pyrrolidine-2-carboxylic acid

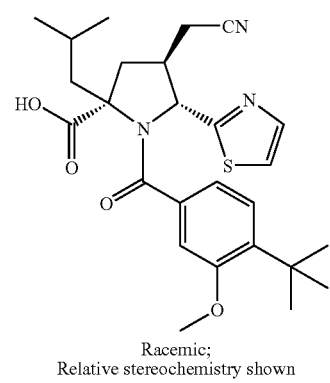

Racemic;
Relative stereochemistry shown

The title compound was prepared in a similar manner to Example 1, using Intermediate 81 as the starting material.
MS calcd for $(C_{26}H_{33}N_3O_4S+H)^+$: 484
MS found (electrospray): $(M+H)^+$=484
$^1$H NMR (CD$_3$OD): δ 7.41 (1H, d), 7.23 (1H, s), 7.14 (1H, d), 6.86 (1H, br s), 6.59 (1H, s), 5.25 (1H, d), 3.72 (3H, s), 2.92 (1H, m), 2.58 (3H, m), 2.44 (2H, m), 2.03 (1H, m), 1.89 (1H, m), 1.89 (1H, m), 1.30 (9H, s), 1.15 (3H, d), 1.00 (3H, d).

EXAMPLE 43

(2S,4S,5R)-2-Isobutyl-1-(3-methoxy-4-tert-butyl-benzoyl)-4-(1-hydroxy-1-methylethyl)-5-(1,3-thiazol-2-yl)pyrrolidine-2-carboxylic acid

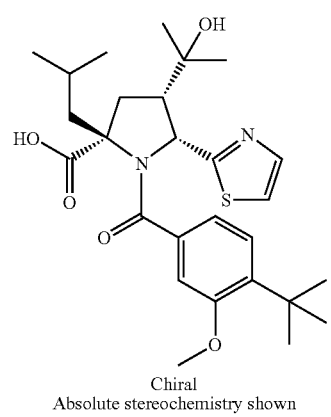

Chiral
Absolute stereochemistry shown

The title compound was prepared in a similar manner to Example 1, using Intermediate 82 as the starting material.
MS calcd for $(C_{27}H_{38}N_2O_5S+H)^+$: 503
MS found (electrospray): (M+H)+503
$^1$H NMR (CD$_3$OD): δ 7.79 (1H, d), 7.52 (1H, d), 7.21 (1H, d), 6.72 (1H, dd) 6.30 (1H, d), 5.65 (1H, d), 3.63 (3H, s), 3.09 (1H, m), 2.49 (1H, t), 2.29 (2H, m), 2.18 (1H, dd), 2.02 (1H, m), 1.31 (9H, s), 1.13 (9H, m), 0.76 (3H, s)

EXAMPLE 44 rel-(2S,4R,5R)-2-Isobutyl-1-(3-methoxy-4-tert-butylbenzoyl)-4-ethyl-5-(1,3-thiazol-2-yl)pyrrolidine-2-carboxylic acid

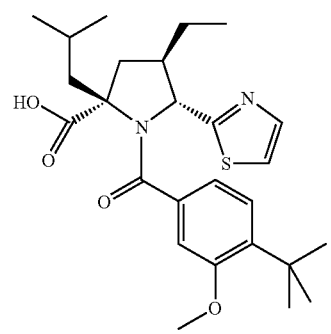

Racemic;
Relative stereochemistry shown

The title compound was prepared in a similar manner to Example 1, using Intermediate 85 as the starting material.
MS calcd for $(C_{26}H_{36}N_2O_4S+H)^+$: 473
MS found (electrospray): $(M+H)^+=473$
$^1$H NMR (CD$_3$OD): δ 7.37 (1H, d), 7.20 (1H, br s), 7.13 (1H, d), 6.85 (1H, d), 6.53 (1H, s), 5.07 (1H, d), 3.70 (3H, s), 2.40-2.55 (3H, m), 2.11 (1H, m), 2.00 (1H, dd), 1.86 (1H, m), 1.46 (1H, m), 1.38 (1H, m), 1.30 (9H, s), 1.13 (3H, d), 0.99 (3H, d), 0.83 (3H, t),

EXAMPLE 45 rel-(2S,4R,5R)-2-Isobutyl-1-(3-methoxy-4-tert-butylbenzoyl)-4-methoxymethyl-5-(pyrid-2-yl))-pyrrolidine-2-carboxylic acid

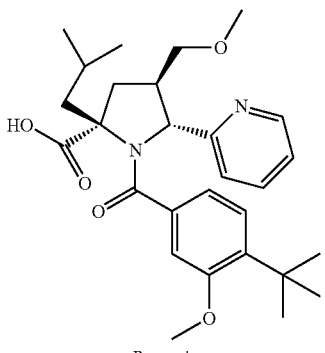

Racemic;
Relative stereochemistry shown

The title compound was prepared in a similar manner to Example 1, using Intermediate 88 as the starting material.
MS calcd for $(C_{28}H_{38}N_2O_5+H)^+$: 483
MS found (electrospray): $(M+H)^+=483$
$^1$H NMR (CD$_3$OD): δ 8.42 (1H, d), 7.53 (1H, dt), 7.22 (1H, dd), 7.17 (1H, d 6.98 (1H, d), 6.89 (1H, dd), 6.39 (1H, d), 5.17 (1H, d), 3.67 (3H, s), 3.44 (2H, m), 3.30 (3H, s), 2.69 (1H, m), 2.58 (1H, dd), 2.52 (1H, t), 2.35 (1H, dd), 2.10 (1H, dd), 1.92 (1H, m), 1.32 (9H, s), 1.18 (3H, d), 1.04 (3H, d).

EXAMPLE 46

Diastereoisomer 1 of rel-(2S,4R,5R)-2-Isobutyl-1-(3-methoxy-4-tert-butylbenzoyl)-4-(1-methoxyethyl)-5-(1,3-thiazol-2-yl)pyrrolidine-2-carboxylic acid

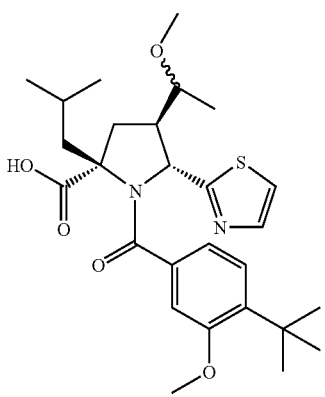

Racemic; Diastereoisomer 1
Relative stereochemistry shown

The title compound was prepared in a similar manner to Example 1, using Intermediate 94 as the starting material.
MS calcd for $(C_{27}H_{38}N_2O_5S+H)^+$: 503
MS found (electrospray): $(M+H)^+=503$
$^1$H NMR (CD$_3$OD): δ 7.37 (1H, bs), 7.20 (1H, bs), 7.14 (1H, d), 6.85 (1H, d), 6.53 (1H, s), 5.42 (1H, d), 3.35 (3H, s), 3.30 (3H, s), 3.19 (1H, m), 2.67-2.45 (3H, m), 2.21 (1H, dd), 1.96 (1H, dd), 1.83 (1H, m), 1.30 (9H, s), 1.12 (3H, d), 1.04 (3H, d), 0.98 (3H, d).

EXAMPLE 47

Diastereoisomer 2 of rel-(2S,4R,5R)-2-Isobutyl-1-(3-methoxy-tert-butylbenzoyl)-4-(1-methoxyethyl)-5-(1,3-thiazol-2-yl)pyrrolidine-2-carboxylic acid

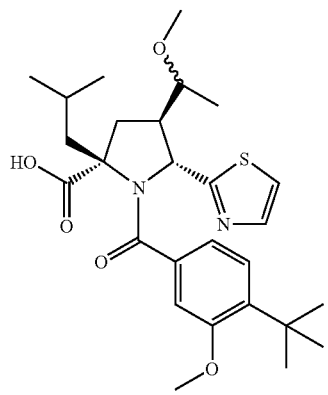

Racemic; Diastereoisomer 2
Relative stereochemistry shown

The title compound was prepared in a similar manner to Example 1, using Intermediate 95 as the starting material.
MS calcd for $(C_{27}H_{38}N_2O_5S+H)^+$: 503
MS found (electrospray): $(M+H)^+=503$
$^1$H NMR (CD$_3$OD): δ 7.35 (1H, d), 7.24 (1H, bs), 7.17 (1H, d), 6.87 (1H, d) 6.42 (1H, bs), 5.43 (1H, d), 3.68 (3H, s), 3.40 (1H, m), 3.19 (3H, s), 2.74 (1H, m), 2.49 (1H, bd), 2.36 (1H, t), 2.27 (1H, dd), 1.99 (1H, dd), 1.85 (1H, m), 1.32 (9H, s), 1.13 (3H, d), and 0.99 (6H, d).

EXAMPLE 48

Enantiomer A of (2S,4S,5R)-2-Isobutyl-1-(3-methoxy-4-tert-butylbenzoyl)-4-methoxy-methyl-5-(pyridin-2-yl)pyrrolidine-2-carboxylic acid

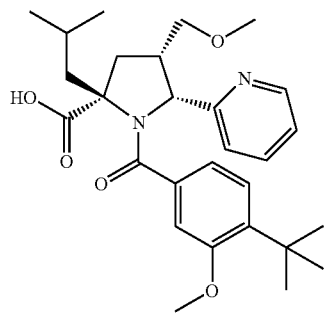

Chiral; Enantiomer A
Relative stereochemistry shown

The title compound was prepared in a similar manner to Example 1, using Intermediate 96 as the starting material.

MS calcd for $(C_{28}H_{38}N_2O_5+H)^+$: 483
MS found (electrospray): $(M+H)^+=483$
$^1H$ NMR (CD$_3$OD): δ 8.54 (1H, d), 7.51 (1H, t), 7.28 (1H, m), 7.06 (1H, d), 6.74 (1H, d), 6.62 (1H, d), 6.20 (1H, s), 5.31 (1H, d), 3.49 (3H, s), 3.15 (1H, m), 3.02 (3H, s), 2.84 (1H, dd), 2.37 (1H, t), 2.33 (1H, m), 2.19 (1H, m), 1.97 (1H, m), 1.26 (9H, s), 1.16 (3H, d), and 1.11 (3H, d).

EXAMPLE 49

Enantiomer A of rel-(2S,4S,5R)-2-Isobutyl-1-(3-methoxy-4-tert-butylbenzoyl)-4-ethoxymethyl-5-(5-methylisoxazol-3-yl)pyrrolidine-2-carboxylic acid

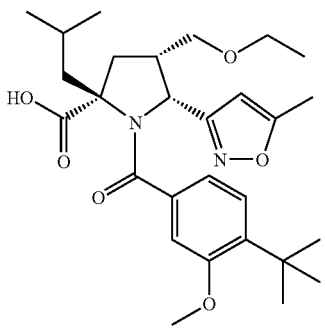

Chiral; Enantiomer A
Relative stereochemistry shown

The title compound was prepared in a similar manner to Example 1, using Intermediate 102 as the starting material.

MS calcd for $(C_{28}H_{40}N_2O_6+H)^+$: 501
MS found (electrospray): $(M+H)^+=501$
$^1H$ NMR (CD$_3$OD): δ 7.20 (1H, d), 6.74 (1H, d), 6.53 (1H, s), 6.40 (1H, s), 5.28 (1H, d), 3.68 (3H, s), 3.23 (2H, m), 3.06 (3H, m), 2.34 (3H, s), 2.19 (4H, m), 1.99 (1H, m), 1.31 (9H, s), 1.10 (9H, m).

EXAMPLE 50 rel-(2S,4S,5R)-2-Isobutyl-1-(3-methoxy-4-tert-butyl-benzoyl)-4-methoxymethyl-5-(5-methoxymethyl-1,3-thiazol-2-yl)pyrrolidine-2-carboxylic acid

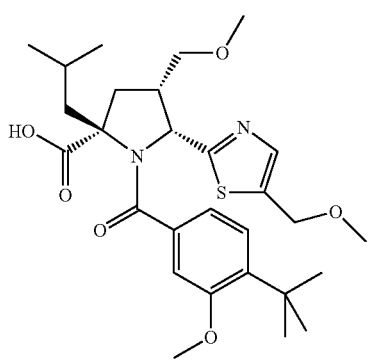

Racemic;
Relative stereochemistry shown

The title compound was prepared in a similar manner to Example 1, using Intermediate 111 as the starting material.

MS calcd for $(C_{28}H_{40}N_2O_6S+H)^+$: 533
MS found (electrospray): $(M+H)^+=533$
$^1H$ NMR (CDCl$_3$): δ 7.73 (1H, s), 7.17 (1H, d), 6.66 (1H, d), 6.38 (1H, s), (1H, s), 4.57 (2H, dd), 5.65 (1H, d), 3.62 (3H, s), 3.38-3.22 (2H, m), 3.34 (3H, s), 3.14 (3H, s), 2.63 (1H, t), 2.42-2.17 (4H, m), 2.01-1.88 (1H, m), 1.29 (9H, s), 1.12 (3H, d) and 1.10 (3H, d).

EXAMPLE 51 rel-(2S,4S,5R)-2-Isobutyl-1-(3-methoxy-4-tert-butyl-benzoyl)-4-methoxymethyl-5-(5-methylpyridin-2-yl)pyrrolidine-2-carboxylic acid

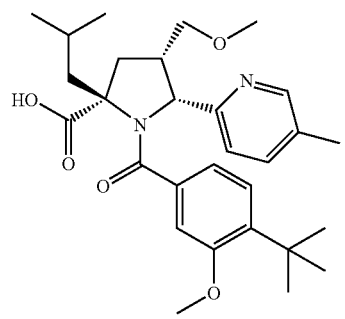

Racemic;
Relative stereochemistry shown

The title compound was prepared in a similar manner to Example 1, using Intermediate 116 as the starting material.

MS calcd for $(C_{29}H_{40}N_2O_5+H)^+$: 497
MS found (electrospray): $(M+H)^+=497$
$^1H$ NMR (CDCl$_3$): δ8.36 (1H, s), 7.29 (1H, dd), 7.06 (1H, d), 6.57-6.65 (2H, m), 6.18 (1H, d) 5.26 (1H, d), 3.49 (3H, s), 3.11-3.27 (2H, m), 3.03 (3H, s), 2.35 (3H, s), 2.08-2.54 (5H, m), 1.9-2.03 (1H, m), 1.26 (9H, s), 1.15 (3H, d) and 1.09 (3H, d).

EXAMPLE 52 rel-(2S,4S,5R)-2-Isobutyl-1-(3-methoxy-4-tert-butyl-benzoyl)-4-methoxymethyl-5-(thien-2-yl)pyrrolidine-2-carboxylic acid

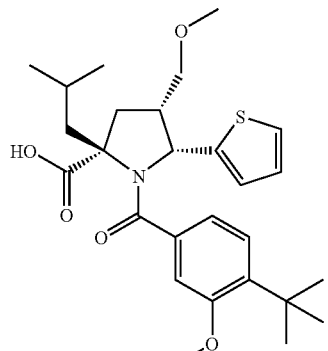

Racemic;
Relative stereochemistry shown

The title compound was prepared in a similar manner to Example 1, using Intermediate 121 as the starting material.

MS calcd for $(C_{27}H_{37}NO_5S+H)^+$: 488

MS found (electrospray) $(M+H)^+$: 488

$^1$H NMR (CDCl$_3$): δ 7.25 (dd, 1H), 7.20 (d, 1H), 6.96 (dd, 1H), 6.65 (m, 2H), 6.35 (b, 1H), 5.24 (d, 1H), 3.52 (s, 3H), 3.23 (dd, 1H), 3.18 (s, 3H), 2.83-2.59 (br m, 4H), 2.20 (dd, 1H), 1.93-1.80 (br m, 2H), 1.76-1.48 (br, 1H), 1.83 (s, 9H), 1.07 (d, 3H), 1.06 (d, 3H).

The compounds according to the invention may be formulated for administration in any convenient way, and the invention therefore also includes within its scope pharmaceutical compositions for use in therapy, comprising a compound of formula (I) or a physiologically acceptable salt or solvate thereof in admixture with one or more physiologically acceptable diluents or carriers.

The compounds of the present invention can be administered by different routes including intravenous, intraperitoneal, subcutaneous, intramuscular, oral, topical, transdermal, or transmucosal administration. For systemic administration, oral administration is preferred. For oral administration, for example, the compounds can be formulated into conventional oral dosage forms such as capsules, tablets and liquid preparations such as syrups, elixirs and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringers solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various compounds to be administered can be determined by standard procedures taking into account factors such as the compound (IC$_{50}$) potency, (EC$_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered. Oral administration is a preferred method of administration of the present compounds.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula (I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil. olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

No unacceptable toxological effects are expected when compounds of the present invention are administered in accordance with the present invention.

ASSAYS

The potential for compounds of the invention to inhibit NS5B wildtype HCV polymerase activity may be demonstrated, for example, using one of the following in vitro assays:

In Vitro Detection of Inhibitors of HCV RNA-Dependent RNA Polymerase Activity (A)

Incorporation of [$^3$H]-UMP into RNA was followed by absorption of the RNA polymer onto a DEAE glass fibre filter. A synthetic template consisting of 16 mer oligoU hybridised to polyrA (10:1 w/w) was used as a homopolymer substrate.

Reaction Conditions were 22 µM [$^3$H]-UTP (0.75 Ci/mMol), 1 mM-Dithiothreitol, 3.2 mM-MgCl$_2$, 20 mM-Tris-HCl, pH7.0, 10 µg/mL polyA-oligoU, and 90 mM-NaCl. Note that 50 mM-NaCl is added with the enzyme.

HCV RNA Polymerase (Recombinant full-length NS5B (Lohmann et al, J. Virol. 71 (11), 1997, 8416 'Biochemical properties of hepatitis C virus NS5B RNA-dependent RNA polymerase and identification of amino acid sequence motifs essential for enzymatic activity') expressed in baculovirus and purified to homogeneity) was diluted to about 50 µg protein/mL (dependent on specific activity) in 50 mM-Hepes, pH7.0, 0.5M-NaCl, 20%-Glycerol, 0.05%-Triton X-100, 5 mM-Dithiothreitol, 0.1 mM-EDTA.

5× Concentrated Buffer mix was prepared using 1M-Tris-HCl (pH7.0, 1 mL), 1M-MgCl$_2$ (0.16 mL), 1M-Dithiothreitol (0.05 mL), 5M-NaCl (0.4 mL), and Water (8.4 mL), Total 10 mL.

Substrate Mix was prepared using 5× Concentrated Buffer mix (12 µL), [$^3$H]-UTP (1 µCi/µL; 21.7 µM, 1 µL), 22 µM-UTP (100 µM, 13.2 µL), 10 µg/mL polyA-oligoU (100 µg/mL, 6 µL), and Water (12.8 µL), Total 45 µL.

The Assay was set up using Substrate Mix (45 µL), compound (10 µL), and Diluted Enzyme (added last to start reaction) (5 µL), Total 60 µL.

The reaction was performed in a U-bottomed, clear, 96-well plate. The reaction was mixed on a plate-shaker, after addition of the Enzyme, and incubated for 2 h at 22° C. After this time, the reaction was stopped by addition of 25 µL of 100 mM-EDTA.

A DEAE Filtermat (Part No. 1205-405 from Pharmacia) was pre-washed in water and alcohol and dried. 2×20 µL of the Stopped Assay Mix was spotted onto a square of the DEAE Filtermat. The DEAE Filtermat was washed for 2×15 min in SSC buffer (0.3M-NaCl, 30 mM-Na Citrate) followed by 2×2 min in water and 1×1 min in alcohol. The Filtermat was dried and sealed in a bag together with 10 mL of OptiScint HiSafe scintillation fluid. The radioactivity present on the filtermat was detected by scintillation counting on a Wallac 1205 Betaplate counter. After subtraction of background levels without enzyme, any reduction in the amount of radioactivity incorporated in the presence of a compound, compared to that in the absence, was taken as a measure of the level of inhibition. Ten concentrations of compounds were tested in two- or threefold dilutions. From the counts, percentage of inhibition at highest concentration tested or IC$_{50}$s for the compounds were calculated using Grafit3 or Grafit4 software packages.

In Vitro Detection of Inhibitors of HCV RNA-Dependent RNA Polymerase Activity (B)

Incorporation of [$^{33}$P]-GMP into RNA was followed by absorption of the biotin labelled RNA polymer by streptavidin containing SPA beads. A synthetic template consisting of biotinylated 13 mer-oligoG hybridised to polyrC was used as a homopolymer substrate.

Reaction Conditions were 0.5 µM [$^{33}$P]-GTP (0.2 Ci/mMol), 1 mM Dithiothreitol, 20 mM MgCl$_2$, 5 mM MnCl$_2$ 20 mM Tris-HCl, pH7.5, 1.6 µg/mL polyC/0.256 µM biotinylated oligoG13, 10% glycerol, 0.01% NP-40, 0.2 u/µL RNasin and 50 mM NaCl.

HCV RNA Polymerase (Recombinant full-length NS5B (Lohmann et al, J. Virol. 71 (11), 1997, 8416 'Biochemical properties of hepatitis C virus NS5B RNA-dependent RNA polymerase and identification of amino acid sequence motifs essential for enzymatic activity') expressed in baculovirus and purified to homogeneity) was added to 10 nM final concentration.

5× concentrated assay buffer mix was prepared using 1M MnCl$_2$ (0.25 mL), glycerol (4 mL), 10% NP-40 (0.025 mL) and Water (7.225 mL), Total 10 mL.

2× concentrated enzyme buffer contained 1M-Tris-HCl, pH7.5 (0.4 mL), 5M NaCl (0.2 mL), 1M-MgCl$_2$(0.4 mL), glycerol (1 mL), 10% NP-40 (10 µL), 1M DTT (20 µL) and water (7.97 mL), Total 10 mL.

Substrate Mix was prepared using 5× Concentrated assay Buffer mix (4 µL), [$^{33}$P]-GTP (10 µCi/µL, 0.02 µL), 25 µm GTP (0.4 µL), 0.4 u/µL RNasin (0.04 µL), 20 µg/mL polyrC/biotinylated-oligorG (1.6 µL), and Water (3.94 µL), Total 10 µL.

Enzyme Mix was prepared by adding 1 mg/ml full-length NS5B polymerase (1.5 µL) to 2.811 mL 2×-concentrated enzyme buffer.

The Assay was set up using compound (1 µL), Substrate Mix (10 µL), and Enzyme Mix (added last to start reaction) (10 µL), Total 21 µL.

The reaction was performed in a U-bottomed, white, 96-well plate. The reaction was mixed on a plate-shaker, after addition of the Enzyme, and incubated for 1 h at 22° C. After this time, the reaction was stopped by addition of 40 µL 1.875 mg/ml streptavidin SPA beads in 0.1 M EDTA. The beads were incubated with the reaction mixture for 1 h at 22° C. after which 120 µL 0.1 M EDTA in PBS was added. The plate was sealed, mixed centrifuged and incorporated radioactivity determined by counting in a Trilux (Wallac) or Topcount (Packard) Scintillation Counter.

After subtraction of background levels without enzyme, any reduction in the amount of radioactivity incorporated in the presence of a compound, compared to that in the absence, was taken as a measure of the level of inhibition. Ten concentrations of compounds were tested in three- or fivefold dilutions. From the counts, percentage of inhibition at highest concentration tested or IC$_{50}$s for the compounds were calculated using Grafit3 or Grafit4 software packages.

The exemplified compounds all had an IC$_{50}$ of <50 µM in one of the above described assays. Accordingly, the compounds of the invention are of potential therapeutic benefit in the treatment and prophylaxis of HCV. Preferred compounds had an IC$_{50}$ of <5 µM.

The pharmaceutical compositions according to the invention may also be used in combination with other therapeutic agents, for example immune therapies (eg. Interferon, such as Interferon alfa-2a (Roferon-A; Hoffmann-La Roche), interferon alpha-2b (Intron-A; Schering-Plough), interferon alfacon-1 (Infergen; Intermune), peginterferon alpha-2b (Peg-Intron; Schering-Plough) or peginterferon alpha-2a (Pegasys; Hoffmann-La Roche)), therapeutic vaccines, anti-fibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

The invention thus provides, in a further aspect, a combination comprising a compound of formula (I) or a physiologically acceptable salt or solvate thereof together with another therapeutically active agent, especially interferon and/or ribavirin.

The combinations referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

All publications, including but not limited to patents and patent applications cited in this specification are herein incorporated by reference as if each individual publication were specifically and individually indicated to be incorporated by reference as though fully set forth.

The invention claimed is:

1. Compounds of Formula (Ia):

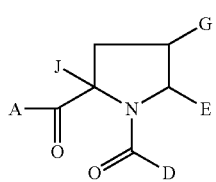

wherein:
A represents hydroxy;
D represents aryl;
E represents heteroaryl or heterocyclyl;
G represents hydrogen or $C_{1-6}$alkyl optionally substituted by one or more substituents selected from halo, $OR^1$, $SR^1$, $C(O)NR^2R^3$, $CO_2H$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano, aryl, heteroaryl and heterocyclyl;
$R^1$ represents hydrogen, $C_{1-6}$alkyl, arylalkyl, or heteroarylalkyl;
$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;
$R^4$ is selected from the group consisting of $C_{1-6}$alkyl, aryl, heteroaryl, arylalkyl, and heteroarylalkyl;
$R^5$ and $R^6$ are independently selected from the group consisting of hydrogen, $C_{1-6}$alkyl, aryl, heteroaryl, arylalkyl, and heteroarylalkyl; or $R^5$ and $R^6$ together with the nitrogen atom to which they are attached form a 5 or 6 membered saturated cyclic group; and
J represents $C_{1-6}$alkyl, heterocyclylalkyl, arylalkyl or heteroarylalkyl;
and salts, solvates and esters thereof; provided that when A is esterified to form —OR where R is selected from straight or branched chain alkyl, aralkyl, aryloxyalkyl, or aryl, then R is other than tert-butyl.

2. A compound selected from the group consisting of:
rel-(2S,4R,5R)-2-Isobutyl-1-(3-methoxy-4-tert-butylbenzoyl)-4-ethoxymethyl-5-(1,3-thiazol-2-yl)pyrrolidine-2-carboxylic acid;
rel-(2S,4R,5R)-2-Isobutyl-1-(3-methoxy-4-tert-butylbenzoyl)-4-methoxymethyl-5-(1,3-thiazol-2-yl)pyrrolidine-2-carboxylic acid;
rel-(2S,4R,5R)-2-Isobutyl-1-(3-methoxy-4-tert-butylbenzoyl)-4-fluoromethyl-5-(1,3-thial-2-yl)pyrrolidine-2-carboxylic acid;
rel-(2S,4R,5R)-2-Isobutyl-1-(3-methoxy-4-tert-butylbenzoyl)-4-methyl-5-(1,3-thiazol-2-yl)pyrrolidine-2-carboxylic acid;
rel-(2S,4R,5R)-2-Isobutyl-1-(3-methoxy-4-tert-butylbenzoyl)-4-hydroxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-hydroxymethyl-5-(1,3-thiazol-2-yl)pyrrolidine-2-carboxylic acid;
rel-(2S,4R,5R)-2-Isobutyl-1-(3-methoxy-4-tert-butylbenzoyl)-4-allyloxymethyl-5-(1,3-thiazol-2-yl)pyrrolidine-2-carboxylic acid;
rel-(2S,4R,5R)-2-Isobutyl-1-(3-methoxy-4-tert-butylbenzoyl)-4-propyloxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-methoxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid;
rel-(2S,4S,5R)-2-Isobutyl-1-(3-methoxy-4-tert-butylbenzoyl)-4-isopropenyl-5-(1,3-thiazol-2-yl)pyrrolidine-2-carboxylic acid;
rel-(2S,4S,5R)-2-Isobutyl-1-(3-methoxy-4-tert-butylbenzoyl)-4-isopropyl-5-(1,3-thiazol-2-yl)pyrrolidine-2-carboxylic acid;
(2S,4S,5R)-2-Isobutyl-1-(3-methoxy-4-tert-butylbenzoyl)-4-methoxymethyl-5-(1,3-thiazol-2-yl)pyrrolidine-2-carboxylic acid;
(2S,4S,5R)-2-Isobutyl-1-(3-methoxy-4-tert-butylbenzoyl)-4-ethoxymethyl-5-(1,3-thiazol-2-yl)pyrrolidine-2-carboxylic acid;
(2S,4S,5R)-2-Isobutyl-1-(3-bromo-4-tert-butylbenzoyl)-4-ethoxymethyl-5-(1,3-thiazol-2-yl)-pyrrolidine-2-carboxylic acid;
(2S,4S,5R)-2-Isobutyl-1-(3-chloro-4-tert-butylbenzoyl)-4-ethoxymethyl-5-(1,3-thiazol-2-yl)-pyrrolidine-2-carboxylic acid;
(2S,4S,5R)-2-Isobutyl-1-(3-methyl-4-tert-butylbenzoyl)-4-ethoxymethyl-5-(1,3-thiazol-2-yl)pyrrolidine-2-carboxylic acid;
rel-(2R,4R,5R)-2-Benzyl-1-(3-methoxy-4-tert-butylbenzoyl)-4-methoxymethyl-5-(1,3-thiazol-2-yl)-pyrrolidine-2-carboxylic acid;
rel-(2R,4R,5R)-2-Benzyl-1-(3-methoxy-4-tert-butylbenzoyl)-4-ethoxymethyl-5-(1,3-thiazol-2-yl)-pyrrolidine-2-carboxylic acid;
rel-(2S,4S,5R)-2-Isobutyl-1-(3-methoxy-4-tert-butylbenzoyl)-4-methoxymethyl-5-(pyrazin-2-yl)pyrrolidine-2-carboxylic acid;
rel-(2S,4R,5R)-2-Isobutyl-1-(3-methoxy-4-tert-butylbenzoyl)-4-methoxymethyl-5-(pyrazin-2-yl)pyrrolidine-2-carboxylic acid;
rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid;
rel-(2S,4S,5R)-2-Isobutyl-1-(3-methoxy-4-tert-butylbenzoyl)-4-methoxymethyl-5-(5-methyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(2-chloro-1,3-thiazol-5-yl)pyrrolidine-2-carboxylic acid;

rel-(2S,4S,5R)-2-Isobutyl-1-(3-methoxy-4-tert-butylbenzoyl)-4-methoxymethyl-5-(2-methoxy-1,3-thiazol-5-yl)pyrrolidine-2-carboxylic acid;

rel-(2S,4R,5R)-2-Isobutyl-1-(3-methoxy-4-tert-butylbenzoyl)-4-((methylthio)methyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-((methanesulfonyl)methyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-(1,1-difluoroethyl)-5(1,3-thiazol-2-yl)pyrrolidine-2-carboxylic acid;

rel-(2S,4R,5R)-2-Isobutyl-1-(3-methoxy-4-tert-butylbenzoyl)-4-(1-hydroxy-1-methylethl)-5-(1,3-thiazol-2-yl)pyrrolidine-2-carboxylic acid;

rel-(2R,4S,5R)-2-Benzyl-1-(3-methoxy-4-tert-butylbenzoyl)-4-methoxymethyl-5-(1,3-thiazol-2-yl)-pyrrolidine-2-carboxylic acid;

rel-(2R,4S,5R)-2-Benzyl-1-(3-methoxy-4-tert-butylbenzoyl)-4-ethoxymethyl-5-(1,3-thiazol-2-yl)-pyrrolidine-2-carboxylic acid;

rel-(2S,4S,5R)-2-Isobutyl-1-(3-methoxy-4-tert-butylbenzoyl)-4-methoxymethyl-5-(pyridin-2-yl)pyrrolidine-2-carboxylic acid;

(2S,4R,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

(2S,4R,5R)-2-Isobutyl-1-(3-methoxy-4-tert-butylbenzoyl)-4-(1-hydroxyethyl)-5-(1,3-thiazol-2-yl)pyrrolidine-2-carboxylic acid;

rel-(2S,4S,5R)-2-Isobutyl-1-(3-methoxy-4-tert-butylbenzoyl)-4-ethoxymethyl-5-(1,3-thiazol-4-yl)pyrrolidine-2-carboxylic acid;

rel-(2S,4S,5R)-2-Isobutyl-1-(3-methoxy-4-tert-butylbenzoyl)-4-allyloxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-propyloxymethyl-5-(1,3-thiazol-2-yl)pyrrolidine-2-carboxylic acid;

rel-(2S,4S,5R)-2-Isobutyl-1-(3-methoxy-4-tert-butylbenzoyl)-4-cyanomethyl-5-(1,3-thiazol-2-yl)pyrrolidine-2-carboxylic acid;

(2S,4S,5R)-2-Isobutyl-1-(3-methoxy-4-tert-butylbenzoyl)-4-(1-hydroxy-1-methylethyl)-5-(1,3-thiazol-2-yl)pyrrolidine-2-carboxylic acid;

rel-(2S,4R,5R)-2-Isobutyl-1-(3-methoxy-4-tert-butylbenzoyl)-4-ethyl-5-(1,3-thiazol-2-yl)pyrrolidine-2-carboxylic acid;

rel-(2S,4R,5R)-2-Isobutyl-1-(3-methoxy-4-tert-butylbenzoyl)-4-methoxymethyl-5-(pyrid-2-yl))-pyrrolidine-2-carboxylic acid;

rel-(2S,4R,5R)-2-Isobutyl-1-(3-methoxy-4-tert-butylbenzoyl)-4-(1-methoxyethyl)-5-(1,3-thiazol-2-yl)pyrrolidine-2-carboxylic acid;

(2S,4S,5R)-2-Isobutyl-1-(3-methoxy-4-tert-butylbenzoyl)-4-methoxymethyl-5-(pyridin-2-yl)pyrrolidine-2-carboxylic acid;

rel-(2S,4S,5R)-2-Isobutyl-1-(3-methoxy-4-tert-butylbenzoyl)-4-ethoxymethyl-5-(5-methylisoxazol-3-yl)pyrrolidine-2-carboxylic acid;

rel-(2S,4S,5R)-2-Isobutyl-1-(3-methoxy-4-tert-butylbenzoyl)-4-methoxymethyl-5-(5-methoxymethyl-1,3-thiazol-2-yl)pyrrolidine-2-carboxylic acid;

rel-(2S,4S,5R)-2-Isobutyl-1-(3-methoxy-4-tert-butylbenzoyl)-4-methoxymethyl-5-(5-methylpyridin-2-yl)pyrrolidine-2-carboxylic acid;

rel-(2S,4S,5R)-2-Isobutyl-1-(3-methoxy-4-tert-butylbenzoyl)-4-methoxymethyl-5-(thien-2-yl)pyrrolidine-2-carboxylic acid;

and salts, solvates and esters, and individual enantiomers thereof.

3. A compound of Formula (Ia) as claimed in claim 1 wherein D represents optionally substituted phenyl.

4. A compound of Formula (Ia) as claimed in claim 3 wherein D represents para-tert-butylphenyl optionally further substituted by halo, $C_{1-3}$alkyl or $C_{1-3}$alkoxy.

5. A compound of Formula (Ia) as claimed in claim 1 wherein E represents optionally substituted heteroaryl.

6. A compound of Formula (Ia) as claimed in claim 5 wherein E represents optionally substituted thiazolyl, pyridinyl, pyrazinyl, isoxazolyl and thienyl.

7. A compound of Formula (Ia) as claimed in claim 1 wherein G represents $C_{1-6}$alkyl optionally substituted by halo, $OR^1$, $SR^1$, $SO_2R^4$ and cyano.

8. A compound of Formula (Ia) as claimed in claim 7 wherein G represents $C_{1-6}$alkyl optionally substituted by $OR^1$.

9. A compound of Formula (Ia) as claimed in claim 7 wherein $R^1$ represents hydrogen or $C_{1-3}$alkyl.

10. A compound of Formula (Ia) as claimed in claim 7 wherein $R^4$ represents $C_{1-3}$alkyl.

11. A compound of Formula (Ia) as claimed in claim 1 wherein J represents $C_{1-6}$alkyl, arylalkyl or heteroarylalkyl.

12. A compound of Formula (Ia) as claimed in claim 1, and pharmaceutically acceptable salts and solvates thereof.

13. A method of treating an HCV infection which comprises administering to a subject in need thereof, an effective amount of a compound of Formula (I)

(I)

wherein:

A represents hydroxy;

D represents aryl;

E represents heteroaryl or heterocyclyl;

G represents hydrogen or $C_{1-6}$alkyl optionally substituted by one or more substituents selected from halo, $OR^1$, $SR^1$, $C(O)NR^2R^3$, $CO_2H$, $C(O)R^4$, $CO_2R^4$, $NR^2R^3$, $NHC(O)R^4$, $NHCO_2R^4$, $NHC(O)NR^5R^6$, $SO_2NR^5R^6$, $SO_2R^4$, nitro, cyano, aryl, heteroaryl and heterocyclyl;

$R^1$ represents hydrogen, $C_{1-6}$alkyl, arylalkyl, or heteroarylalkyl;

$R^2$ and $R^3$ are independently selected from hydrogen, $C_{1-6}$alkyl, aryl and heteroaryl; or $R^2$ and $R^3$ together with the nitrogen atom to which they are attached form a 5 or 6 membered saturated cyclic group;

$R^4$ is selected from the group consisting of $C_{1-6}$alkyl, aryl, heteroaryl, arylalkyl, and heteroarylalkyl;

$R^5$ and $R^6$ are independently selected from the group consisting of hydrogen, $C_{1-6}$alkyl, aryl, heteroaryl, arylalkyl, and heteroarylalkyl; or $R^5$ and $R^6$ together with the nitrogen atom to which they are attached form a 5 or 6 membered saturated cyclic group; and J represents $C_{1-6}$alkyl, heterocyclylalkyl, arylalkyl or heteroarylalkyl;

and salts, solvates and esters thereof; provided that when A is esterified to form —OR where R is selected from straight or branched chain alkyl, aralkyl, aryloxyalkyl, or aryl, then R is other than tert-butyl.

14. A method as claimed in claim 13 in which the compound is administered in an oral dosage form.

15. A pharmaceutical formulation comprising a compound of Formula (Ia) as defined in claim 1 in conjunction with a pharmaceutically acceptable diluent or carrier.

16. A process for the preparation of a compound of Formula (Ia) as defined in claim 1, comprising treatment of a compound of Formula (II)

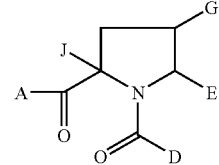

(II)

in which A is alkoxy, and D, E, G and J are as defined for Formula (Ia), with an acid.

17. A process as claimed in claim 16 in which A is tert-butoxy.

18. A compound of Formula (Ia) as claimed in claim 8 wherein $R^1$ represents hydrogen or $C_{1-3}$alkyl.

* * * * *